(12) United States Patent
Lu et al.

(10) Patent No.: US 10,035,788 B2
(45) Date of Patent: *Jul. 31, 2018

(54) MALEATE SALTS OF (E)-N-{4[3-CHLORO-4-(2-PYRIDINYLMETHOXY)ANILINO]-3-CYANO-7-ETHOXY-6-QUINOLINYL}-4-(DIMETHYLAMINO)-2-BUTENAMIDE AND CRYSTALLINE FORMS THEREOF

(71) Applicant: Wyeth LLC, New York, NY (US)

(72) Inventors: Qinghong Lu, Suffern, NY (US); Mannching Sherry Ku, Thiells, NY (US); Warren Chew, Pierrefonds (CA); Gloria Cheal, Beaconsfield (CA); Anthony F. Hadfield, St. Petersburg, FL (US); Mahmoud Mirmehrabi, Laval (CA)

(73) Assignee: WYETH LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/463,998

(22) Filed: Mar. 20, 2017

(65) Prior Publication Data

US 2017/0320852 A1 Nov. 9, 2017

Related U.S. Application Data

(60) Continuation of application No. 14/825,612, filed on Aug. 13, 2015, now Pat. No. 9,630,946, which is a continuation of application No. 13/765,356, filed on Feb. 12, 2013, now Pat. No. 9,139,558, which is a continuation of application No. 13/441,168, filed on Apr. 6, 2012, now Pat. No. 8,394,959, which is a continuation of application No. 13/181,375, filed on Jul. 12, 2011, now Pat. No. 8,173,814, which is a division of application No. 12/251,924, filed on Oct. 15, 2008, now Pat. No. 8,022,216.

(60) Provisional application No. 61/124,796, filed on Oct. 17, 2007.

(51) Int. Cl.
| | |
|---|---|
| A61K 31/4709 | (2006.01) |
| C07D 401/12 | (2006.01) |
| C07C 57/145 | (2006.01) |
| C07C 51/41 | (2006.01) |

(52) U.S. Cl.
CPC ........ *C07D 401/12* (2013.01); *A61K 31/4709* (2013.01); *C07C 51/412* (2013.01); *C07C 57/145* (2013.01)

(58) Field of Classification Search
CPC .... C07D 401/12; C07D 215/44; C07C 51/41; C07C 57/145; A61K 31/4709
See application file for complete search history.

(56) References Cited

U.S. PATENT DOCUMENTS

| | | | |
|---|---|---|---|
| 4,966,891 | A | 10/1990 | Fujiu et al. |
| 5,362,718 | A | 11/1994 | Skotnicki et al. |
| 5,453,497 | A | 9/1995 | Kamiya et al. |
| 5,472,949 | A | 12/1995 | Arasaki et al. |
| 5,476,932 | A | 12/1995 | Brinkman et al. |
| 5,715,151 | A | 2/1998 | Moriura |
| 5,760,041 | A | 6/1998 | Wissner et al. |
| 6,002,008 | A | 12/1999 | Wissner et al. |
| 6,143,764 | A | 11/2000 | Kubo et al. |
| 6,251,912 | B1 | 6/2001 | Wissner et al. |
| 6,277,983 | B1 | 8/2001 | Shaw et al. |
| 6,288,082 | B1 | 9/2001 | Wissner et al. |
| 6,297,258 | B1 | 10/2001 | Wissner et al. |
| 6,384,051 | B1 | 5/2002 | Frost et al. |
| 6,387,371 | B1 | 5/2002 | Hudziak et al. |
| 6,399,063 | B1 | 6/2002 | Hudziak et al. |
| 6,432,979 | B1 | 8/2002 | Frost et al. |
| 6,511,986 | B2 | 1/2003 | Zhang et al. |
| 6,617,333 | B2 | 9/2003 | Rabindran et al. |
| 6,780,996 | B2 | 8/2004 | Boschelli et al. |
| 6,821,515 | B1 | 11/2004 | Cleland et al. |
| 6,821,988 | B2 | 11/2004 | Wissner et al. |
| 7,026,330 | B2 | 4/2006 | Grupp et al. |
| 7,091,213 | B2 | 8/2006 | Metcalf et al. |
| 7,126,025 | B2 | 10/2006 | Considine et al. |
| 7,189,735 | B2 | 3/2007 | Dukart et al. |
| 7,235,564 | B2 | 6/2007 | Scott et al. |
| 7,294,468 | B2 | 11/2007 | Bell et al. |
| 7,297,795 | B2 | 11/2007 | Sutherland et al. |
| 7,306,801 | B2 | 12/2007 | Caligiuri et al. |
| RE40,418 | E | 7/2008 | Rabindran et al. |
| 7,399,865 | B2 | 7/2008 | Wissner et al. |
| 7,846,936 | B2 | 12/2010 | Hilberg et al. |
| 7,897,159 | B2 | 3/2011 | Weber |
| 7,915,402 | B2 | 3/2011 | Anderson et al. |
| 7,943,778 | B2 | 5/2011 | Jiang et al. |
| 7,964,349 | B2 | 6/2011 | Bell et al. |
| 7,982,043 | B2 | 7/2011 | Wissner et al. |

(Continued)

FOREIGN PATENT DOCUMENTS

| | | |
|---|---|---|
| CN | 1437942 A | 8/2003 |
| CN | 101185633 A | 5/2008 |

(Continued)

OTHER PUBLICATIONS

"Trastuzumab." Wikipedia: Wikipedia: The Free Encyclopedia. Wikimedia Foundation, Inc. Retrieved from the Internet Aug. 14, 2009. Url:http://en.wikipedia.org/wiki/Herceptin.

(Continued)

*Primary Examiner* — D Margaret M Seaman
(74) *Attorney, Agent, or Firm* — Jones Day

(57) ABSTRACT

The present invention relates to maleate salt forms of (E)-N-{4-[3-chloro-4-(2-pyridinylmethoxy)anilino]-3-cyano-7-ethoxy-6-quinolinyl}-4-(dimethylamino)-2-butenamide, methods of preparing crystalline maleate salt forms, the associated compounds, and pharmaceutical compositions containing the same. The maleate salts are useful in treating cancers, particularly those affected by kinases of the epidermal growth factor receptor family.

24 Claims, 8 Drawing Sheets

(56) References Cited

U.S. PATENT DOCUMENTS

| | | | |
|---|---|---|---|
| 8,022,216 B2* | 9/2011 | Lu | C07D 401/12 |
| | | | 546/160 |
| 8,105,769 B2 | 1/2012 | Bell et al. | |
| 8,173,814 B2 | 5/2012 | Lu et al. | |
| 8,173,817 B2* | 5/2012 | Reddy | C07D 401/12 |
| | | | 546/273.7 |
| 8,338,456 B2 | 12/2012 | Coughlin et al. | |
| 8,394,959 B2* | 3/2013 | Lu | C07D 401/12 |
| | | | 546/153 |
| 8,465,916 B2 | 6/2013 | Bell et al. | |
| 8,518,446 B2 | 8/2013 | Asraf et al. | |
| 8,524,281 B2 | 9/2013 | Rao et al. | |
| 8,669,273 B2 | 3/2014 | Zacharchuk et al. | |
| 8,790,708 B2 | 7/2014 | Asraf et al. | |
| 9,139,558 B2* | 9/2015 | Lu | C07D 401/12 |
| 9,630,946 B2* | 4/2017 | Lu | C07D 401/12 |
| 2002/0002162 A1 | 1/2002 | Lee | |
| 2002/0183239 A1 | 12/2002 | Gibbons et al. | |
| 2002/0183240 A1 | 12/2002 | Gibbons et al. | |
| 2002/0198137 A1 | 12/2002 | Dukart et al. | |
| 2002/0198317 A1 | 12/2002 | Fong et al. | |
| 2003/0144252 A1 | 7/2003 | Furr | |
| 2003/0149056 A1 | 8/2003 | Wissner et al. | |
| 2003/0153593 A1 | 8/2003 | Dukart et al. | |
| 2004/0039010 A1 | 2/2004 | Grupp et al. | |
| 2004/0162442 A1 | 8/2004 | Considine et al. | |
| 2004/0176339 A1 | 9/2004 | Sherman et al. | |
| 2004/0209930 A1 | 10/2004 | Carboni et al. | |
| 2004/0258662 A1 | 12/2004 | Gibbons et al. | |
| 2005/0025825 A1 | 2/2005 | Heasley et al. | |
| 2005/0032825 A1 | 2/2005 | Metcalf et al. | |
| 2005/0038080 A1 | 2/2005 | Boyer et al. | |
| 2005/0043233 A1 | 2/2005 | Stefanic et al. | |
| 2005/0059678 A1 | 3/2005 | Wissner et al. | |
| 2005/0129761 A1 | 6/2005 | Rao et al. | |
| 2005/0136063 A1 | 6/2005 | Wang et al. | |
| 2005/0187184 A1 | 8/2005 | Gibbons et al. | |
| 2005/0272083 A1 | 12/2005 | Seshagiri | |
| 2005/0272758 A1 | 12/2005 | Bayever et al. | |
| 2006/0030547 A1 | 2/2006 | Dukart et al. | |
| 2006/0035904 A1 | 2/2006 | Gibbons et al. | |
| 2006/0058311 A1 | 3/2006 | Munzert et al. | |
| 2006/0079515 A1 | 4/2006 | Frost | |
| 2006/0084666 A1 | 4/2006 | Harari et al. | |
| 2006/0094674 A1 | 5/2006 | Neel et al. | |
| 2006/0128793 A1 | 6/2006 | Zask et al. | |
| 2006/0147959 A1 | 7/2006 | Bell et al. | |
| 2006/0178387 A1 | 8/2006 | Fujimoto/Ouchi et al. | |
| 2006/0235046 A1 | 10/2006 | Zacharchuk et al. | |
| 2006/0270668 A1 | 11/2006 | Chew et al. | |
| 2006/0270669 A1 | 11/2006 | Chew et al. | |
| 2007/0014859 A1 | 1/2007 | Shah et al. | |
| 2007/0048754 A1 | 3/2007 | Freeman et al. | |
| 2007/0104721 A1 | 5/2007 | Moore et al. | |
| 2007/0105887 A1 | 5/2007 | Moore | |
| 2007/0281932 A1 | 12/2007 | Bernier et al. | |
| 2008/0096212 A1 | 4/2008 | Bell et al. | |
| 2008/0112888 A1 | 5/2008 | Wang | |
| 2008/0166359 A1 | 7/2008 | Lamb | |
| 2008/0193448 A1 | 8/2008 | Baum | |
| 2008/0207615 A1 | 8/2008 | Bell et al. | |
| 2008/0234264 A1 | 9/2008 | Bell et al. | |
| 2008/0254040 A1 | 10/2008 | Stefanic et al. | |
| 2008/0268034 A1 | 10/2008 | Karanth et al. | |
| 2008/0286771 A1 | 11/2008 | Hudson et al. | |
| 2008/0286785 A1 | 11/2008 | Nishio et al. | |
| 2009/0035269 A1 | 2/2009 | Weber | |
| 2009/0047278 A1 | 2/2009 | Owa et al. | |
| 2009/0060873 A1 | 3/2009 | Sporn et al. | |
| 2009/0176827 A1 | 7/2009 | Lu et al. | |
| 2009/0203709 A1 | 8/2009 | Steinberg et al. | |
| 2009/0246198 A1 | 10/2009 | Dong et al. | |
| 2009/0297519 A1 | 12/2009 | Moore et al. | |
| 2009/0306101 A1 | 12/2009 | Solca et al. | |
| 2009/0312360 A1 | 12/2009 | Zacharchuk | |
| 2009/0317456 A1 | 12/2009 | Karrasch et al. | |
| 2009/0318480 A1 | 12/2009 | Solca | |
| 2009/0325877 A1 | 12/2009 | Grunt et al. | |
| 2010/0041904 A1 | 2/2010 | Jiang et al. | |
| 2010/0048540 A1 | 2/2010 | Boyle et al. | |
| 2010/0048892 A1 | 2/2010 | Anderson et al. | |
| 2010/0056777 A1 | 3/2010 | Anderson et al. | |
| 2010/0069340 A1 | 3/2010 | Zacharchuk et al. | |
| 2010/0081632 A1 | 4/2010 | Oksenberg et al. | |
| 2010/0087482 A1 | 4/2010 | Haber et al. | |
| 2010/0092490 A1 | 4/2010 | Uenaka et al. | |
| 2010/0105031 A1 | 4/2010 | Matsui et al. | |
| 2010/0113474 A1 | 5/2010 | Zacharchuk et al. | |
| 2010/0120072 A1 | 5/2010 | Lorence et al. | |
| 2010/0120768 A1 | 5/2010 | Steinberg et al. | |
| 2010/0143340 A1 | 6/2010 | Kolhe et al. | |
| 2010/0143350 A1 | 6/2010 | Green et al. | |
| 2010/0166744 A1 | 7/2010 | Wong | |
| 2010/0189773 A1 | 7/2010 | Mortimore et al. | |
| 2010/0226943 A1 | 9/2010 | Brennan et al. | |
| 2010/0297118 A1 | 11/2010 | Macdougall et al. | |
| 2010/0298760 A1 | 11/2010 | Olle et al. | |
| 2010/0310503 A1 | 12/2010 | Li et al. | |
| 2011/0014117 A1 | 1/2011 | Wang et al. | |
| 2011/0045459 A1 | 2/2011 | Mischel et al. | |
| 2011/0052570 A1 | 3/2011 | Klagsbrun et al. | |
| 2011/0091421 A1 | 4/2011 | Mann | |
| 2011/0091524 A1 | 4/2011 | Wang et al. | |
| 2011/0097340 A1 | 4/2011 | Ramachandra et al. | |
| 2011/0104256 A1 | 5/2011 | Wang et al. | |
| 2011/0111018 A1 | 5/2011 | Asraf et al. | |
| 2011/0112180 A1 | 5/2011 | Jiang et al. | |
| 2011/0129456 A1 | 6/2011 | Wang et al. | |
| 2011/0165257 A1 | 7/2011 | Rao et al. | |
| 2012/0071507 A1 | 3/2012 | Berkenblit et al. | |
| 2012/0270896 A1 | 10/2012 | Zacharchuk | |
| 2012/0308560 A1 | 12/2012 | Moore et al. | |
| 2013/0189274 A1 | 7/2013 | Berkenblit et al. | |
| 2013/0281488 A1 | 10/2013 | Lu et al. | |
| 2013/0316935 A1 | 11/2013 | Bell et al. | |
| 2014/0004203 A1 | 1/2014 | Rao et al. | |
| 2014/0050721 A1 | 2/2014 | Moore et al. | |
| 2014/0171384 A1 | 6/2014 | Zacharchuk et al. | |

FOREIGN PATENT DOCUMENTS

| | | |
|---|---|---|
| EP | 0693285 A2 | 1/1996 |
| EP | 1448531 B1 | 8/2007 |
| EP | 1663978 B1 | 11/2007 |
| EP | 1854463 A1 | 11/2007 |
| EP | 1978106 A1 | 10/2008 |
| EP | 1951274 B1 | 12/2009 |
| EP | 1848414 B1 | 4/2011 |
| EP | 1859793 B1 | 4/2011 |
| EP | 2656844 A1 | 10/2013 |
| JP | 2003-519689 A | 6/2003 |
| JP | 2003-519698 A | 6/2003 |
| JP | 2007-145745 A | 6/2007 |
| WO | WO 1992/022653 A1 | 12/1992 |
| WO | WO 1995/028406 A1 | 10/1995 |
| WO | WO 1996/033978 A1 | 10/1996 |
| WO | WO 1996/033980 A1 | 10/1996 |
| WO | WO 1998/043960 A1 | 10/1998 |
| WO | WO 2000/018761 A1 | 4/2000 |
| WO | WO 2001/023395 A2 | 4/2001 |
| WO | WO 2001/051919 A2 | 7/2001 |
| WO | WO 2002/080975 A1 | 10/2002 |
| WO | WO 2002/098416 A2 | 12/2002 |
| WO | WO 2002/102976 A2 | 12/2002 |
| WO | WO 2003/050090 A1 | 6/2003 |
| WO | WO 2003/103676 A2 | 12/2003 |
| WO | WO 2004/004644 A2 | 1/2004 |
| WO | WO 2004/066919 A2 | 8/2004 |
| WO | WO 2004/078133 A2 | 9/2004 |
| WO | WO 2004/093854 A2 | 11/2004 |
| WO | WO 2004/096224 A2 | 11/2004 |
| WO | WO 2005/018677 A2 | 3/2005 |
| WO | WO 2005/032513 A2 | 4/2005 |
| WO | WO 2005/034955 A1 | 4/2005 |

(56) References Cited

FOREIGN PATENT DOCUMENTS

| | | |
|---|---|---|
| WO | WO 2005/037287 A1 | 4/2005 |
| WO | WO 2005/044091 A2 | 5/2005 |
| WO | WO 2005/049021 A1 | 6/2005 |
| WO | WO 2005/087265 A1 | 9/2005 |
| WO | WO 2005/094357 A2 | 10/2005 |
| WO | WO 2006/044453 A1 | 4/2006 |
| WO | WO 2006/044748 A2 | 4/2006 |
| WO | WO 2006/081985 A1 | 8/2006 |
| WO | WO 2006/084058 A2 | 8/2006 |
| WO | WO 2006/095185 A1 | 9/2006 |
| WO | WO 2006/098978 A1 | 9/2006 |
| WO | WO 2006/113151 A2 | 10/2006 |
| WO | WO 2006/113304 A2 | 10/2006 |
| WO | WO 2006/116514 A2 | 11/2006 |
| WO | WO 2006/120557 A1 | 11/2006 |
| WO | WO 2006/120573 A2 | 11/2006 |
| WO | WO 2006/127205 A2 | 11/2006 |
| WO | WO 2006/127207 A1 | 11/2006 |
| WO | WO 2007/000234 A1 | 1/2007 |
| WO | WO 2007/011619 A2 | 1/2007 |
| WO | WO 2007/056118 A1 | 5/2007 |
| WO | WO 2007/075794 A2 | 7/2007 |
| WO | WO 2007/095038 A2 | 8/2007 |
| WO | WO 2007/116025 A2 | 10/2007 |
| WO | WO 2007/130438 A2 | 11/2007 |
| WO | WO 2007/137187 A2 | 11/2007 |
| WO | WO 2007/139797 A2 | 12/2007 |
| WO | WO 2008/076143 A1 | 6/2008 |
| WO | WO 2008/076278 A2 | 6/2008 |
| WO | WO 2008/089087 A2 | 7/2008 |
| WO | WO 2008/093878 A1 | 8/2008 |
| WO | WO 2008/121467 A2 | 10/2008 |
| WO | WO 2008/127710 A2 | 10/2008 |
| WO | WO 2008/130910 A1 | 10/2008 |
| WO | WO 2009/036099 A1 | 3/2009 |
| WO | WO 2009/042613 A1 | 4/2009 |
| WO | WO 2009/052264 A2 | 4/2009 |
| WO | WO 2009/061349 A1 | 5/2009 |
| WO | WO 2009/105234 A2 | 8/2009 |
| WO | WO 2009/108637 A1 | 9/2009 |
| WO | WO 2009/111073 A2 | 9/2009 |
| WO | WO 2009/121031 A1 | 10/2009 |
| WO | WO 2009/126662 A1 | 10/2009 |
| WO | WO 2009/129545 A1 | 10/2009 |
| WO | WO 2009/129546 A1 | 10/2009 |
| WO | WO 2009/129548 A1 | 10/2009 |
| WO | WO 2009/146216 A2 | 12/2009 |
| WO | WO 2009/146218 A2 | 12/2009 |
| WO | WO 2009/151910 A2 | 12/2009 |
| WO | WO 2010/008744 A2 | 1/2010 |
| WO | WO 2010/011782 A1 | 1/2010 |
| WO | WO 2010/045318 A2 | 4/2010 |
| WO | WO 2010/048477 A2 | 4/2010 |
| WO | WO 2010/054051 A1 | 5/2010 |
| WO | WO 2010/085845 A1 | 8/2010 |
| WO | WO 2010/091140 A1 | 8/2010 |
| WO | WO 2010/098627 A2 | 9/2010 |
| WO | WO 2010/104406 A1 | 9/2010 |
| WO | WO 2010/117633 A1 | 10/2010 |
| WO | WO 2010/120861 A1 | 10/2010 |
| WO | WO 2010/124009 A2 | 10/2010 |
| WO | WO 2010/129053 A2 | 11/2010 |
| WO | WO 2011/002857 A2 | 1/2011 |
| WO | WO 2011/008053 A2 | 1/2011 |
| WO | WO 2011/008054 A2 | 1/2011 |
| WO | WO 2011/025267 A2 | 3/2011 |
| WO | WO 2011/025269 A2 | 3/2011 |
| WO | WO 2011/025271 A2 | 3/2011 |
| WO | WO 2011/025720 A1 | 3/2011 |
| WO | WO 2011/038467 A1 | 4/2011 |
| WO | WO 2011/056741 A2 | 5/2011 |
| WO | WO 2011/060206 A2 | 5/2011 |
| WO | WO 2011/069962 A1 | 6/2011 |
| WO | WO 2011/070499 A1 | 6/2011 |

OTHER PUBLICATIONS

"Vinorelbin." *Wikipedia: The Free Encyclopedia*. Wikimedia Foundation, Inc. Retrieved from the Internet on Jan. 28, 2013. URL:http://en.wikipedia.org/wiki/Vinorelbine.

Abbas et al., "A Drug Interaction Study to Evaluate the Effect of Ketoconazole on the Pharmacokinetics (PK) of Neratinib in Healthy Subjects," Clin. Pharmacol. Therapeutics 85:s44 (2009).

Abbas et al., "Evaluation of Neratinib (HKI-272) and Paclitaxel Pharmacokinetics (PK) in Asian and Caucasian Patients with Erbb2+ Breast Cancer: a Phase 1/2 Study of Neratinib in Combination with Paclitaxel," Ann. Oncol. 21:101 (2010).

Abbas et al., "Pharmacokinetics of Oral Neratinib During Co-Administration of Ketoconazole in Healthy Subjects," Br. J. Clin. Pharmacol. 71(4):522-527 (2011).

Abbas-Borhan et al., "A Clinical Study to Characterize the Occurrence of Mild-To-Moderate Diarrhea After Administration of Neratinib Either Once Daily or Twice Daily for 14 Days," EJC Suppl. 8:143 (2010).

Abbas-Borhan et al., "An Open-Label Study to Assess the Mass Balance and Metabolic Disposition of an Orally Administered Single Dose of 14C-Labeled Neratinib, an Irreversible pan-ErbB inhibitor, in Healthy Subjects," Drug Metab. Rev. 42:S1, 216 Abstr. P330 (2010).

Abrams et al., "Preclinical evaluation of the tyrosine kinase inhibitor SU11248 as a single agent and in combination with "standard of care" therapeutic agents for the treatment of breast cancer," Mol. Cancer Ther. 2(10):1011-1021 (2003).

Abramson and Arteaga, "New Strategies in HER2-Overexpressing Breast Cancer: Many Combinations of Targeted Drugs Available," Clin. Cancer Res. 17:952-958 (2011).

Adelaide et al., "Integrated Profiling of Basal and Luminal Breast Cancers," Cancer Res. 67(24):11565-11575 (2007).

Al-Dasooqi et al., "HER2 Targeted Therapies for Cancer and the Gastrointestinal Tract," Curr. Drug Targets 10(6):537-542 (2009).

Ali et al., "Mutational Spectra of PTEN/MMAC1 Gene: a Tumor Suppressor with Lipid Phosphatase Activity," J. Natl. Cancer Inst. 91(22):1922-1932 (1999).

Allegra et al., "American Society of Clinical Oncology Provisional Clinical Opinion: Testing for KRAS Gene Mutations in Patients With Metastatic Colorectal Carcinoma to Predict Response to Anti-Epidermal Growth Factor Receptor Monoclonal Antibody Therapy," J. Clin. Oncol. 27(12):2091-2096 (2009).

Allen et al., "Potential benefits of the irreversible pan-erbB inhibitor, CI-1033, in the treatment of breast cancer," Semin. Oncol. 29(3 Suppl 11):11-21 (2002).

Al-Muhammed et al., "In-Vivo Studies on Dexamethasone Sodium Phosphate Liposomes," J. Microencapsul. 13(3):293-306 (1996).

Alvarez et al., "Emerging Targeted Therapies for Breast Cancer," J. Clin. Oncol. 28(20):3366-3379 (2010).

Alvarez, "Present and Future Evolution of Advanced Breast Cancer Therapy," Breast Cancer Res. 12(Suppl 2):S1 (2010).

Amslinger, "The tunable functionality of alpha,beta-unsaturated carbonyl compounds enables their differential application in biological systems," ChemMedChem. 5(3):351-356 (2010).

Andre and Diniz, "Targeted regimes without cytotoxics—are they ready for prime time?" EJC Suppl. 7:49 Abst. 191 (2009).

Andre et al., "Everolimus for women with trastuzumab-resistant, HER2-positive, advanced breast cancer (BOLERO-3): a randomised, double-blind, placebo-controlled phase 3 trial," Lancet Oncol. 15(6):580-591 (2014) (Epub Apr. 14, 2014).

Anonymous, "Trastuzumab", Wikipedia, Retrieved from the Internet on Nov. 21, 2014. URL:http://en.wikipedia.org/wiki/Trastuzumab?oldid=634842165.

Anonymous: "Anticancer Agent—neratinib", Manufacturing Chemist, Dec. 2010/Jan. 2011, p. 27.

Anonymous: "Meeting Archives of Chemotherapy Foundation Symposium XXV, Nov. 7-10, 2007," The Chemotherapy Foundation, Nov. 8, 2007, Retrieved from the Internet on Jan. 13, 2010: URL:http://www.chemotherapyfoundationsymposium.org/meeting_archives/meetingarchives_tcf2007_main.html.

(56) References Cited

OTHER PUBLICATIONS

Arteaga, "ErbB-targeted therapeutic approaches in human cancer," Exp. Cell. Res. 284(1):122-130 (2003).
Avizienyte et al., "Comparison of the EGFR resistance mutation profiles generated by EGFR-targeted tyrosine kinase inhibitors and the impact of drug combinations," Biochem. J. 415(2):197-206 (2008).
Awada and Piccart-Gebhart, "Management of HER-2/Neu-Positive Metastatic Breast Cancer," Eur. J. Cancer (Suppl. 6):2-9 (2008).
Awada et al., "Safety and Efficacy of Neratinib (HKI-272) in Combination with Vinorelbine in ErbB2+ Metastatic Breast Cancer," Cancer Res. 69:24(Suppl 3) Abstr. 5095 (2009).
Awada et al., "Safety and Efficacy of Neratinib (HKI-272) in Combination with Vinorelbine in ErbB2+ Metastatic Breast Cancer (MBC)," Aim. Oncol. 21(Suppl. 4):iv62-iv63 Abstr. 145P (2010).
Awada et al., "Safety and efficacy of neratinib (HKI-272) plus vinorelbine in the treatment of patients with ErbB2-positive metastatic breast cancer pretreated with anti-HER2 therapy," Ann. Oncol. 24(1):109-116 (2013) (Epub Sep. 11, 2012).
Azria et al., "[Radiotherapy and inhibitors of epidermal growth factor receptor: preclinical findings and preliminary clinical trials]," Bull Cancer. 90 Spec No. S202-S212 (2003). (Abstract only).
Badache and Goncalves, "The ErbB2 signaling network as a target for breast cancer therapy," J. Mammary Gland Biol. Neoplasia 11(1):13-25 (2006).
Barton et al., "Predictive molecular markers of response to epidermal growth factor receptor(EGFR) family-targeted therapies," Curr. Cancer Drug Targets 10(8):799-812 (2010).
Baselga and Swain, "Novel anticancer targets: revisiting ERBB2 and discovering ERBB3," Nat. Rev. Cancer 9(7):463-475 (Epub Jun. 18, 2009).
Baselga et al., "Phase I safety, pharmacokinetic, and pharmacodynamic trial of ZD1839, a selective oral epidermal growth factor receptor tyrosine kinase inhibitor, in patients with five selected solid tumor types," J. Clin. Onc. 20(21):4292-4302 (2002).
Baselga, "Is there a role for the irreversible epidermal growth factor receptor inhibitor EKB-569 in the treatment of cancer? A mutation-driven question," J. Clin. Oncol. 24(15):2225-2226 (2006).
Baselga, "Novel agents in the era of targeted therapy: what have we learned and how has our practice changed?" Ann. Oncol. 19(Suppl 7):vii281-vii288 (2008).
Baselga, "Treatment of HER2-Overexpressing Breast Cancer," Ann. Oncol. (Suppl 7):vii36-vii40 (2010).
Bayes et al., "Gateways to clinical trials," Methods Find. Exp. Clin. Pharmacol. 28(9):657-678 (2006).
Bedard et al., "Beyond trastuzumab: overcoming resistance to targeted HER-2 therapy in breast cancer," Curr. Cancer Drug Targets 9(2):148-162 (2009).
Bedard et al., "Stemming resistance to HER-2 targeted therapy," J. Mammary Gland Biol. Neoplasia 14(1):55-66 (2009) (Epub Mar. 4, 2009).
Belani, "The role of irreversible EGFR inhibitors in the treatment of non-small cell lung cancer: overcoming resistance to reversible EGFR inhibitors," Cancer Invest. 28(4):413-423 (2010).
Bell and Haber, "A blood-based test for epidermal growth factor receptor mutations in lung cancer," Clin. Cancer Res. 12(13):3875-3877 (2006).
Berns et al., "A functional genetic approach identifies the PI3K pathway as a major determinant of trastuzumab resistance in breast cancer," Cancer Cell 12(4):395-402 (2007).
Berz and Wanebo, "Targeting the growth factors and angiogenesis pathways: small molecules in solid tumors," J. Surg. Oncol. 103(6):574-586 (2011).
Besse et al., "Neratinib (HKI-272), an irreversible pan-ErbB receptor tyrosine kinase inhibitor: preliminary results of a phase 2 trial in patients with advanced non-small cell lung cancer," Eur. J. Cancer (Suppl.):23 Abstr. 203 (2008).
Besse et al., "Targeted therapies in lung cancer," Ann. Oncol. 18(Suppl. 9):ix135-ix142 (2007).

Bettendorf et al., "Chromosomal imbalances, loss of heterozygosity, and immunohistochemical expression of TP53, RB1, and PTEN in intraductal cancer, intraepithelial neoplasia, and invasive adenocarcinoma of the prostate," Genes Chromosomes Cancer 47(7):565-572 (2008).
Bischoff and Ignatov, "The Role of Targeted Agents in the Treatment of Metastatic Breast Cancer," Breast Care (Basel) 5(3):134-141 (2010) (Epub Jun. 16, 2010).
Blanco-Aparicio et al., "PTEN, More Than the AKT Pathway," Carcinogenesis 28(7):1379-1386 (2007) (Epub Mar. 6, 2007).
Blanke, "Gefitinib in colorectal cancer: if wishes were horses," J. Clin. Oncol. 23(24):5446-5449 (2005).
Blencke et al., "Mutation of threonine 766 in the epidermal growth factor receptor reveals a hotspot for resistance formation against selective tyrosine kinase inhibitors," J. Biol. Chem. 278(17):15435-15440 (2003).(Epub Feb. 19, 2003).
Board et al., "Multiplexed assays for detection of mutations in PIK3CA," Clin. Chem 54(4):757-760 (2008).
Bonanno et al., "Mechanisms of acquired resistance to epidermal growth factor receptor tyrosine kinase inhibitors and new therapeutic perspectives in non small cell lung cancer," Curr. Drug Targets 12(6):922-933 (2011).
Boschelli et al., "Bosutinib: a review of preclinical studies in chronic myelogenous leukaemia," Eur. J. Cancer. 46(10):1781-1789 (2010).
Boschelli, "4-Anilino-3-quinolinecarbonitriles: An Emerging Class of Kinase Inhibitors—An Update," Med. Chem Rev. Online 1:457-463 (2004).
Bose and Ozer, "Neratinib: an oral, irreversible dual EGFR/HER2 inhibitor for breast and non-small cell lung cancer," Expert Opin. Investig. Drugs 18(11):1735-1751 (2009).
Bose et al., "Allelic loss of chromosome 10q23 is associated with tumor progression in breast carcinomas," Oncogene 17(1):123-127 (1998).
Bose et al., "Reduced expression of PTEN correlates with breast cancer progression," Hum. Pathol. 33(4):405-409 (2002).
Boyce et al., "Requirement of pp60c-src expression for osteoclasts to form ruffled borders and resorb bone in mice," J. Clin. Invest. 90(4):1622-1627 (1992).
Boyd et al., "Lapatanib: Oncolytic Dual EFGR and erbB-2 Inhibitor," Drugs Future 30(12):1225-1239 (2005).
Brackstone et al., "Canadian initiatives for locally advanced breast cancer research and treatment: inaugural meeting of the Canadian Consortium for LABC," Curr. Oncol. 18(3):139-144 (2011).
Bridges, "Current Progress Towards the Development of Tyrosine Kinase Inhibitors as Anticancer Agents," Expert Opin. Emerg. Drugs. 3:279-292 (1998).
Brittain, Harry G. (Eds), "Polymorphism in Pharmaceutical Solids", Chapters 1 and 5, Marcel Dekker, Inc., New York (1999).
Brook et al., "Management of transitional cell carcinoma by targeting the epidermal growth factor receptor," Therapy 3(3):407-416 (2006).
Browne et al., "HER-2 Signaling and Inhibition in Breast Cancer," Curr. Cancer Drug Targets 9(3):419-438 (2009).
Broxterman and Georgopapadakou, "Anticancer therapeutics: a surge of new developments increasingly target tumor and stroma," Drug Resist. Updat. 10(4-5):182-193 (2007) (Epub Sep. 12, 2007).
Buerger et al., "Allelic length of a CA dinucleotide repeat in the egfr gene correlates with the frequency of amplifications of this sequence—first results of an inter-ethnic breast cancer study," J. Pathol. 203(1):545-550 (2004).
Bullard Dunn et al., "Evolving Therapies and FAK Inhibitors for the Treatment of Cancer," Anticancer Agents Med. Chem. 10(10):722-734 (2010).
Burstein et al., "Gastrointestinal and Cardiovascular Safety Profiles of Neratinib Monotherapy in Patients with Advanced Erbb2-Positive Breast Cancer," Cancer Res. 69:Abst 5096 (2009).
Burstein et al., "HKI-272, an irreversible pan ErbB receptor tyrosine kinase inhibitor: preliminary phase 2 results in patients with advanced breast cancer," Breast Cancer Res. Treat. 106(Suppl. 1): 5268 Abstr. 6061 (2007).

(56) References Cited

OTHER PUBLICATIONS

Burstein et al., "Neratinib (HKI-272), an irreversible pan ErbB receptor tyrosine kinase inhibitor: phase 2 results in patients with advanced HER2+ breast cancer," Cancer Res. 69(2 Suppl.) Abstr. 37 (2008).

Burstein et al., "Neratinib, an irreversible ErbB receptor tyrosine kinase inhibitor, in patients with advanced ErbB2-positive breast cancer," J. Clin. Oncol. 28(8):1301-1307 (2010).

Burstein, "The Distinctive Nature of HER2-Positive Breast Cancers," N. Engl. J. Med. 353(16):1652-1654 (2005).

Byrn et al., "Pharmaceutical solids: a strategic approach to regulatory considerations," Pharm. Res. 12(7):945-954 (1995).

Callahan and Hurwitz, "Human epidermal growth factor receptor-2-positive breast cancer: Current management of early, advanced, and recurrent disease," Curr. Opin. Obstet. Gynecol. 23(1):37-43 (2011).

Camp et al., "Molecular mechanisms of resistance to therapies targeting the epidermal growth factor receptor," Clin. Cancer Res. 11(1):397-405 (2005).

Campas et al., "BIBW-2992. Dual EGFR/HER2 Inhibitor Oncolytic;Tovok ™," Drugs Future 33(8):649-654 (2008).

Campbel et al., "Gefitinib for the Treatment of Non-Small-Cell Lung Cancer," Expert Opin. Pharmacother. 11(8):1343-1357 (2010).

Cao et al., "Epidermal Growth Factor Receptor as a Target for Anti-Cancer Agent Design," Anticancer Agents Med. Chem. 10(6):491-503 (2010).

Cappuzzo et al., "Gefitinib in pretreated non-small-cell lung cancer (NSCLC): analysis of efficacy and correlation with HER2 and epidermal growth factor receptor expression in locally advanced or metastatic NSCLC," J. Clin. Oncol. 21(14):2658-2663 (2003).

Cappuzzo et al., "Surrogate predictive biomarkers for response to anti-EGFR agents: state of the art and challenges," Int. J. Biol. Markers 22(1 Suppl 4):S10-23 (2007).

Cardoso et al., "Locally Recurrent or Metastatic Breast Cancer: ESMO Clinical Practice Guidelines for Diagnosis, Treatment and Follow-Up," Ann. Oncol. 21(5):v15-v19 (2010).

Carney et al., "HER-2/neu diagnostics in breast cancer," Breast Cancer Res. 9(3):207 (2007).

Carter et al., "Small-Molecule Inhibitors of the Human Epidermal Receptor Family," Expert Opin. Investig. Drugs 18(12):1829-1842 (2009).

Cascone et al., "Epidermal Growth Factor Receptor Inhibitors in Non-Small-Cell Lung Cancer," Expert Opin. Drug Discov. 2(3):335-348 (2007).

Centre de Lutte Contre le Cancer Georges-Francois Leclerc (Fumoleau P. Study chair): "Lapatinib and Vinorelbine in Treating Women With HER2-Overexpressing Locally Advanced or Metastatic Breast Cancer" Clinical Trials Aug. 6, 2007 Retrieved from the Internet: URL:http://clinicaltrials.gov/ct2/show/NCT00513058?term=lapatinib+and+vinorelbine&rank=1 [retrieved on Jan. 13, 2010].

Chan and Giaccia, "Harnessing Synthetic Lethal Interactions in Anticancer Drug Discovery," Nat. Rev. Drug Discov. 10(5):351-364 (2011).

Chan et al., "Neratinib after trastuzumab-based adjuvant therapy in patients with HER2-positive breast cancer (ExteNET): a multicentre, randomised, double-blind, placebo-controlled, phase 3 trial," 17(3):367-377 (2016) (Epub Feb. 10, 2016).

Chan, "A review of the use of trastuzumab (Herceptin ®) plus vinorelbine in metastatic breast cancer," Ann. Oncol.18(7):1152-1158 (2007) (Epub Jan. 29, 2007) Review.

Chandrasekaran et al., "Reversible Covalent Binding of Neratinib to Human Serum Albumin in Vitro," Drug Metab. Lett. 4(4):220-227 (2010).

Chen et al., "Epidermal growth factor receptor inhibitors: current status and future directions," Curr. Probl. Cancer 33(4):245-294 (2009).

Chenoweth, "Can single-patient investigational new drug studies hurry slow trains to the fast track?" Drug Discov. Today 11(5-6):185-186 (2006).

Cheung and Paterson, "American Chemical Society—226th National Meeting. Pain and Oncology," Idrugs 6(10):935-936 (2003).

Chew, H. K. et al., EGFR Inhibition with Lapatinib in Combination with Vinorelbine: A Phase I Study, Chemotherapy Foundation Symposium XXV, Chemotherapy Foundation, 2007, [Retrieved on Aug. 30, H-25 (2013)], obtained from the Internet, URL, http://chemotherapyfoundationsymposium.org/CMS/2007-archives-main.

Chew, Helen K., MD (University of California, Davis): "Lapatinib and Vinorelbine in Treating Patients With Advanced Solid Tumors" ClinicalTrials, Oct. 18, 2006, Retrieved from the Internet: URL:http//clinicaltrials.gov/ct2/show/NCT00389922?term=lapatinib+and+vinorelnine&rank=2 [retrieved on Jan. 13, 2010].

Chien and Rugo, "The Cardiac Safety of Trastuzumab in the Treatment of Breast Cancer," Expert Opin. Drug Saf. 9(2):335-346 (2010).

Chirieac and Dacic, "Targeted Therapies in Lung Cancer," Surg. Pathol. Clin. 3(1):71-82 (2010).

Chmielecki et al. Selection for the EGFR T790M gatekeeper resistance mutation may vary among different small molecule EGFR TKIs [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 1774.

Cho et al., "Structure of the extracellular region of HER2 alone and in complex with the Herceptin Fab," Nature 421(6924):756-760 (2003).

Chonn et al., "Recent Advances in Liposomal Drug-Delivery Systems," Curr. Opin. Biotechnol. 6(6):698-708 (1995).

Choong et al., "Gefitinib response of erlotinib-refractory lung cancer involving meninges—role of EGFR mutation," Nat. Clin. Pract. Oncol. 3(1):50-57 (2006).

Chow et al., "Safety and efficacy of neratinib (HKI-272) in combination with paclitaxel in ErbB2+ metastatic breast cancer," Cancer Res. 69(24 Suppl):Abstr. 5081 (2009).

Chow et al., "Safety and efficacy of neratinib (HKI-272) in combination with paclitaxel in patients with solid tumors," J. Clin. Oncol. (Meeting Abstracts) 27(15S):3557 (2009).

Chow et al., "Safety and efficacy of neratinib (HKI-272) in combination with paclitaxel in ERBB2+ metastatic breast cancer (MBC)," Ann. Oncol. 21(Suppl 4):iv62 Abstr. 144P (2010).

Cicenas, "The Potential Role of the EGFR/ERBB2 Heterodimer in Breast Cancer," Expert Opin. Ther. Patents 17(6):607-616 (2007).

Clouser et al., "Biomarker Targets and Novel Therapeutics," Cancer Treat. Res. 149:85-105 (2009).

Cobleigh et al., "Multinational study of the efficacy and safety of humanized anti-HER2 monoclonal antibody in women who have HER2-overexpressing metastatic breast cancer that has progressed after chemotherapy for metastatic disease," J. Clin. Oncol. 17(9):2639-2648 (1999).

Cohen et al., "United States Food and Drug Administration Drug Approval summary: Gefitinib (ZD1839; Iressa) tablets," Clin. Cancer Res. 10(4):1212-1218 (2004).

Coldren et al., "Baseline gene expression predicts sensitivity to gefitinib in non-small cell lung cancer cell lines," Mol. Cancer Res. 4(8):521-528 (2006).

Collins et al., "Lapatinib: a competitor or companion to trastuzumab?" Cancer Treat. Rev. 35(7):574-581 (2009).

Colombo et al., "HER2 targeting as a two-sided strategy for breast cancer diagnosis and treatment: Outlook and recent implications in nanomedical approaches," Pharmacol. Res. 62(2):150-165 (2010) (Epub Feb. 1, 2010).

Conte et al., "Evolving nonendocrine therapeutic options for metastatic breast cancer: how adjuvant chemotherapy influences treatment," Clin. Breast Cancer 7(11):841-849 (2007).

Cooper and Cohen, "Mechanisms of resistance to EGFR inhibitors in head and neck cancer," Head Neck 31(8):1086-1094 (2009).

(56) References Cited

OTHER PUBLICATIONS

Correspondence from Chilean associate regarding a First Office Action issued in corresponding Chilean Patent Application No. 2961-2006 dated 2009-2010.
Correspondence from Israeli associate regarding a First Office Action issued in corresponding Israeli Patent Application No. 190805 dated 2010.
Correspondence from Peruvian associate regarding an Opposition filed against corresponding Peruvian Patent Application No. 001 342-2006/QIN in 2007.
Cortes-Funes et al., "Neratinib, An Irreversible Pan Erb Receptor Tyrosine Kinase Inhibitor Active for Advanced HER2+ Breast Cancer," Breast Cancer Res. 11 Suppl 1:S19 (2009).
Coughlin et al., "Approaches and limitations of phosphatidylinositol-3-kinase pathway activation status as a predictive biomarker in the clinical development of targeted therapy," Breast Cancer Res. Treat. 124(1):1-11 (2010) (Epub Aug. 28, 2010).
Cox, "Regression Models and Life Tables (With Discussion)," Journal of the Royal Statistical Society. Series B (Methodological), vol. 34, No. 2. (1972), pp. 187-220.
Da Cunha Santos et al., "EGFR Mutations and Lung Cancer," Am. Rev. Pathol. 6:49-69 (2011).
Damia and D'Incalci, "Contemporary pre-clinical development of anticancer agents—what are the optimal preclinical models?" Eur. J. Cancer 45(16):2768-2781 (2009) (Epub Sep. 15, 2009).
Dancey, "Epidermal growth factor receptor inhibitors in non-small cell lung cancer," Drugs 67(8):1125-1138 (2007).
Dang et al.,"The safety of dose-dense doxorubicin and cyclophosphamide followed by paclitaxel with trastuzumab in HER-2/neu overexpressed/amplified breast cancer," J. Clin. Oncol. 26(8):1216-1222 (2008).
Daniele and Sapino, "Anti-HER2 treatment and breast cancer: state of the art, recent patents, and new strategies," Recent Pat. Anticancer Drug Discov. 4(1):9-18 (2009).
Davidian, M. (2006) Introduction to statistical population modeling and analysis for pharmacokinetic data. Invited white paper for the International Workshop on Uncertainty and Variability in Physiologically Based Pharmacokinetic (PBPK) Models. Retrieved from the Internet: URL:http://www.epa.gov/ncct/uvpkm/files/Calibration_PreMeeting_Draft.pdf (89 pages) [Retrieved on Jan. 29, 2014].
Davidson, "HER2-Targeted Therapies: How Far We've Come—and Where We're Headed," Oncology (Williston Park) 25(5):425-426 (2011).
Davoli et al., "Progression and Treatment of HER2-Positive Breast Cancer," Cancer Chemother. Pharmacol. 65(4):611-623 (2010) (Epub Dec. 20, 2009).
De Bono and Rowinsky, "The ErbB receptor family: a therapeutic target for cancer," Trends Mol. Med. 8(4 Suppl):S19-S26 (2002).
De Luca and Normanno, "Predictive biomarkers to tyrosine kinase inhibitors for the epidermal growth factor receptor in non-small-cell lung cancer," Curr. Drug Targets 11(7):851-864 (2010).
De Maio et al., "Vinorelbine plus 3-weekly trastuzumab in metastatic breast cancer: a single-centre phase 2 trial," BMC Cancer. 7:50 (2007).
De Seranno and Meuwissen, "Progress and Applications of Mouse Models for Human Lung Cancer," Eur. Respir. J. 5(2):426-443 (2010).
Dempke and Heinemann, "Resistance to EGF-R (erbB-1) and VEGF-R modulating agents," Eur. J. Cancer 45(7):1117-1128 (2009) (Epub Jan. 3, 2009).
Depowski et al., "Loss of expression of the PTEN gene protein product is associated with poor outcome in breast cancer," Mod. Pathol. 14(7):672-676 (2001).
Di Cosimo and Baselga, "Management of breast cancer with targeted agents: importance of heterogeneity," Nat. Rev. Clin. Oncol. 7(3):139-147 (2010) (Epub Feb. 2, 2010).
Di Cosimo and Baselga, "Targeted Therapies in Breast Cancer: Where Are We Now?" Eur. J. Cancer 44(18):2781-2790 (2008) (Epub Nov. 14, 2008).
Di Maio et al., "New drugs in advanced non-small-cell lung cancer: searching for the correct clinical development," Expert Opin. Investig. Drugs 19(12):1503-1514 (2010) (Epub Nov. 4, 2010).
Dickler, "Updates on Therapeutic Approaches in HER2-Positive Disease," Clin. Adv. Hematol. Oncol. 8(2):105-107 (2010).
Dinh et al., "Trastuzumab for early breast cancer: current status and future directions," Clin. Adv. Hematol. Oncol. 5(9):707-717 (2007).
Dirix et al., "Neratinib Monotherapy in Patients with Advanced ERBB2-Positive Breast Cancer: Gastrointestinal and Cardiovascular Safety Profiles," Ann. Oncol. 21(Suppl 4):iv61-iv62 Abstr. 141P (2010).
Discafani et al., "Irreversible inhibition of epidermal growth factor receptor tyrosine kinase with in vivo activity by N-[4-[(3-bromophenyl)amino]-6-quinazolinyl]-2-butynamide (CL-387,785)," Biochem. Pharmacol. 57(8):917-925 (1999).
Doebele et al., "New strategies to overcome limitations of reversible EGFR tyrosine kinase inhibitor therapy in non-small cell lung cancer," Lung Cancer 69(1):1-12 (2010) (Epub Jan. 25, 2010).
Dorland's Illustrated Medical Dictionary. 3 1st ed. Philadelphia: Saunders Elsevier; c2007. Carcinoma; pp. 295-297.
Dowsett and Dunbier, "Emerging Biomarkers and New Understanding of Traditional Markers in Personalized Therapy for Breast Cancer," Clin. Cancer Res. 14(24):8019-8026 (2008).
Druker et al., "Efficacy and Safety of a Specific Inhibitor of the BCR-ABL Tyrosine Kinase in Chronic Myeloid Leukemia," N. Engl. J. Med. 344(14):1031-1037 (2001).
Eck and Yun, "Structural and Mechanistic Underpinnings of the Differential Drug Sensitivity of EGFR Mutations in Non-Small Cell Lung Cancer," Biochim. Biophys. Acta 1804(3):559-566 (2010).
Egloff and Grandis, "Targeting epidermal growth factor receptor and SRC pathways in head and neck cancer," Semin. Oncol. 35(3):286-297 (2008).
Eichhorn et al., "Phosphatidylinositol 3-kinase hyperactivation results in lapatinib resistance that is reversed by the mTOR/phosphatidylinositol 3-kinase inhibitor NVP-BEZ235," Cancer Res. 68(22):9221-9230 (2008).
Einhorn et al., "Summary Report 7th Annual Targeted Therapies of the Treatment of Lung Cancer," J. Thorac. Oncol. 3(5):545-555 (2008).
Einhorn, "Perspective on the Development of New Agents in Thoracic Cancers," Lung Cancer 50 Suppl 1: S27-S28 (2005).
Ellis and Crowder, "PIKing" the winner for phosphatidylinositol 3-kinase inhibitors in ErbB2-positive breast cancer: let's not "PTENed it's easy!" Clin. Cancer Res. 13(19):5661-5662 (2007).
Engelman and Settleman, "Acquired Resistance to Tyrosine Kinase Inhibitors During Cancer Therapy," Curr. Opin. Genet. Dev. 18(1):73-79 (2008) (Epub Mar. 5, 2008).
Engelman, "Targeting PI3K Signalling in Cancer: Opportunities, Challenges and Limitations," Nat. Rev. Cancer 9(8):550-562 (2009).
Engleman and Jänne, "Mechanisms of acquired resistance to epidermal growth factor receptor tyrosine kinase inhibitors in non-small cell lung cancer," Clin. Cancer Res. 14(10):2895-2899 (2008).
English Translation of an Opposition filed against corresponding Ecuador Patent Application No. SP-08-8423 in 2008.
Ercan et al., "Amplification of EGFR T790M causes resistance to an irreversible EGFR inhibitor," Oncogene. 29(16):2346-2356 (2010) (Epub Feb. 1, 2010).
Erjala et al., "Concomitant chemoirradiation with vinorelbine and gefitinib induces additive effect in head and neck squamous cell carcinoma cell lines in vitro," Radiother. Oncol. 85(1):138-145 (2007).
Esteva et al., "Molecular predictors of response to trastuzumab and lapatinib in breast cancer," Nat. Rev. Clin. Oncol. 7(2):98-107 (2010) (Epub Dec. 22, 2009).
Ettinger et al., "Antiemesis," J. Natl. Compr. Canc. Netw. 10(4):456-485 (2012).
Eyles et al., "Oral delivery and fate of poly(lactic acid) microsphere-encapsulated interferon in rats," J. Pharm. Pharmacol. 49(7):669-674 (1997).
Farley and Birrer, "Novel Therapeutic Targets," Cancer Treat. Res.149:63-84 (2009).

(56) References Cited

OTHER PUBLICATIONS

Felip et al., "Emerging Drugs for Non-Small-Cell Lung Cancer," Expert Opin. Emerg. Drugs 12(3):449-460 (2007).
Ferron et al., "Oral bioavailability of pantoprazole suspended in sodium bicarbonate solution," Am. J. Health Syst. Pharm. 60(13):1324-1329 (2003).
Ferté et al., "Molecular circuits of solid tumors: prognostic and predictive tools for bedside use," Nat. Rev. Clin. Oncol. 7(7):367-380 (2010) (Epub Jun. 15, 2010).
Firoozinia et al., "PIK3CA gene amplification and PI3K p110α protein expression in breast carcinoma," Int. J. Med. Sci. 11(6):620-625 (2014).
Fitch et al., "Genetics of dark skin in mice," Genes Dev. 17(2):214-228 (2003).
Fleming et al., "Nitrile-containing pharmaceuticals: efficacious roles of the nitrile pharmacophore," J. Med. Chem. 53(22)7902-7917 (2010) (Epub Aug. 30, 2010).
Fleming et al., "Phase II trial of temsirolimus in patients with metastatic breast cancer," Breast Cancer Res. Treat. 136(2):355-363 (2012) (Epub Jan. 13, 2012).
Folkman, "Angiogenesis in cancer, vascular, rheumatoid and other disease," Nat. Med. 1(1):27-31 (1995).
Frederick et al., "Epithelial to mesenchymal transition predicts gefitinib resistance in cell lines of head and neck squamous cell carcinoma and non-small cell lung carcinoma," Mol. Cancer Ther. 6(6):1683-1691 (2007) (Epub May 31, 2007).
Frü, "The search for improved systemic therapy of non-small cell lung cancer—what are today's options?" Lung Cancer 72(3):265-270 (2011) (Epub Apr. 14, 2011).
Fry, "Inhibition of the epidermal growth factor receptor family of tyrosine kinases as an approach to cancer chemotherapy: progression from reversible to irreversible inhibitors," Pharmacol. Ther. 82(2-3):207-218 (1999).
Fukuoka et al., "Multi-institutional randomized phase II trial of gefitinib for previously treated patients with advanced non-small-cell lung cancer (The IDEAL 1 Trial)," J. Clin. Oncol. 21(12):2237-2246 (2003) (Epub May 14, 2003).
Gadji et al., "EGF receptor inhibitors in the treatment of glioblastoma multiform: old clinical allies and newly emerging therapeutic concepts," Eur. J. Pharmacol. 625(1-3):23-30 (2009) (Epub Oct. 18, 2009).
Gajria and Chandarlapaty, "HER2-amplified breast cancer: mechanisms of trastuzumab resistance and novel targeted therapies," Expert Rev. Anticancer Ther. 11(2):263-275 (2011).
Gajria et al., "Tolerability and Efficacy of Targeting Both mTOR and HER2 Signaling in Trastuzumab-Refractory HER2+ Metastatic Breast Cancer," San Antonio Breast cancer Symposium. Abstract P5-18-04 (2010).
Gao et al., "Controlled Release of a Contraceptive Steroid From Biodegradable and Injectable Gel Formulations: in Vitro Evaluation," Pharm. Res. 12:857-863 (1995).
Garcia et al., "Promoter Methylation of the PTEN Gene Is a Common Molecular Change in Breast Cancer," Genes Chromosomes Cancer 41(2):117-127 (2004).
Garrett and Arteaga, "Resistance to HER2-directed antibodies and tyrosine kinase inhibitors: mechanisms and clinical implications," Cancer Biol. Ther. 11(9):793-800 (2011) (Epub May 1, 2011).
Gatzemeier, "Second-Generation EGFR Inhibitors and Combinations," J. Thorac Oncol. 4(9): S121 (2009).
Gazdar, "Activating and Resistance Mutations of EGFR in Non-Small-Cell Lung Cancer: Role in Clinical Response to EGFR Tyrosine Kinase Inhibitors," Oncogene 28:S24-S31 (2009).
Genentech, Herceptin ®—Product Literature, www.Genetech.Com, Sep. 1998 Revised (Jun. 2014), pp. 1-35.
Gennaro (Ed.), Remington's Pharmaceutical Sciences, 17th Edition, Alfonso R. Gennaro, Mack Publishing Company, Easton, PA (1985).
Geuna et al., "Hitting multiple targets in HER2-positive breast cancer: proof of principle or therapeutic opportunity?" Expert Opin. Pharmacother. 12(4):549-565 (2011) (Epub Jan. 6, 2011).

Geyer et al., "Lapatinib plus capecitabine for HER2-positive advanced breast cancer," N. Engl. J. Med. 355(26):2733-2743 (2006).
Ghayad and Cohen, "Inhibitors of the PI3K/Akt/mTOR pathway: new hope for breast cancer patients," Recent Pat. Anticancer Drug Discov. 5(1):29-57 (2010).
Giaccone et al., "Gefitinib in combination with gemcitabine and cisplatin in advanced non-small-cell lung cancer: a phase III trial—INTACT 1," J. Clin. Oncol. 22(5):777-784 (2004).
Giamas et al., "Kinases as Targets in the Treatment of Solid Tumors," Cell. Signal. 22(7):984-1002 (2010) (Epub Jan. 21, 2010).
Gilmer et al., "Impact of common epidermal growth factor receptor and HER2 variants on receptor activity and inhibition by lapatinib," Cancer Res. 68(2):571-579 (2008).
Glaxosmithkline, TYKERB Prescription Label, 2010, pp. 1-25.
Glück, "Chemotherapy Regimens in Metastatic Breast Cancer," Clin. Adv. Hematol. Oncol. 9(1)47-48 (2011).
Godin-Heymann et al., "Oncogenic activity of epidermal growth factor receptor kinase mutant alleles is enhanced by the T790M drug resistance mutation," Cancer Res. 67(15):7319-7326 (2007).
Godin-Heymann et al., "The T790M "gatekeeper" mutation in EGFR mediates resistance to low concentrations of an irreversible EGFR inhibitor," Mol. Cancer Ther. 7(4):874-879 (2008).
Goldhirsch et al., "2 years versus 1 year of adjuvant trastuzumab for HER2-positive breast cancer (HERA): an open-label, randomised control trail," Lancet 382:1021-1028 (2013).
Good, "A Comparison of Contact Angle Interpretations," J. Colloid Interface Sci. 44(1):63-71 (1973).
Govindan, "A review of epidermal growth factor receptor/HER2 inhibitors in the treatment of patients with non-small-cell lung cancer," Clin. Lung Cancer 11(1):8-12 (2010).
Greenberger et al., "EKB-569: a New Irreversible Inhibitor of Epidermal Growth Factor Receptor Tyrosine Kinase for the Treatment of Cancer," Clin. Cancer Res. 6(Suppl):4544s Abstr. 388 (2000).
Greulich et al., "Oncogenic Transformation by Inhibitor-Sensitive and -Resistant EGFR Mutants," PLOS Medicine 2(11) E313:1167-1176 (2005).
Gridelli et al., "Erlotinib in the Treatment of Non-small Cell Lung Cancer: Current Status and Future Developments," Anticancer Res. 30:1301-1310 (2010).
Grimm et al., "Diagnostic and Therapeutic Use of Membrane Proteins in Cancer Cells," Curr. Med. Chem. 18(2):176-190 (2011).
Guarneri et al., "Anti-HER2 neoadjuvant and adjuvant therapies in HER2 positive breast cancer," Cancer Treat. Rev. 36 Suppl 3:S62-S66 (2010).
Guertin et al., "Ablation in mice of the mTORC components raptor, rictor, or mLST8 reveals that mTORC2 is required for signaling to Akt-FOXO and PKCalpha, but not S6K1," Dev. Cell. 11(6):859-871 (2006).
Gullick et al., "Expression of epidermal growth factor receptors on human cervical, ovarian, and vulval carcinomas," Cancer Res. 46(1):285-292 (1986).
Hager et al., "PTEN expression in renal cell carcinoma and oncocytoma and prognosis," Pathology 39(5):482-485 (2007) (Abstract Only).
Hammerman et al., "Resistance to Epidermal Growth Factor Receptor Tyrosine Kinase Inhibitors in Non-Small Cell Lung Cancer," Clin. Cancer Res. 15(24):7502-7509 (2009).
Harris et al., "c-erbB-2 in serum of patients with breast cancer," Int. J. Biol. Markers 14(1):8-15 (1999).
Hasselblatt, "Ependymal Tumors," Recent Results Cancer Res. 171:51-66 (2009).
Hawkins and Grunberg, "Chemotherapy-Induced Nausea and Vomiting: Challenges and Opportunities for Improved Patient Outcomes," Clin. J. Oncol. Nurs. 13(1):54-64 (2009).
Hegedus et al., "Interaction of ABC multidrug transporters with anticancer protein kinase inhibitors: substrates and/or inhibitors?" Curr. Cancer Drug Targets 9(3):252-272 (2009).
Heigener and Reck, "Mutations in the epidermal growth factor receptor gene in non-small cell lung cancer: Impact on treatment beyond gefitinib and erlotinib," Adv. Ther. 28(2):126-133 (2011) (Epub Dec. 16, 2010).

(56) References Cited

OTHER PUBLICATIONS

Heigener, "Non-Small Cell Lung Cancer in Never-Smokers: a New Disease Entity?" Onkologie 34(4):202-207 (2011) (Epub Mar. 18, 2011).
Heist et al., "A phase II study of oxaliplatin, pemetrexed, and bevacizumab in previously treated advanced non-small cell lung cancer," J. Thorac. Oncol. 3(10):1153-1158 (2008).
Herbst et al., "Gefitinib in Combination with Paclitaxel and Carboplatin in Advanced Non-Small-Cell Lung Cancer: a Phase III Trial-INTACT 2," J. Clin. Oncol. 22(5):785-794 (2004).
Herbst et al., "Selective oral epidermal growth factor receptor tyrosine kinase inhibitor ZD1839 is generally well-tolerated and has activity in non-small-cell lung cancer and other solid tumors: results of a phase I trial," J. Clin. Oncol. 20(18):3815-3825 (2002).
Heymach et al., "Epidermal growth factor receptor inhibitors in development for the treatment of non-small cell lung cancer," Clin. Cancer Res. 12(14 Pt 2):4441s-4445s (2006).
Higa et al., "Biological considerations and clinical applications of new HER2-targeted agents," Expert Rev. Anticancer Ther. 10(9):1497-1509 (2010).
Ho and Laskin, "EGFR-directed therapies to treat non-small-cell lung cancer," Expert Opin. Investig. Drugs 18(8):1133-1145 (2009).
Holbro and Hynes, "ErbB receptors: directing key signaling networks throughout life," Annu. Rev. Pharmacol. Toxicol. 44:195-217 (2004).
Holodov and Yakovlev, Clinical Pharmacokinetics, Moscow, Medicine, (1985), pp. 83-98, 134-138, 160, 378-380 (English translation not available).
Hookes and Lakeram, "American Chemical Society—235th National Meeting. Part 2: EGFR kinase inhibitors and β3-lactamases under investigation by Wyeth" Idrugs 11(6):391-393 (2008).
Horn and Sandler, "Epidermal growth factor receptor inhibitors and antiangiogenic agents for the treatment of non-small cell lung cancer," Clin. Cancer Res. 15(16):5040-5048 (2009) (Epub Aug. 11, 2009).
Hou and Kumamoto, "Flavonoids as protein kinase inhibitors for cancer chemoprevention: direct binding and molecular modeling," Antioxid. Redox Signal 13(5):691-719 (2010).
Huang et al., "Up-regulation of miR-21 by HER2/neu signaling promotes cell invasion," J. Biol. Chem. 284(27):18515-18524 (2009) (Epub May 6, 2009).
Hubalek et al., "Resistance to HER2-targeted therapy: mechanisms of trastuzumab resistance and possible strategies to overcome unresponsiveness to treatment," Wien. Med. Wochenschr. 160(19-20):506-512 (2010) (Epub Oct. 26, 2010).
Huber et al., "Pharmacokinetics of pantoprazole in man," Int. J. Clin. Pharmacol. Ther. 34(5):185-194 (1996).
Hug et al., "A single-dose, crossover, placebo- and moxifloxacin-controlled study to assess the effects of neratinib (HKI-272) on cardiac repolarization in healthy adult subjects," Clin. Cancer Res. 16(15):4016-4023 (2010) (Epub Jul. 20, 2010).
Hung and Lau, "Basic Science of HER-2/neu: a review," Semin. Oncol. 26(4 Suppl 12):51-59 (1999).
Hungarian Intellectual Property Office Search Report for Hungarian Patent Application No. 201002712-6 (dated Aug. 4, 2011).
Hynes and Lane, "ERBB Receptors and Cancer: the Complexity of Targeted Inhibitors," Nat. Rev. Cancer 5(5):341-354 (2005).
ICH Expert Working Group: Impurities in New Drug Substances Q3A (R2), "International Conference on Harmonisation of Technical Requirements for Registration of Pharmaceuticals for Human Use" (Online) 2006.
ICH Expert Working Group: Impurities in New Drug Substances Q3A (R), "International Conference on Harmonisation of Technical Requirements for Registration of Pharmaceuticals for Human Use" (Online) 2002, XP002522324; URL http://www.ikev.org/haber/stabilite/cd/10%201.9%201CH%2OQ3AR%20forCD.pdf.
Ikediobi, "Somatic Pharmacogenomics in Cancer," Pharmacogenomics J. 8(5);305-314 (2008) (Epub Aug. 5, 2008).
Ikezoe et al., "Effect of SU11248 on gastrointestinal stromal tumor-T1 cells: enhancement of growth inhibition via inhibition of 3-kinase/Akt/mammalian target of rapamycin signaling," Cancer Sci. 97(9):945-951 (2006).
Ikezoe et al., "The Anti-Tumor Effects of SU11248, a Class III Receptor Tyrosine Kinase Inhibitor, Against a Variety of Human Hematological Malignancies," Blood (ASH Annual Meeting Abstracts) 106: Abstract 2795 (2005).
Ilango et al., "Investigation of Colon Specificity of Novel Polysaccharide-Okra Mucilage-Film Coated with Enteric Materials," Int. J. Pharma. Bio. Sci. 3(2):52-62 (2012).
Iliadis et al., "APIS: a software for model identification, simulation and dosage regimen calculations in clinical and experimental pharmacokinetics," Computer Methods Programs Biomed. 38(4):227-239 (1992).
Intellectual Property Office of Singapore Examination Report for Singapore Patent Application No. 2013046099 (dated Jan. 21, 2016).
Intellectual Property Office of Singapore Written Opinion for Singapore Patent Application No. 2013046099 (dated Jun. 4, 2015).
International Preliminary Report on Patentability Chapter 1 for International Application No. PCT/US2009/047643 dated Dec. 18, 2010.
International Search Report for International Application No. PCT/US2008/080130, dated Apr. 5, 2009.
International Search Report for International Patent Application No. PCT/US2009/047643, dated Jan. 28, 2010.
Isakoff and Baselga, "Trastuzumab-DM1: building a chemotherapy-free road in the treatment of human epidermal growth factor receptor 2-positive breast cancer," J. Clin. Oncol. 29(4):351-354 (2011) (Epub Dec. 20, 2010).
Ito et al., "A Phase 1 Study of Neratinib (HKI-272) in Combination with Paclitaxel in Japanese Patients with Solid Tumors," Ann. Oncol. 21 (Suppl 8):viii103 Abstr. 298P (2010).
Ito et al., "Tolerability and safety of oral neratinib (HKI-272) in Japanese patients with advanced solid tumors," J. Clin. Oncol. 27:(suppl; abstr. e14505) (2009).
Jackisch, "Challenges in the treatment of ErbB2 (HER2)-positive breast cancer," EJC Suppl. 6(5):7-14 (2008).
Jahanzeb et al., "Phase II trial of weekly vinorelbine and trastuzumab as first-line therapy in patients with HER2+ metastatic breast cancer," Oncologist 7(5):410-417 (2002).
Jallal et al., "A Src/Abl kinase inhibitor, SKI-606, blocks breast cancer invasion, growth, and metastasis in vitro and in vivo," Cancer Res. 67(4):1580-1588 (2007).
Janczuk and Bialopiotrowicz, "Surface Free-Energy Components of Liquids and Low Energy Solids and Contact Angles," J. Colloid Interface Sci. 127(1):189-204 (1989).
Jänne et al., "Phase I dose-escalation study of the pan-HER inhibitor, PF299804, in patients with advanced malignant solid tumors," Clin. Cancer Res. 17(5):1131-1139 (2011) (Epub Jan. 10, 2011).
Jänne, "Challenges of detecting EGFR T790M in gefitinib/erlotinib-resistant tumours," Lung Cancer 60 Suppl 2:S3-S9 (2008).
Jasper, "The Surface Tension of Pure Liquid Compounds," J. Phys. Chem. Ref. Data 1:841 (1972).
Jelliffe et al., "Adaptive control of drug dosage regimens: basic foundations, relevant issues, and clinical examples," Int. J. Biomed. Comput. 36(1-2):1-23 (1994).
Ji et al., "Epidermal growth factor receptor variant III mutations in lung tumorigenesis and sensitivity to tyrosine kinase inhibitors," Proc. Natl. Acad. Sci. U.S.A. 103(20):7817-7822 (2006) (Epub May 3, 2006).
Ji et al., "The impact of human EGFR kinase domain mutations on lung tumorigenesis and in vivo sensitivity to EGFR-targeted therapies," Cancer Cell. 9(6):485-495 (2006) (Epub May 25, 2006).
Jimeno and Hidalgo, "Pharmacogenomics of epidermal growth factor receptor (EGFR) tyrosine kinase inhibitors," Biochim. Biophys. Acta 1766(2):217-229 (2006) (Epub Sep. 12, 2006).
Johnson et al., "Cisplatin and Its Analogues," Cancer Principles & Practice of Oncology, 6th Edition, Ed. Devita, V.T., Hellman, S., Rosenberg, S.A, Lippincott Williams & Wilkins. Philadelphia, 2001, p. 376-388.

(56) References Cited

OTHER PUBLICATIONS

Johnson et al., "Impact of EGFR mutations on treatment of non-small cell lung cancer," Cancer Chemother. Pharmacol. 58(Suppl1): s5-s9 (2006).
Johnson et al., "Strategies for discovering and derisking covalent, irreversible enzyme inhibitors," Future Med. Chem. 2(6):949-964 (2010).
Johnson, "Biomarkers of Lung Cancer Response to EGFR-TKI," EJC Suppl. 5(8):14-15 Abstr. S23 (2007).
Johnson, "Protein kinase inhibitors: contributions from structure to clinical compounds," Q. Rev. Biophys. 42(1):1-40 (2009) (Epub Mar. 19, 2009).
Jones and Buzdar, "Evolving Novel Anti-HER2 Strategies," Lancet Oncol. 10(12):1179-1187 (2009).
Jones, "Adaptive trials receive boost," Nat. Rev. Drug Discov. 9(5):345-348 (2010) (Epub Apr. 23, 2010).
Jones, "HER4 intracellular domain (4ICD) activity in the developing mammary gland and breast cancer," J. Mammary Gland Biol. Neoplasia 13(2):247-258 (2008) (Epub May 13, 2008).
Jorissen et al., "Epidermal growth factor receptor: mechanisms of activation and signalling," Exp. Cell. Res. 284(1):31-53 (2003).
Joshi and Kucherlapati, "Pharmacogenomics of lung cancer: with a view to address EGFR-targeted therapies," Pharmacogenomics 8(9):1211-1220 (2007).
Kamath and Buolamwini, "Targeting EGFR and HER-2 receptor tyrosine kinases for cancer drug discovery and development," Med. Res. Rev. 26(5):569-594 (2006).
Kane, "Cancer Therapies Targeted to the Epidermal Growth Factor Receptor and Its Family Members," Expert Opin. Ther. Pat. 16(2):147-164 (2006).
Kaplan and Meier, "Nonparametric Estimation From Incomplete Observations," J. Am. Stat. Assoc. 53:457-481 (1958).
Katakami et al., "LUX-Lung 4: a phase II trial of afatinib in patients with advanced non-small-cell lung cancer who progressed during prior treatment with erlotinib, gefitinib, or both," J. Clin. Oncol. 31(27):3335-3341 (2013) (Epub Jul. 1, 2013).
Katzel et al., "Recent advances of novel targeted therapy in non-small cell lung cancer," J Hematol. Oncool. 2:2 (2009).
Kennedy et al., "Novel Agents in the Management of Lung Cancer," Curr. Med. Chem. 17(35):4291-4325 (2010).
Kim et al., "Chasing targets for EGFR tyrosine kinase inhibitors in non-small-cell lung cancer: Asian perspectives," Expert Rev. Mol. Diagn.7(6):821-836 (2007).
Kim et al., "The role of HER-2 oncoprotein in drug-sensitivity in breast cancer (Review)," Oncol. Rep. 9(1):3-9 (2002).
Klein and Levitzki, "Targeting the EGFR and the PKB Pathway in Cancer," Curr. Opin. Cell. Biol. 21(2):185-193 (2009) (Epub Feb. 11, 2009).
Klüter et al., "Characterization of irreversible kinase inhibitors by directly detecting covalent bond formation: a tool for dissecting kinase drug resistance," ChemBioChem 11(18):2557-2566 (2010).
Kobayashi et al., "EGFR mutation and resistance of non-small-cell lung cancer to gefitinib," N. Engl. J. Med. 352(8):786-792 (2005).
Kotteas et al., "Targeted therapy for nonsmall cell lung cancer: focusing on angiogenesis, the epidermal growth factor receptor and multikinase inhibitors," Anticancer Drugs 21(2):151-168 (2010).
Kris et al., "Efficacy of gefitinib, an inhibitor of the epidermal growth factor receptor tyrosine kinase, in symptomatic patients with non-small cell lung cancer: a randomized trial," JAMA 290(16):2149-2158 (2003).
Krop, "Managing Trastuzumab-resistant Breast Cancer," Clin. Adv. Hematol. Oncol. 7(2):108-110 (2009).
Kulke et al., "Capecitabine Plus Erlotinib in Gemcitabine-Refractory Advanced Pancreatic Cancer," J. Clin. Oncol. 25(30):4787-4792 (2007).
Kuznar, "New Small Molecule Added to Trastuzumab Improves Survival in Metastatic Disease," Am. Health. Drug. Benefits 2(5):27 (2009).
Kwak et al., "Irreversible inhibitors of the EGF receptor may circumvent acquired resistance to gefitinib," Proc. Natl. Acad. Sci. U.S.A. 102(21):7665-7670 (2005) (Epub May 16, 2005).
La Motta et al., "Computational studies of epidermal growth factor receptor: docking reliability, three-dimensional quantitative structure-activity relationship analysis, and virtual screening studies," J. Med. Chem. 52(4):964-975 (2009).
Laack et al., "Lessons learnt from gefitinib and erlotinib: Key insights into small-molecule EGFR-targeted kinase inhibitors in non-small cell lung cancer," Lung Cancer 69(3):259-264 (2010) (Epub Jun. 19, 2010).
Lam and Mok, "Targeted Therapy: An Evolving World of Lung Cancer," Respirology 16(1):13-21 (2011) (Epub Aug. 16, 2010).
Langdon et al., "Pertuzumab-Humanized anti-HER2 monoclonal antibody HER dimerization inhibitor oncolytic," Drugs Future 33(2):123-130 (2008).
Langer and Soria, "The role of anti-epidermal growth factor receptor and anti-vascular endothelial growth factor therapies in the treatment of non-small-cell lung cancer," Clin. Lung Cancer 11(2):82-90 (2010).
Langlois et al., "Application of a modification of the Polonovski reaction to the synthesis of vinblastine-type alkaloids," J. Am. Chem. Soc. 98(22):7017-7024 (1976).
Lapatinib and Vinorelbine in Treating Patients with Advanced Solid Tumors, clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00389922/2008_05_26.
Lapatinib and Vinorelbine in Treating Women With HER2-Overexpressing Locally Advanced or Metastatic Breast Cancer, http://clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00513058/2008_05_26.
Lee et al., "Lung Cancer in Never Smokers: Change of a Mindset in the Molecular Era," Lung Cancer 72(1):9-15 (2011) (Epub Jan. 26, 2011).
Lee et al., "Phase II Study of Vinorelbine Plus Trastuzumab in HER2 Overexpressing Metastatic Breast Cancer Pretreated with Anthracyclines and Taxanes," J. Breast Cancer 14(2):140-146 (2011).
Leone and Dudek, "Enzyme replacement therapy for Gaucher's disease in patient treated for non-small cell lung cancer," Anticancer Res. 28(6B):3937-3939 (2008).
Levitzki and Mishani, "Tyrphostins and other tyrosine kinase inhibitors," Annu. Rev. Biochem. 75:93-109 (2006).
Li and Perez-Soler, "Skin toxicities associated with epidermal growth factor receptor inhibitors," Target. Oncol. 4(2):107-119 (2009) (Epub May 19, 2009).
Li and Sun, "PTEN/MMAC1/TEP1 suppresses the tumorigenicity and induces G1 cell cycle arrest in human glioblastoma cells," Proc. Natl. Acad. Sci, U.S.A. 95(26):15406-15411 (1998).
Li and Sun, "TEP1, encoded by a candidate tumor suppressor locus, is a novel protein tyrosine phosphatase regulated by transforming growth factor β," Cancer Res. 57(11):2124-2129 (1997).
Li et al., "BIBW2992, an irreversible EGFR/HER2 inhibitor highly effective in preclinical lung cancer models," Oncogene 27(34):4702-4711 (2008) (Epub Apr. 14, 2008).
Li et al., "Bronchial and peripheral murine lung carcinomas induced by T790M-L858R mutant EGFR respond to HKI-272 and rapamycin combination therapy," Cancer Cell 12(1):81-93 (2007).
Li et al., "PTEN, a putative protein tyrosine phosphatase gene mutated in human brain, breast, and prostate cancer," Science 275(5308):1943-1947 (1997).
Ligibel and Winer, "Trastuzumab/chemotherapy combinations in metastatic breast cancer," Semin. Oncol. 29(3 Suppl 11):38-43 (2002).
Limentani et al., "Safety and Efficacy of Neratinib (HKI-272) in Combination with Vinorelbine in Patients with Solid Tumors," J. Clin. Oncol. (Meeting Abstracts) 27(15S):e14554 (2009).

(56) References Cited

OTHER PUBLICATIONS

Lin and Winer, "Chemotherapy agents in human epidermal growth factor receptor 2-positive breast cancer: time to step out of the limelight," J. Clin. Oncol. 29(3):251-253 (2011) (Epub Dec. 13, 2010).

Lin and Yang, "Epidermal growth factor receptor tyrosine kinase inhibitors in elderly or poor performance status patients with advanced non-small cell lung cancer," Target. Oncol. 4(1):37-44 (2009) (Epub Jan. 20, 2009).

Linardou et al., "Somatic EGFR mutations and efficacy of tyrosine kinase inhibitors in NSCLC," Nat. Rev. Clin. Oncol. 6(6):352-366 (2009).

Little, "Molecular Tests, Targets and Therapies for Cancer," EPC (DIA 43rd Annual Meeting Edition) p. 98 (2007).

Liu et al., "Targeting epidermal growth factor receptor in lung cancer: Perspective from the Asia-Pacific region," Asia-Pac. J. Clin. Oncol. 2:22-31 (2006).

Locker et al., "ASCO 2006 update of recommendations for the use of tumor markers in gastrointestinal cancer," J. Clin. Oncol. 24(33):5313-5327 (2006) (Epub Oct. 23, 2006).

Loew et al., "The epidermal growth factor receptor as a therapeutic target in glioblastoma multiforme and other malignant neoplasms," Anticancer Agents Med. Chem. 9(6):703-715 (2009).

Loke, "Drug-drug interactions—bridging the gulf between the bench and the bedside?" Br. J. Clin. Pharmacol. 71(4):485-486 (2011).

Lopiccolo et al., "Targeting the PI3K/Akt/mTOR pathway: effective combinations and clinical considerations," Drug Resist. Updat. 11(1-2):32-50 (2008) (Epub Dec. 31, 2007).

Loriot et al., "Drug insight: gastrointestinal and hepatic adverse effects of molecular-targeted agents in cancer therapy," Nat. Clin. Pract. Oncol. 5(5):268-278 (2008) (Epub Mar. 18, 2008).

Loriot et al., "Pemetrexed-induced pneumonitis: a case report," Clin. Lung Cancer 10(5):364-366 (2009).

Lorusso and Eder, "Therapeutic potential of novel selective-spectrum kinase inhibitors in oncology," Expert Opin. Investig. Drugs 17(7):1013-1028 (2008).

Lou et al., "Progress in Target Therapy for Breast Cancer," J. Oncology 15(9):788-795 (2009). (English Abstract).

Lu and Ku, "Preformulation stability study of the EGFR inhibitor HKI-272 (Neratinib) and mechanism of degradation," Drug Dev. Ind. Pharm. 1-7 (2011).

Lu et al., "The PTEN/MMAC1/TEP tumor suppressor gene decreases cell growth and induces apoptosis and anoikis in breast cancer cells," Oncogene 18(50):7034-7045 (1999).

Luetteke et al., "The mouse waved-2 phenotype results from a point mutation in the EGF receptor tyrosine kinase," Genes Dev. 8(4):399-413 (1994).

Lynch et al., "Activating mutations in the epidermal growth factor receptor underlying responsiveness of non-small-cell lung cancer to gefitinib," N. Engl. J. Med. 350(21):2129-2139 (2004) (Epub Apr. 29, 2004).

Lynch et al., "Novel Agents in the Treatment of Lung Cancer: Fourth Cambridge Conference," Clin. Cancer Res. 13(15 Suppl.):4583s-4588s (2007).

Lynch et al., "Summary statement novel agents in the treatment of lung cancer: Fifth Cambridge Conference assessing opportunities for combination therapy," J. Thorac. Oncol. 3(6 Suppl 2):S107-S112 (2008).

Lynch, "Molecular Staging of NSCLC: 2006," EJC (Suppl 4):24-25 Abstr. S55 (2006).

Ma et al., "PIK3CA as an oncogene in cervical cancer," Oncogene 19(23):2739-2744 (2000).

Macrinici and Romond, "Clinical updates on EGFR/HER targeted agents in early-stage breast cancer," Clin. Breast Cancer 10 Suppl 1:E38-E46 (2010).

Maehama et al., "A sensitive assay for phosphoinositide phosphatases," Anal. Biochem. 279(2):248-250 (2000).

Maehama et al., "PTEN and myotubularin: novel phosphoinositide phosphatases," Annu. Rev. Biochem. 70:247-279 (2001).

Maehama, "PTEN: its deregulation and tumorigenesis," Biol. Pharm. Bull, 30(9):1624-1627 (2007).

Mallon et al., "Antitumor efficacy of PKI-587, a highly potent dual PI3K/mTOR kinase inhibitor," Clin. Cancer Res. 17(10):3193-3203 (2011) (Epub Feb. 15, 2011).

Man et al., "New and established targets for the treatment of breast cancer," Adv. Breast Cancer 7(3):10-13 (2010).

Mangeney et al., "5'-Nor anhydrovinblastine : Prototype of a new class of vinblastine derivatives," Tetrahedron 35(18):2175-2179 (1979).

Mantel and Haenszel, "Statistical aspects of the analysis of data from retrospective studies of disease," J. Natl. Cancer Inst. 22(4):719-748 (1959).

Martinez-Garcia et al., "Tyrosine Kinase Inhibitors in Breast Cancer: Present Status and Perspectives," Cancer Chemother. Rev. 186-194 (2010).

Mattsson and Clowes, "Current concepts in restenosis following balloon angioplasty," Trends Cardiovasc. Med. 5(5):200-204 (1995).

Mauriz and Gonzalez-Gallego, "Antiangiogenic drugs: current knowledge and new approaches to cancer therapy," J. Pharm. Sci. 97(10):4129-4154 (2008).

Mayer, "Treatment of HER2-positive metastatic breast cancer following initial progression," Clin. Breast Cancer 9 Suppl 2:S50-S57 (2009).

McDermott et al., "Acquired resistance of non-small cell lung cancer cells to MET kinase inhibition is mediated by a switch to epidermal growth factor receptor dependency," Cancer Res. 70(4):1625-1634 (2010) (Epub Feb. 2, 2010).

McDermott et al., "High-throughput lung cancer cell line screening for genotype-correlated sensitivity to an EGFR kinase inhibitor," Methods Enzymol. 438:331-341 (2008).

McDermott et al., "Identification of genotype-correlated sensitivity to selective kinase inhibitors by using high-throughput tumor cell line profiling," Proc. Natl. Acad. Sci. U.S.A. 104(50):19936-19941 (2007) (Epub Dec. 6, 2007).

McNeil et al., "Two targets, one drug for new EGFR inhibitors," J. Natl. Cancer Inst. 98(16):1102-1103 (2006).

Mehta and Osipo, "Trastuzumab resistance: role for Notch signaling," ScientificWorldJournal 9:1438-1448 (2009).

Mendelsohn and Baselga, "The EGF receptor family as targets for cancer therapy," Oncogene 19(56):6550-6565 (2000).

Mendoza, "Targeted therapies in the treatment of advanced non-small-cell lung cancer: update," Klin Onkol. 22(4):131-138 (2009).

Meng et al., "MicroRNA-21 regulates expression of the PTEN tumor suppressor gene in human hepatocellular cancer," Gastroenterology 133(2):647-658 (2007) (Epub May 21, 2007).

Metro and Cappuzzo, "New targeted therapies for non-small-cell lung cancer," Therapy 6(3):335-350 (2009).

Metzger-Filho et al., "Management of metastatic HER2-positive breast cancer progression after adjuvant trastuzumab therapy—current evidence and future trends," Expert Opin. Investig. Drugs 19 Suppl 1:S31-S39 (2010).

Metzger-Filho et al., "Molecular targeted therapy in prevalent tumors: learning from the past and future perspectives," Current Clin. Pharmacol. 5(3):166-177 (2010).

Meyerhardt et al., "Phase II study of capecitabine, oxaliplatin, and erlotinib in previously treated patients with metastastic colorectal cancer," J. Clin. Oncol. 24(12):1892-1897 (2006).

Minami et al., "The major lung cancer-derived mutants of ERBB2 are oncogenic and are associated with sensitivity to the irreversible EGFR/ERBB2 inhibitor HKI-272," Oncogene 26(34):5023-5027 (2007) (Epub Feb. 19, 2007).

Minkovsky and Berezov, "BIBW-2992, a dual receptor tyrosine kinase inhibitor for the treatment of solid tumors," Curr. Opin. Investig. Drugs 9(12):1336-1346 (2008).

Mitsudomi et al., "Biological and clinical implications of EGFR mutations in lung cancer," Int. J. Clin. Oncol. 11(3):190-198 (2006).

Moasser, "Targeting the function of the HER2 oncogene in human cancer therapeutics," Oncogene 26(46):6577-6592 (2007) (Epub May 7, 2007).

Morabito et al., "Methodological Issues of Clinical Research with EGFR Inhibitors," Curr. Cancer Ther. Rev. 3(4):292-302 (2007).

(56) References Cited

OTHER PUBLICATIONS

Moreno-Aspitia and Perez, "Treatment options for breast cancer resistant to anthracycline and taxane," Mayo Clin. Proc. 84(6):533-545 (2009).
Morozova et al., "System-level analysis of neuroblastoma tumor-initiating cells implicates AURKB as a novel drug target for neuroblastoma," Clin. Cancer Res. 16(18):4572-4582 (2010) (Epub Jul. 22, 2010).
Morris and Hudis, "Personalizing therapy for metastatic breast cancer," Expert Rev. Anticancer Ther. 9(9):1223-1226 (2009).
Morrow et al., "Recent advances in systemic therapy: Advances in systemic therapy for HER2-positive metastatic breast cancer," Breast Cancer Res. 11(4):207 (2009) (Epub Jul. 15, 2009).
Mukai, "Targeted therapy in breast cancer: current status and future directions," Jpn. J. Clin. Oncol. 40(8):711-716 (2010) (Epub Apr. 8, 2010).
Mukai, "Treatment strategy for HER2-positive breast cancer," Int. J. Clin. Oncol. 15(4):335-340 (2010) (Epub Jul. 15, 2010).
Mukherji and Spicer, "Second-generation epidermal growth factor tyrosine kinase inhibitors in non-small cell lung cancer," Expert Opin. Investig. Drugs 18(3):293-301 (2009).
Mullard, "2010 in Reflection," Nat. Rev. Drug Discov. 10:7-9 (2011).
Munagala et al., "Promising molecular targeted therapies in breast cancer," Indian J. Pharmacol. 43(3):236-245 (2011).
Mundhenke et al., "Significance of Tyrosine Kinase Inhibitors in the Treatment of Metastatic Breast Cancer," Breast Care (Basel) 4(6):373-378 (2009) (Epub Nov. 16, 2009).
Murphy and Fornier, "HER2-positive breast cancer: beyond trastuzumab," Oncology (Williston Park) 24(5):410-415 (2010).
Muthuswamy, "Trastuzumab resistance: all roads lead to SRC," Nat. Med. 17(4):416-418 (2011).
Nagata et al., "PTEN activation contributes to tumor inhibition by trastuzumab, and loss of PTEN predicts trastuzumab resistance in patients," Cancer Cell vol. 6(2):117-127 (2004).
Nahta and O'Regan, "Evolving strategies for overcoming resistance to HER2-directed therapy: targeting the PI3K/Akt/mTOR pathway," Clin. Breast Cancer 10 Suppl 3:S72-S78 (2010).
Nakagawa et al., "Combined therapy with mutant-selective EGFR inhibitor and Met kinase inhibitor for overcoming erlotinib resistance in EGFR-mutant lung cancer," 11(10):2149-2157 (2012) (Epub Jul. 25, 2012).
Natoli et al., "Tyrosine kinase inhibitors," Curr. Cancer Drug Targets 10(5):462-483 (2010).
Nguyen et al., "Acquired resistance to epidermal growth factor receptor tyrosine kinase inhibitors in non-small-cell lung cancers dependent on the epidermal growth factor receptor pathway," Clin. Lung Cancer 10(4):281-289(2009).
Nicholson et al., "EGFR and cancer prognosis," Eur. J. Cancer 37 Suppl 4:S9-S15 (2001).
Nielsen et al., "HER2-targeted therapy in breast cancer. Monoclonal antibodies and tyrosine kinase inhibitors," Cancer Treat Rev. 35(2):121-136 (2009) (Epub Nov. 12, 2008).
Nitz, "Perspectives: Other ErbB2-Targeted Therapies," Breast Care (Basel) 5(s1):25-27 (2010) (Epub Apr. 26, 2010).
Nolé et al., "Dose-finding and pharmacokinetic study of an all-oral combination regimen of oral vinorelbine and capecitabine for patients with metastatic breast cancer," Ann. Oncol. 17(2):322-329 (2006) (Epub Nov. 22, 2005).
O'Brien et al., "Activated phosphoinositide 3-kinase/AKT signaling confers resistance to trastuzumab but not lapatinib," Mol. Cancer Ther. 9(6):1489-1502 (2010) (Epub May 25, 2010).
Ocaña and Amir, "Irreversible pan-ErbB tyrosine kinase inhibitors and breast cancer: current status and future directions," Cancer Treat. Rev. 35(8):685-691 (2009) (Epub Sep. 4, 2009).
Ocaña and Pandiella, "Identifying breast cancer druggable oncogenic alterations: lessons learned and future targeted options," Clin. Cancer Res. 14(4):961-970 (2008).
Ocaña et al., "New Targeted Therapies in Head and Neck Cancer," Cancer Chemo. Rev. 4:35-43 (2009).
Ocaña et al., "Novel tyrosine kinase inhibitors in the treatment of cancer," Curr. Drug Targets 10(6):575-576 (2009).
Ocaña et al., "Preclinical development of molecular-targeted agents for cancer," Nat. Rev. Clin Oncol. 8:200-209 (2011).
Office Action dated May 26, 2010 issued in corresponding European Patent Application No. 06836862.0.
Office Action dated Oct. 28, 2013 issued in corresponding Japanese Patent Application No. 2012-179873.
Office Action issued in corresponding Pakistan Patent Application No. 1456/2006 dated 2007.
Official Action and Search Report with English Translation, dated Jun. 18, 2013, for corresponding Chinese Application No. 201210328133.2.
Official Action dated Apr. 12, 2013 for corresponding Japanese Application No. 2010-258729 [with English translation].
Official Action dated Sep. 17, 2013 for corresponding Japanese Application No. 2011-289220 [with English translation].
Official Action from corresponding Japanese Application No. 2012-279650 dated Apr. 22, 2014 [with English Translation, received Jul. 16, 2014].
Oh et al., "Detection of epidermal growth factor receptor in the serum of patients with cervical carcinoma," Clin. Cancer Res. 6(12):4760-4763 (2000).
O'Hare et al., "Bcr-Abl kinase domain mutations and the unsettled problem of Bcr-AblT3151: looking into the future of controlling drug resistance in chronic myeloid leukemia," Clin. Lymphoma Myeloma 7 Suppl 3: S120-S130 (2007).
Okumura et al., "Induction of Noxa Sensitizes Human Colorectal Cancer Cells Expressing Mcl-1 to the Small-Molecule Bcl-2/Bcl-$x_L$ Inhibitor, ABT-737," Clin. Cancer Res. 14(24):8132-8142 (2008).
Omuro et al., "Lessons learned in the development of targeted therapy for malignant gliomas," Mol. Cancer Ther. 6(7):1909-1919 (2007).
O'Neil et al., (ed.). The Merck Index—An Encyclopedia of Chemicals, Drugs, and Biologicals. 13th Edition, Whitehouse Station, NJ: Merck and Co., Inc., 2001., p. 1454-1455.
Oshima, "Crystallization of Polymorphs and Pseudo-polymorphs and It's Control," Pham. Stage 6(10):48-53 (2007) [English translation not available].
Ostro and Cullis, "Use of liposomes as injectable-drug delivery systems," Am. J. Hosp. Pharm. 46(8):1576-1587 (1989).
Ouchi et al., "Antitumor activity of erlotinib in combination with capecitabine in human tumor xenograft models," Cancer Chemother. Pharmacol. 57(5):693-702 (2006).
Pal et al., "Targeted therapies for non-small cell lung cancer: an evolving landscape," Mol. Cancer Ther. 9(7):1931-1944 (2010) (Epub Jun. 22, 2010).
Pallis et al., "Targeted therapies in the treatment of advanced/metastatic NSCLC," Eur. J. Cancer 45(14):2473-2487 (2009).
Pantuck et al., "Prognostic relevance of the mTOR pathway in renal cell carcinoma: implications for molecular patient selection for targeted therapy," Cancer 109(11)2257-2267 (2007).
Pao and Chmielecki, "Rational, biologically based treatment of EGFR-mutant non-small-cell lung cancer," Nat. Rev. Cancer 10(11):760-774 (2010) (Epub Oct. 22, 2010).
Pao, "Defining clinically relevant molecular subsets of lung cancer," Cancer Chemother. Pharmacol. 58(Suppl 1):s11-s15 (2006).
Papaldo et al., "A phase II study on metastatic breast cancer patients treated with weekly vinorelbine with or without trastuzumab according to HER2 expression: changing the natural history of HER2-positive disease," Ann. Oncol. 17(4):630-636 (2006) (Epub Jan. 12, 2006).
Parideans et al., "Neratinib (HKI-272), an irreversible pan-ErbB receptor tyrosine kinase inhibitor: Phase 2 results in patients with ErbB2+ advanced breast cancer," Ann. Oncol. 20(Suppl 2):ii61-ii62 Abstr. 186P (2009).
Parkin and Fernández, "Use of statistics to assess the global burden of breast cancer," Breast J. 12(Suppl 1):S70-S80 (2006).
Pegram et al., "Expert roundtable: emerging questions in ErbB2-positive breast cancer; Feb. 22, 2007," Clin. Breast Cancer 8(Suppl 3):S131-S141 (2008).

(56) References Cited

OTHER PUBLICATIONS

Pegram et al., "The molecular and cellular biology of HER2/neu gene amplification/overexpression and the clinical development of herceptin (trastuzumab) therapy for breast cancer," Cancer Treat. Res. 103:57-75 (2000).
Perez et al., "Updated Results of the Combined Analysis of NCCTG N9831 and NSABP B-31 Adjuvant Chemotherapy With/Without Trastuzumab in Patients with HER2-Positive Breast Cancer," J. Clin. Oncol. ASCO Annual Meeting Proc. 25(18S):512 (2007).
Pérez-Soler, "Individualized therapy in non-small-cell lung cancer: future versus current clinical practice," Oncogene 28(Suppl 1):S38-S45 (2009).
Pérez-Tenorio et al., "PIK3CA mutations and PTEN loss correlate with similar prognostic factors and are not mutually exclusive in breast cancer," Clin. Cancer Res. 13(12):3577-3584 (2007).
Perren et al., "Immunohistochemical evidence of loss of PTEN expression in primary ductal adenocarcinomas of the breast," Am. J. Pathol. 155(4):1253-1260 (1999).
Petter et al., "A novel small-molecule drug platform to silence cancer targets- application to the panErbB kinases," In: Proceedings of the 100th Annual Meeting of the American Association for Cancer Research; Apr. 18-22, 2009; Denver, CO. Abstr. 3746 (2009).
Pfister et al., "American Society of Clinical Oncology Clinical Practice Guideline for the Use of Larynx-Preservation Strategies in the Treatment of Laryngeal Cancer," J. Clin. Oncol. 24(22):3693-3704 (2006) (Epub Jul. 10, 2006).
Piccart et al., "Beyond trastuzumab: new anti-HER2 agents," Breast 20(Suppl 1):S1-S2 Abstr. S02 (2011).
Piccart, "Circumventing de novo and acquired resistance to trastuzumab: new hope for the care of ErbB2-positive breast cancer," Clin. Breast Cancer 8(Suppl 3): S100-S113 (2008).
Plati et al., "Dysregulation of apoptotic signaling in cancer: molecular mechanisms and therapeutic opportunities," J. Cell. Biochem. 104(4):1124-1149 (2008).
Plosker and Keam, "Trastuzumab: a review of its use in the management of HER2-positive metastatic and early-stage breast cancer," Drugs 66(4):449-475 (2006).
Ponz-Sarvisé et al., "Epidermal growth factor receptor inhibitors in colorectal cancer treatment: what's new?" World J. Gastroenterol. 13(44):5877-5887 (2007).
Potashman and Duggan, "Covalent modifiers: an orthogonal approach to drug design," J. Med. Chem. 52(5):1231-1246 (2009).
Rabindran et al., "Antitumor activity of HKI-272, an orally active, irreversible inhibitor of the HER-2 tyrosine kinase," Cancer Res. 64(11):3958-3965 (2004).
Rabindran, "Antitumor activity of HER-2 inhibitors," Cancer Lett. 227(1):9-23 (2005) (Epub Dec. 15, 2004).
Raines and Ross, "Multiple growth factors are associated with lesions of atherosclerosis: specificity or redundancy?" Bioessays 18(4):271-282 (1996).
Rampaul et al., "Clinical value of epidermal growth factor receptor expression in primary breast cancer," Adv. Anat. Pathol. 12(5):271-273 (2005).
Rana and Swaby, "Targeted Therapies for HER2 Breast Cancer: A View of the Landscape," Curr. Breast Cancer Rep. 3:55-62 (2011).
Ranganathan and Muneer, "Highlights from: The 24th Annual Meeting of the American Association for Cancer Research; Los Angeles, CA; Apr. 14-18, 2007," Clin. Lung Cancer 8(6):359-363 (2007).
Rao, "Recent developments of collagen-based materials for medical applications and drug delivery systems," J. Biomater Sci. Polym. Ed. 7(7):623-645 (1995).
Ray et al., "Lung cancer therapeutics that target signaling pathways: an update," Expert Rev. Respir. Med. 4(5):631-645 (2010).
Ray et al., "The role of EGFR inhibition in the treatment of non-small cell lung cancer," Oncologist 14(11):1116-1130 (2009) (Epub Nov. 5, 2009).
Redon et al., "A simple specific pattern of chromosomal aberrations at early stages of head and neck squamous cell carcinomas: PIK3CA but not p63 gene as a likely target of 3q26-qter gains," Cancer Res. 61(10):4122-4129.
Reid et al., "Dual inhibition of ErbB1 (EGFR/HER1) and ErbB2 (HER2/neu)," Eur. J. Cancer 43(3):481-489 (2007) (Epub Jan. 8, 2007).
Response filed by Applicant on Apr. 30, 2009 to Office Action dated Jul. 18, 2008, in corresponding European Patent Application No. 06836862.0.
Rewcastle et al., "Synthesis of 4-(phenylamino)pyrimidine derivatives as ATP-competitive protein kinase inhibitors with potential for cancer chemotherapy," Curr. Org. Chem. 4(7):679-706 (2000).
Rexer et al., "Overcoming resistance to tyrosine kinase inhibitors: lessons learned from cancer cells treated with EGFR antagonists," Cell Cycle 8(1):18-22 (2009) (Epub Jan. 30, 2009).
Rich et al., "Phase II trial of gefitinib in recurrent glioblastoma," J. Clin. Oncol. 22(1):133-142 (2004) (Epub Nov. 24, 2003).
Riely et al., "Update on epidermal growth factor receptor mutations in non-small cell lung cancer," Clin. Cancer. Res. 12(24):7232-7241 (2006).
Riely, "Second-generation epidermal growth factor receptor tyrosine kinase inhibitors in non-small cell lung cancer," J. Thorac. Oncol. 3(6 Suppl 2): S146-S149 (2008).
Rosell et al., "Age-related genetic abnormalities: the Achilles' heel for customizing therapy in elderly lung cancer patients," Personalized Medicine 4(1):59-72 (2007).
Rosell et al., "Screening for epidermal growth factor receptor mutations in lung cancer," N. Engl. J. Med. 361(10):958-967 (2009) (Epub Aug. 19, 2009).
Rosell et al., "Treatment of non-small-cell lung cancer and pharmacogenomics: where we are and where we are going," Curr. Opin. Oncol. 18(2):135-143 (2006).
Rosen et al., "Targeting signal transduction pathways in metastatic breast cancer: a comprehensive review,"Oncologist 15(3):216-235 (2010) (Epub Mar. 3, 2010).
Ross et al., "The HER-2 receptor and breast cancer: ten years of targeted anti-HER-2 therapy and personalized medicine," Oncologist 14:320-368 (2009).
Rotella, "Medicinal Chemistry—XXth International Symposium. Lead finding strategies and kinase selectivity," IDrugs 11(11):774-778 (2008).
Roukos, "Trastuzumab and beyond: sequencing cancer genomes and predicting molecular networks," Pharmacogenomics J. 11(2):81-92 (2011) (Epub Oct. 26, 2010).
Roy and Perez, "Beyond trastuzumab: small molecule tyrosine kinase inhibitors in HER-2-positive breast cancer," Oncologist 14(11):1061-1069 (2009) (Epub Nov. 3, 2009).
Rubin et al., "10q23.3 loss of heterozygosity is higher in lymph node-positive (pT2-3,N+) versus lymph node-negative (pT2-3,N0) prostate cancer," Hum. Pathol. 31(4):504-508 (2000).
Rudloff and Samuels, "A growing family: adding mutated Erbb4 as a novel cancer target," Cell Cycle. 9(8):1487-1503 (2010) (Epub Apr. 15, 2010).
Saal et al., "PIK3CA mutations correlate with hormone receptors, node metastasis, and ERBB2, and are mutually exclusive with PTEN loss in human breast carcinoma," Cancer Res. 65(7):2554-2559 (2005).
Sakamoto et al., "Su-11248 Sugen," Curr. Opin. Investig. Drugs 5(12):1329-1339 (2004).
Salvesen et al., "Integrated genomic profiling of endometrial carcinoma associates aggressive tumors with indicators of PI3 kinase activation," Proc. Natl. Acad. Sci. U.S.A. 106(12):4834-4839 (2009) (Epub Mar. 4, 2009).
Samuels and Ericson, "Oncogenic PI3K and its role in cancer," Curr. Opin. Oncol. 18(1):77-82 (2006).
Sanchez-Martin and Pandiella, "Differential action of ErbB kinase inhibitors on receptor oligomerization," EJC Suppl. 8:107 Abstr. 337 (2010).
Santarpia et al., "Tyrosine kinase inhibitors for non-small-cell lung cancer: finding patients who will be responsive," Expert Rev. Respir. Med. (3):413-424 (2011).

(56) References Cited

OTHER PUBLICATIONS

Sartore-Bianchi et al., "Rationale and clinical results of multi-target treatments in oncology," Int. J. Biol. Markers 22(1 Suppl 4):S77-S87 (2007).
Sathornsumetee et al., "Malignant glioma drug discovery—targeting protein kinases," Expert Opin. Drug Discov. 2(1):1-17 (2007).
Sattler et al., "EGFR-targeted therapeutics: focus on SCCHN and NSCLC," ScientificWorldJournal 8:909-919 (2008).
Saura et al., (Dec. 2011). Safety and Efficacy of Neratinib in Combination with Capecitabine in Patients with ErbB2-Positive Breast Cancer. Poster presented at the 2011 CTRC-AACR San Antonio Breast Cancer Symposium, San Antonio, Texas.
Saura et al., "Safety of Neratinib (HKI-272) in Combination with Capecitabine in Patients with Solid Tumors: A Phase 1/2 Study," Cancer Res. 69(24 Suppl) Abstr. 5108 (2009).
Saura et al., "The safety of Neratinib (HKI-272) in Combination with Capecitabine in Patients with Solid Tumors: A Phase 1/2 Study," Ann. Oncol. 21(Suppl 4):iv63 Abstr. 147P (2010).
Scaltriti et al., "Expression of p95HER2, a truncated form of the HER2 receptor, and response to anti-HER2 therapies in breast cancer," J. Natl. Cancer Inst. 99(8):628-638 (2007).
Schiller et al., "Comparison of four chemotherapy regimens for advanced non-small-cell lung cancer," N. Engl. J. Med. 346(2):92-98 (2002).
Scott and Salgia, "Biomarkers in lung cancer: from early detection to novel therapeutics and decision making," Biomark. Med. 2(6):577-586 (2008).
Sebastian et al., "The complexity of targeting EGFR signalling in cancer: from expression to turnover," Biochim. Biophys. Acta. 1766(1):120-139 (2006) (Epub Jun. 23, 2006).
Sequist and Dziadziuszko, "Update on epidermal growth factor receptor inhibitor development in lung cancer," J. Thorac. Oncol. 1(7):740-743 (2006).
Sequist et al., "Neratinib, an irreversible pan-ErbB receptor tyrosine kinase inhibitor: results of a phase II trial in patients with advanced non-small-cell lung cancer," J. Clin. Oncol. 28(18):3076-3083 (2010) (Epub May 17, 2010).
Sequist, "Second-generation epidermal growth factor receptor tyrosine kinase inhibitors in non-small cell lung cancer," Oncologist 12(3):325-330 (2007).
Settleman and Kurie, "Drugging the bad "AKT-TOR" to overcome TKI-resistant lung cancer," Cancer Cell 12(1):6-8 (2007).
Seyhan et al., "A genome-wide RNAi screen identifies novel targets of neratinib sensitivity leading to neratinib and paclitaxel combination drug treatments," Mol. Biosyst. 7(6):1974-1989 (2011) (Epub Apr. 12, 2011).
Sharma and Jayanth, "Neratinib, an irreversible erbB receptor tyrosine Kinase inhibitor, in patients with advanced erbB2-positive breast cancer," [commentary] Adv. Breast Cancer 7(1):21 (2010).
Sharma and Settleman, "Oncogene addiction: setting the stage for molecularly targeted cancer therapy," Genes Dev. 21(24):3214-3231 (2007).
Sharma et al., "Epidermal growth factor receptor mutations in lung cancer," Nat. Rev. Cancer 7(3):169-181 (2007).
Sharma et al., "Receptor tyrosine kinase inhibitors as potent weapons in war against cancers," Curr. Pharm. Des. 15(7):758-776 (2009).
Shaw et al., "Pharmacological Inhibition of Restenosis: Learning From Experience," Trends Pharmacol. Sci. 16(12):401-404 (1995).
Shawver et al., "Receptor Tyrosine Kinases as Targets for Inhibition of Angiogenesis," Drug Discov. Today 2(2):50-63 (1997).
Shayesteh et al., "PIK3CA is implicated as an oncogene in ovarian cancer," Nat. Genet. 21(1):99-102 (1999).
Shimamura and Shapiro, "Heat shock protein 90 inhibition in lung cancer," J. Thorac. Oncol. 3(6 Suppl 2):S152-S159 (2008).
Shimamura et al., "Hsp90 inhibition suppresses mutant EGFR-T790M signaling and overcomes kinase inhibitor resistance," Cancer Res. 68(14):5827-5838 (2008).
Shimamura et al., "On-small-cell lung cancer and Ba/F3 transformed cells harboring the ERBB2 G776insV_G/C mutation are sensitive to the dual-specific epidermal growth factor receptor and ERBB2 inhibitor HKI-272," Cancer Res. 66(13):6487-6491 (2006).
Sibilia et al., "The epidermal growth factor receptor: from development to tumorigenesis," Differentiation 75(9):770-787 (2007).
Sigal, "Basic science for the clinician 48: tyrosine kinases in disease: the potential for inhibitors in the treatment of immunologic diseases," J. Clin. Rheumatol. 14(1):45-48 (2008).
Simon et al., "By 1023/SK&F 96022: biochemistry of a novel (H+ + K+)-ATPase inhibitor," Biochem Pharmacol. 39(11):1799-1806 (1990).
Singh et al., "Targeted covalent drugs of the kinase family," Curr. Opin. Chem. Biol. 14(4):475-480 (2010) (Epub Jul. 6, 2010).
Singh et al., "The resurgence of covalent drugs," Nat. Rev. Drug Discov. 10(4):307-317 (2011).
Slamon et al., "BCIRG 006: 2nd interim analysis phase III randomized trial comparing doxorubicin and cyclophosphamide followed by docetaxel (AC-T) with doxorubicin and cyclophosphamide followed by docetaxel and trastuzumab (AC-TH) with docetaxel, carboplatin and trastuzumab (TCH) in Her2neu positive early breast cancer patients," In: *San Antonio breast cancer symposium*; 2006 [abstract 52].
Slamon et al., "Human breast cancer: correlation of relapse and survival with amplification of the HER-2/neu oncogene," Science 235(4785):177-182 (1987).
Smith et al. "2006 update of recommendations for the use of white blood cell growth factors: an evidence-based clinical practice guideline," J. Clin. Oncol. 24(19):3187-3205 (2006) (Epub May 8, 2006).
Smith et al., "2-year follow-up of trastuzumab after adjuvant chemotherapy in HER2-positive breast cancer: a randomised controlled trial." Lancet 369(9555):29-36 (2007).
Smith, "Goals of Treatment of Patients with Metastatic Breast Cancer," Semin. Oncol. 33: S2-S5 (2006).
Solca et al., "Beyond Trastuzumab: Second-Generation Targeted Therapies for HER-2-Positive Breast Cancer," Drugs for HER-2-positive Breast Cancer, Milestones in Drug Therapy, 2011 p. 91-107 (2011).
Specht and Gralow, "Neoadjuvant chemotherapy for locally advanced breast cancer," Semin. Radiat. Oncol. 9(4):222-228 (2009).
Spector et al., "Small Molecule HER-2 Tyrosine Kinase Inhibitors," Breast Cancer Res. 9(2):205 (2007).
Spector, "Treatment of metastatic ErbB2-positive breast cancer: options after progression on trastuzumab," Clin. Breast Cancer 8 Suppl 3:S94-S99 (2008).
Spicer and Rudman, "EGFR inhibitors in non-small cell lung cancer (NSCLC): the emerging role of the dual irreversible EGFR/HER2 inhibitor BIBW 2992," Target Oncol. 5(4):245-255 (2010) (Epub Jun. 24, 2010).
Srivastava et al., "Synthesis and structure-activity relationships of potent antitumor active quinoline and naphthyridine derivatives," Anticancer Agents Med. Chem. 7(6):685-709 (2007).
Staroslawska et al. (Dec. 200). Safety and Efficacy of Neratinib (HKI-272) Plus Vinorelbine in the Treatment of Patients With ErbB2+ Metastatic Breast Cancer Pretreated With Anti-Her2 Therapy. Poster presented at teh 33rd Annual San Antonio Breast Cancer Symposium, San Antonio, Texas.
State Intellectual Property Office of the People's Republic of China Search Report for Chinese Patent Application No. 201210069340.0 (dated Dec. 11, 2015).
State Intellectual Property Office of the People's Republic of China Office Action for Chinese Patent Application No. 201210069340.0 (dated Dec. 21, 2015).
Stebbing et al., "Lemur tyrosine kinase-3 (LMTK3) in cancer and evolution," Oncotarget 2(6):428-429 (2011).
Steck et al., "Identification of a candidate tumour suppressor gene, MMAC1, at chromosome 10q23.3 that is mutated in multiple advanced cancers," Nat. Genet. 15(4):356-362 (1997).
Steins et al., "Targeting the epidermal growth factor receptor in non-small cell lung cancer," Onkologie 33(12):704-709 (2010) (Epub Nov. 26, 2010).

(56) References Cited

OTHER PUBLICATIONS

Stemke-Hale et al., "An integrative genomic and proteomic analysis of PIK3CA, PTEN, and AKT mutations in breast cancer," Cancer Res. 68(15):6084-6091 (2008).
Stockler et al., "Chemotherapy for advanced breast cancer—how long should it continue?" Breast Cancer Res. Treat. 81(Suppl. 1):S49-S52 (2003).
Stokoe et al., "Dual role of phosphatidylinositol-3,4,5-trisphosphate in the activation of protein kinase B," Science 277(5325):567-570 (1997).
Sugiyama, "Drug Transporters: Roles in New Drug Discovery and Development," Drug Metab. Rev. 42(S1):1-323 (2010).
Suzuki et al., "Combination of trastuzumab and vinorelbine in metastatic breast cancer," Jpn. J. Clin. Oncol. 33(10):514-517 (2003).
Swaby et al., "Neratinib in combination with trastuzumab for the treatment of advanced breast cancer: a phase I/II study," J. Clin. Oncol. 27:15s(suppl; abstr 1004) (2009).
Tagliabue et al., "HER2 as a target for breast cancer therapy," Expert Opin. Biol. Ther. 10(5):711-724 (2010).
Takada, "API form screening and selection in drug discovery stage," Pharm. Stage 6(10):20-27 (2007) [English translation not available].
Tejpar et al., "Phase 1/2a study of EKB-569, an irreversible inhibitor of epidermal growth factor receptor, in combination with 5-fluorouracil, leucovorin, and oxaliplatin (FOLFOX-4) in patients with advanced colorectal cancer (CRC)," J. Clin. Oncol. 22(14S):264s Abstr. 3579 (2004).
Test Procedures and Acceptance Criteria for New Drug Substances and New Drug Products; Pharmaceutical Affairs Bureau Notification No. 568; 2001 [English translation not available].
Therasse et al., "New guidelines to evaluate the response to treatment in solid tumors. European Organization for Research and Treatment of Cancer, National Cancer Institute of the United States, National Cancer Institute of Canada," J. Natl. Cancer Inst. 92(3):205-216 (2000).
Tjin Tham Sjin et al., "Design of a novel covalent EGFR mutant-selective inhibitor," EJC Suppl. 8(7):31 Abstr. 73 (2010).
Toffoli et al., "Pharmacology of epidermal growth factor inhibitors," Int. J. Biol. Markers 22(1 Suppl 4):S24-S39 (2007).
Tolaney and Krop, "Mechanisms of trastuzumab resistance in breast cancer," Anticancer Agents Med. Chem. 9(3):348-355 (2009).
Tolaney et al., "HER2-Positive Breast Cancer," JCOM 14(7):395-403 (2007).
Tomillero and Moral, "Gateways to Clinical Trials," Methods Find. Exp. Clin. Pharmacol. 31(3):183-226 (2009).
Tomillero and Moral, "Gateways to Clinical Trials," Methods Find. Exp. Clin. Pharmacol. 31(10):661-700 (2009).
Tookman and Roylance, "New Drugs for Breast Cancer," Br. Med. Bull. 96:111-129 (2010) (Epub Sep. 23, 2010).
Torres and Harris, "Polycystic kidney disease: genes, proteins, animal models, disease mechanisms and therapeutic opportunities," J. Intern. Med. 261(1):17-31 (2007).
Traxler, "Tyrosine kinase inhibitors in cancer treatment (Part II)," Exp. Opin. Ther. Patents 8(12):1599-1625.
Tsou et al., "Optimization of 6,7-disubstituted-4-(arylamino)quinoline-3-carbonitriles as orally active, irreversible inhibitors of human epidermal growth factor receptor-2 kinase activity," J. Med. Chem. 48(4):1107-1131 (2005).
Tsou, "American Chemical Society—226th National Meeting. Novel Substituted 4-Anilinoquinoline-3-carbonitriles as orally active, irreversible binding inhibitors of HER-2 Kinase," (abstr. 14) 2003.
Twelves et al., "Erlotinib in combination with capecitabine and docetaxel in patients with metastatic breast cancer: a dose-escalation study," Eur. J. Cancer 44(3):419-426 (2008) (Epub Jan. 30, 2008).
Ullrich et al., "Human epidermal growth factor receptor cDNA sequence and aberrant expression of the amplified gene in A431 epidermoid carcinoma cells," Nature 309(5967):418-425 (1984).
Untch, "Targeted Therapy for Early and Locally Advanced Breast Cancer," Breast Care (Basel) 5(3):144-152 (2010) (Epub Jun. 16, 2010).
Upeslacis, Janis, Meeting at Mcgill University, Canada, Evolution of Kinase Inhibitors At Wyeth, Oct. 16, 2002.
Van Arnum, "Evaluating late-stage pipelines and potential: will 2011 be a more promising year for new molecular entities? A review of Big Pharma's late-stage pipeline shows what might lie ahead." Pharmaceutical Technology 35.2 (2011): 52+. Expanded Academic ASAP. Web. Jul. 18, 2011.
Van Schaeybroeck et al., "Epidermal growth factor receptor activity determines response of colorectal cancer cells to gefitinib alone and in combination with chemotherapy," Clin. Cancer Res. 11(20):7480-7489 (2005).
Vasudevan et al., "AKT-independent signaling downstream of oncogenic PIK3CA mutations in human cancer," Cancer Cell 16(1):21-32 (2009).
Vazquez et al., "HER2-Positive Breast Cancer: Analysis of Efficacy in Different Groups," Cancer Chemother. Rev. 4(4):224-240 (2009).
Vengerovsky, "Farmacologicheskaya nesovmestimost," Bulleten' sibirskoi meditsini 3:49-56 (2003). (English translation of Abstract provided).
Vincent et al., "Anticancer efficacy of the irreversible EGFr tyrosine kinase inhibitor PD 0169414 against human tumor xenografts," Cancer Chemother. Pharmacol. 45(3):231-238 (2000).
Vivanco and Mellinghoff, "Epidermal growth factor receptor inhibitors in oncology," Curr. Opin. Oncol. 22(6):573-578 (2010).
Von Eyben, "Epidermal growth factor receptor inhibition and non-small cell lung cancer," Crit. Rev. Clin. Lab. Sci. 43(4):291-323 (2006).
Vora et al., "Novel Therapeutics in Breast Cancer—Looking to the Future," Update on Cancer Therapeutics 3:189-205 (2009).
Wagner and Kaufmann, "Prospects for the Use of ATR Inhibitors to Treat Cancer," Pharmaceuticals 3:1311-1334 (2010).
Walko and Lindley, "Capecitabine: a review," Clin. Ther. 27(1):23-44 (2005).
Wang et al., "Characterization of HKI-272 covalent binding to human serum albumin," Drug Metab. Dispos. 38(7):1083-1093 (2010) (Epub Apr. 16, 2010).
Ware et al., "A mechanism of resistance to gefitinib mediated by cellular reprogramming and the acquisition of an FGF2-FGFR1 autocrine growth loop," Oncogenesis 2:e39 (2013).
Weber, "Toward a molecular classification of cancer," Toxicology Dec. 5, 2010;278(2):195-198 (2010) (Epub Oct. 24, 2009).
Wen and Drappatz, "Novel therapies for meningiomas," Expert Rev. Neurother. 6(10):1447-1464 (2006).
Wheatley-Price and Shepherd, "Epidermal growth factor receptor inhibitors in the treatment of lung cancer: reality and hopes," Curr. Opin. Oncol. 20(2):162-175 (2008).
Whenham et al., "HER2-positive breast cancer: from trastuzumab to innovatory anti-HER2 strategies," Clin. Breast Cancer 8(1):38-49 (2008).
Wickham, "Evolving treatment paradigms for chemotherapy-induced nausea and vomiting," Cancer Control 19(2 Suppl):3-9 (2012).
Widakowich et al., "HER-2 positive breast cancer: what else beyond trastuzumab based therapy?" Anticancer Agents Med. Chem. 8(5):488-496 (2008).
Widakowich et al., "Molecular targeted therapies in breast cancer: where are we now?" Int. J. Biochem. Cell. Biol. 2007;39(7-8):1375-1387 (2007) (Epub May 4, 2007).
Wissner and Mansour, "The development of HKI-272 and related compounds for the treatment of cancer," Arch. Pharm. (Weinheim) 341(8):465-477 (2008).
Wissner et al., "Dual irreversible kinase inhibitors: quinazoline-based inhibitors incorporating two independent reactive centers with each targeting different cysteine residues in the kinase domains of EGFR and VEGFR-2," Bioorg. Med. Chem. 15(11):3635-4368 (2007) (Epub Mar. 23, 2007).
Woenckhaus et al., "Prognostic value of PIK3CA and phosphorylated AKT expression in ovarian cancer," Virchows Arch. 450(4):387-395 (2007) (Epub Feb. 15, 2007).

(56) References Cited

OTHER PUBLICATIONS

Wondrak, "Redox-directed cancer therapeutics: molecular mechanisms and opportunities," Antioxid. Redox Signal. 11(12):3013-3069 (2009).
Wong et al., "A phase I study with neratinib (HKI-272), an irreversible pan ErbB receptor tyrosine kinase inhibitor, in patients with solid tumors," Clin. Cancer Res. 15(7):2552-2558 (2009) (Epub Mar. 24, 2009).
Wong et al., "HKI-272, an irreversible pan ErbB receptor tyrosine kinase inhibitory: Preliminary phase 1 results in patients with solid tumors," J. Clin, Oncol. 24(18S):125s Abstr. 3018 (2006).
Wong, "HKI-272 in non small cell lung cancer," Clin. Cancer Res. 13(15 Pt 2):4593s-4596s (2007).
Wong, "Searching for a magic bullet in NSCLC: the role of epidermal growth factor receptor mutations and tyrosine kinase inhibitors," Lung Cancer 60(Suppl 2):S10-S18 (2008).
World Health Organization (2008). *Fact Sheet—Cancer, No. 297*, 2008. Retrieved from http://www.who.int/mediacentre/factsheets/fs297/en/.
World Health Organization (2008). *World Health Statistics*, 2008. Retrieved from http://www.who.int/gho/publications/world_health_statistics/EN_WHS08_Full.pdf?ua=1.
Written Opinion of the International Searching Authority for International Application No. PCT/US2009/047643 dated Dec. 17, 2010.
Wu et al., "Design and synthesis of tetrahydropyridothieno[2,3-d]pyrimidine scaffold based epidermal growth factor receptor (EGFR) kinase inhibitors: the role of side chain chirality and Michael acceptor group for maximal potency," J. Med. Chem. 53(20):7316-7326 (2010).
Wu et al., "Somatic mutation and gain of copy number of PIK3CA in human breast cancer," Breast Cancer Res. 7(5):R609-R616 (2005) (Epub May 31, 2005).
Wu et al., "TAK-285, a Novel HER2/EGFR Inhibitor, Penetrates the CNS in Rats with an Intact Blood Brain Barrier (BBB),"Cancer Res. 69(24 Suppl): Abstr. 5098 (2009).
Wu et al., "Uncommon mutation, but common amplifications, of the PIK3CA gene in thyroid tumors," J. Clin. Endocrinol. Metab. 90(8):4688-4693 (2005) (Epub May 31, 2005).
Wykosky et al., "Therapeutic targeting of epidermal growth factor receptor in human cancer: successes and limitations," Chin. J. Cancer 30(1):5-12 (2011).
Xia et al., "Truncated ErbB2 receptor (p95ErbB2) is regulated by heregulin through heterodimer formation with ErbB3 yet remains sensitive to the dual EGFR/ErbB2 kinase inhibitor GW572016," Oncogene 23(3):646-653 (2004).
Xu et al., "Acquired resistance of lung adenocarcinoma to EGFR-tyrosine kinase inhibitors gefitinib and erlotinib," Cancer Biol. Ther. 9(8):572-582 (2010) (Epub Apr. 26, 2010).
Yamano, M., "Approach to crystal polymorph in process research of new drug," Journal of Synthetic Organic Chemistry Japan 65(9):907-913 (2007) [English translation not available].
Yang et al., "MicroRNA expression profiling in human ovarian cancer: miR-214 induces cell survival and cisplatin resistance by targeting PTEN," Cancer Res. 68(2):425-433 (2008).
Yano et al., "HGF-MET in Resistance to EGFR Tyrosine Kinase Inhibitors in Lung Cancer," Curr. Signal Transduct. Ther. 6(2):228-233 (2011).
Yim et al., "Rak functions as a tumor suppressor by regulating PTEN protein stability and function," Cancer Cell 15(4):304-314 (2009).
Yoshida et al., "Targeting epidermal growth factor receptor: central signaling kinase in lung cancer," Biochem. Pharmacol. 80(5):613-623 (2010) (Epub May 24, 2010).
Yoshimura et al., "EKB-569, a new irreversible epidermal growth factor receptor tyrosine kinase inhibitor, with clinical activity in patients with non-small cell lung cancer with acquired resistance to gefitinib," Lung Cancer 51(3):363-368 (2006) (Epub Dec. 20, 2005).
Yuan and Cantley, "PI3K pathway alterations in cancer: variations on a theme," Oncogene 27(41):5497-5510 (2008).
Yun et al., "The T790M mutation in EGFR kinase causes drug resistance by increasing the affinity for ATP," Proc. Natl. Acad. Sci. U.S.A. 105(6):2070-2075 (2008) (Epub Jan. 28, 2008).
Yuza et al., "Allele-dependent variation in the relative cellular potency of distinct EGFR inhibitors," Cancer Biol. Ther. 6(5):661-667 (2007) (Epub Feb. 13, 2007).
Zaczek et al., "The diverse signaling network of EGFR, HER2, HER3 and HER4 tyrosine kinase receptors and the consequences for therapeutic approaches," Histol. Histopathol. 20(3):1005-1015 (2005).
Zagrekova et al., "Drug Treatment of Breast Cancer," Rossijskij Medicinskij Zhurnal 14:605 (2002). (English Translation Not Available).
Zahnow, "ErbB receptors and their ligands in the breast," Expert Rev. Mol. Med. 8(23):1-21 (2006).
Zhang et al. Xenograft Models of Breast Cancer: the Link between Characteristics of Biomarker Expression and the Anti-tumor Effect of the Representative Therapies [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 647.
Zhang et al., "Advances in preclinical small molecules for the treatment of NSCLC," Expert Opin. Ther. Pat. 19(6):731-751 (2009).
Zhang et al., "Targeting cancer with small molecule kinase inhibitors," Nature 9:28-39 (2009).
Zhao et al., "Neratinib Reverses ATP-Binding Cassette Bl-Mediaed Chemotherapeutic Drug Resistance in Vitro, in Vivo, and Ex-Vivo," Mol. Pharmacal. 82: 47-58 (2012).
Zhou et al., "Activation of the PTEN/Mtor/STAT3 Pathway in Breast Cancer Stem-Like Cells Is Required for Viability and Maintenance," Proc. Natl. Acad. Sci. U.S.A. 104:16158-16163 (2007).
Zhou et al., "EGFR Intron I Polymorphism in Asian Populations and Its Correlation with EGFR Gene Expression and Amplification in Breast Tumor Tissues," Cancer Biol. Ther. 5(11):1445-1449 (2006).
Zhou et al., "Novel Mutant-Selective EGFR Kinase Inhibitors Against EGFR T790M," Nature 462(7276):1070-1074 (2009).
AstraZeneca Press Release, "TAGRISSO ™(osimertinib) (AZD9291) approved by the US FDA as treatment for patients with EGFR T790M mutation-positive metastatic non-small cell lung cancer," published Nov. 13, 2015. [Obtained from the Internet on Mar. 7, 2017].
Carmi et al., "Clinical perspectives for irreversible tyrosine kinase inhibitors in cancer," Biochem. Pharmacol. 84(11):1388-1399 (2012) (Epub Aug. 4, 2012).
Chew et al., "Phase II study of lapatinib in combination with vinorelbine, as first or second-line therapy in women with HER2 overexpressing metastatic breast cancer," SpringerPlus 3:108 (2014).
Cross et al., "AZD9291, an irreversible EGFR TKI, overcomes T790M-mediated resistance to EGFR inhibitors in lung cancer," Cancer Discov. 4(9):1046-1061 (2014) (Epub Jun. 3, 2014).
Fry et al., "Specific, irreversible inactivation of the epidermal growth factor receptor and erbB2, by a new class of tyrosine kinase inhibitor," Proc. Natl. Acad. Sci. U.S.A. 95(20):12022-12027 (1998).
Gandhi et al., "Phase I Study of Neratinib in Combination With Temsirolimus in Patients With Human Epidermal Growth Factor Receptor 2—Dependent and Other Solid Tumors," J. Clin. Oncol. 32(2):68-75 (2014) (Epub Dec. 9, 2013).
Scholl et al., "Targeting HER2 in other tumor types," Ann. Oncol. 12(Suppl. 1):S81-S87 (2001).
Smaill et al., "Tyrosine kinase inhibitors. 15. 4-(Phenylamino)quinazoline and 4- (phenylamino)pyrido [d]pyrimidine aciylamides as irreversible inhibitors of the ATP binding site of the epidermal growth factor receptor," J. Med. Chem. 42(10):1803-1815 (1999).
Tsou et al., "6-Substituted-4-(3-bromophenylamino)quinazolines as putative irreversible inhibitors of the epidermal growth factor receptor (EGFR) and human epidermal growth factor receptor (HER-2) tyrosine kinases with enhanced antitumor activity," J. Med. Chem. 44(17):2719-2734 (2001).

(56) References Cited

OTHER PUBLICATIONS

Wissner et al., "Synthesis and structure-activity relationships of 6,7-disubstituted 4-anilinoquinoline-3-carbonitriles. The design of an orally active, irreversible inhibitor of the tyrosine kinase activity of the epidermal growth factor receptor (EGFR) and the human epidermal growth factor receptor-2 (HER-2)," J. Med. Chem. 46(1):49-63 (2003).
Wyeth: "Study Evaluating HKI-272 in Combination With Vinorelbine in Subjects With Solid Tumors and Metastatic Breast Cancer," ClinicalTrials, Jun. 25, 2008. Retrieved from the Internet: URL: http://clinicaltrials.gov/ct2/show/NCT00706030?term=vinorelbine+hki-272&rank=1 [retrieved on Jan. 13, 2010].
Wyeth: "Study evaluating Neratinib in Combination With Vinorelbine in Subjects With Advanced or Metastatic Solid Tumors," ClinicalTrials, Aug. 5, 2009. Retrieved from the Internet: URL: http://clinicaltrials.gov/ct2/show/NCT/00958724?term=vinorelbine+hki-272&rank=2 [retrieved on Jan. 13, 2010].
Yap et al., "Targeting the PI3K-AKT-mTOR pathway: progress, pitfalls, and promises," Curr. Opin. Pharmacol. 8:393-412 (2008).
Japanese Official Action for Corresponding Japanese Patent Application No. 2010-258729, dated Apr. 12, 2013.
Japanese Official Action dated Sep. 17, 2013, for Japanese Patent Application No. 2011-289220.
Extended European Search Report dated Nov. 17, 2016 for European Application No. EP 16193659.6.
United States Patent and Trademark Office Final Office Action for U.S. Appl. No. 11/883,474, dated Dec. 9, 2015 (8 pages).
United States Patent and Trademark Office Final Office Action for U.S. Appl. No. 12/534,895, dated May 2, 2013 (20 pages).
United States Patent and Trademark Office Notice of Allowance for U.S. Appl. No. 12/534,895, dated Sep. 12, 2013 (6 pages).
United States Patent and Trademark Office Non-Final Office Action for U.S. Appl. No. 12/534,895, dated Nov. 1, 2011 (23 pages).
United States Patent and Trademark Office Final Office Action for U.S. Appl. No. 12/940,797, dated Mar. 29, 2012 (11 pages).
United States Patent and Trademark Office Notice of Allowance for U.S. Appl. No. 12/940,797, dated May 3, 2013 (12 pages).
United States Patent and Trademark Office Non-Final Office Action for U.S. Appl. No. 12/940,797, dated Sep. 30, 2011 (15 pages).
United States Patent and Trademark Office Non-Final Office Action for U.S. Appl. No. 12/940,797, dated Sep. 13, 2012 (20 pages).
Written Opinion of the International Searching Authority for International Application No. PCT/US2010/054934 dated May 10, 2011.
Written Opinion of the International Searching Authority for International Application No. PCT/US2011/020080 dated Feb. 28, 2011.
Depierre et al., "Vinorelbine versus vinorelbine plus cisplatin in advanced non-small cell lung cancer: a randomized trial," Atm. Oncol. 5(1):37-42 (1994).
Davies et al., "OSI-774 and vinorelbine in advanced solid tumors (with emphasis on non-small cell lung cancer, NSCLC): A phase I study," Proc. Am. Soc. Clin. Oncol. 22: 2003 (abstr 996). 2003 ASCO Annual Meeting.
"Progress of Research on Therapeutic Drugs and Molecular Pharmacology", edited by Zhou Hong et al., Sichuan University Press, published in Mar. 2004, pp. 46-47. (English translation attached).
Degardin et al., "Vinorelbine (navelbine) as a salvage treatment for advanced breast cancer," Ann. Oncol. 5(5):423-426 (1994).
Anzensei shiken gaidorain (Guidelines for safety testing), Pharmaceutical Affairs Bureau Notification No. 0603001, Jun. 3, 2003; Notification Date: Oct. 19, 2017. (English translation attached).

\* cited by examiner

MALEATE SALTS OF (E)-N-{4[3-CHLORO-4-(2-PYRIDINYLMETHOXY)ANILINO]-3-CYANO-7-ETHOXY-6-QUINOLINYL}-4-(DIMETHYLAMINO)-2-BUTENAMIDE AND CRYSTALLINE FORMS THEREOF

CROSS REFERENCE TO RELATED APPLICATIONS

This application is a continuation of U.S. patent application Ser. No. 14/825,612, filed Aug. 13, 2015, which is a continuation of U.S. patent application Ser. No. 13/765,356, filed Feb. 12, 2013, now U.S. Pat. No. 9,139,558, which is a continuation of U.S. patent application Ser. No. 13/441,168, filed Apr. 6, 2012, now U.S. Pat. No. 8,394,959, which is a continuation of U.S. patent application Ser. No. 13/181,375, filed Jul. 12, 2011, now U.S. Pat. No. 8,173,814, which is a divisional of U.S. patent application Ser. No. 12/251,924, filed Oct. 15, 2008, now U.S. Pat. No. 8,022,216, which further claims the benefit under 35 U.S.C. § 119(e) of U.S. Provisional Application No. 61/124,796, filed Oct. 17, 2007. The foregoing related applications, in their entirety, are incorporated herein by reference.

FIELD OF THE INVENTION

This invention is directed to maleate salts of (E)-N-{4-[3-chloro-4-(2-pyridinylmethoxy)anilino]-3-cyano-7-ethoxy-6-quinolinyl}-4-(dimethylamino)-2-butenamide, crystalline forms thereof, methods of preparing the salts, associated compounds, pharmaceutical compositions containing the maleate salt, and methods for their use. Maleate salts of (E)-N-{4-[3-chloro-4-(2-pyridinylmethoxy)anilino]-3-cyano-7-ethoxy-6-quinolinyl}-4-(dimethylamino)-2-butenamide are useful in the treatment of cancer.

BACKGROUND OF THE INVENTION

Compounds derived from 3-cyanoquinoline have been shown to have anti-tumor activity, which may make them useful as chemotherapeutic agents in treating various cancers, including but not limited to, pancreatic cancer, melanoma, lymphatic cancer, parotid tumors, Barrett's esophagus, esophageal carcinomas, head and neck tumors, ovarian cancer, breast cancer, epidermoid tumors, cancers of major organs, such as kidney, bladder, larynx, stomach, and lung, colonic polyps and colorectal cancer and prostate cancer. Examples of compounds derived from 3-cyanoquinoline are disclosed and shown to possess anti-tumor activity in U.S. Pat. Nos. 6,002,008; 6,432,979; and 6,288,082. One limitation of certain 3-cyanoquinoline compounds is that they are not water soluble in a free base form.

The crystalline form of a particular drug as a salt, a hydrate and/or any polymorph thereof is often one important determinant of the drug's ease of preparation, stability, water solubility, storage stability, ease of formulation and in-vivo pharmacology. It is possible that one crystalline form is preferable over another where certain aspects such as ease of preparation, stability, water solubility and/or superior pharmacokinetics are deemed to be critical. Crystalline forms of (E)-N-{4-[3-chloro-4-(2-pyridinylmethoxy)anilino]-3-cyano-7-ethoxy-6-quinolinyl}-4-(dimethylamino)-2-butenamide salts that possess a higher degree of water solubility than the free base but are stable fulfill an unmet need for stable, crystalline, water-soluble forms of substituted 3-cyanoquinoline compounds that selectively inhibit kinase activity, which in turn inhibit cell proliferation and tumorigenesis.

SUMMARY OF THE INVENTION

The present invention provides crystalline forms of (E)-N-{4-[3-chloro-4-(2-pyridinylmethoxy)anilino]-3-cyano-7-ethoxy-6-quinolinyl}-4-(dimethylamino)-2-butenamide maleate, which have been isolated and characterized as: an anhydrous form, a monohydrate form, and a mixture of the anhydrous and the monohydrate forms (referred to as a partial hydrate form). The invention is also directed to methods for using this maleate salt and the crystalline forms thereof, and pharmaceutical formulations containing them.

The invention provides an isolated crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I), characterized by differential scanning calorimetry (DSC), as exhibiting an onset temperature in the range of about 196-204° C., at which melting and decomposition occur.

The invention also provides an isolated crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I), wherein the maleate salt is characterized by X-ray diffraction (XRD) peaks at the following angles)(±0.20°) of 2θ in its X-ray diffraction pattern: 6.16, 7.38, 8.75, 10.20, 12.24, 12.61, 14.65, 15.75, 17.33, 18.64, 19.99, 20.66, 21.32, 22.30, 23.18, 24.10, 24.69, 25.49, 26.09, 26.54, 27.52, 28.62, and 29.43. In a separate embodiment, the isolated crystalline form of anhydrous (E)-N-{4-[3-chloro-4-(2-pyridinyl methoxy)anilino]-3-cyano-7-ethoxy-6-quinolinyl}-4-(dimethylamino)-2-butenamide maleate exhibits an X-ray diffraction pattern wherein all of the X-ray diffraction peaks are at about the 2θ angles disclosed above.

The invention provides an isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), exhibiting water loss at about 50° C. and characterized by a water content of about 2.5 to 2.7% by weight, based on the weight of the compound as a monohydrate.

The invention also provides an isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), wherein the maleate salt is characterized by XRD peaks at the following angles)(±0.20° of 2θ in its X-ray diffraction pattern: 6.53, 8.43, 10.16, 12.19, 12.47, 13.01, 15.17, 16.76, 17.95, 19.86, 21.11, 21.88, 23.22, 23.78, 25.69, 26.17, 27.06, 27.58, 28.26, 28.73, and 29.77. In a separate embodiment, the isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate exhibits an X-ray diffraction pattern wherein all of the X-ray diffraction peaks are at about the 2θ angles disclosed above.

The invention also provides an isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), characterized by DSC, as exhibiting an onset temperature in the range of 196-204° C., at which melting and decomposition occur, especially at a transition temperature of about 203.8° C.

The invention provides an isolated crystalline form of a partially hydrated (E)-N-{4-[3-chloro-4-(2-pyridinylmethoxy)anilino]-3-cyano-7-ethoxy-6-quinolinyl}-4-(dimethylamino)-2-butenamide maleate (Form III), characterized by a water content of about 0.8 to about 2.4% by weight, including about 1.5% to about 2.3% by weight, based on the weight of the compound.

The present invention provides a method of preparing the maleate salt by mixing (E)-N-{4-[3-chloro-4-(2-pyridinylmethoxy)anilino]-3-cyano-7-ethoxy-6-quinolinyl}-4-(dimethylamino)-2-butenamide (the free base) with maleic acid and dissolving the mixture in a water-alcohol solution at an elevated temperature. The resulting solution is cooled and the cooled solution contains (E)-N-{4-[3-chloro-4-(2-pyridinylmethoxy)anilino]-3-cyano-7-ethoxy-6-quinolinyl}-4-(dimethylamino)-2-butenamide maleate.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate In the form of a crystalline monohydrate (Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent and an amount of water and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate (Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent; adding a solution comprising an amount of water in an organic solvent; and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate(Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent and an amount of water and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate(Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent comprising an amount of water and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate(Form II) comprising the steps of: mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent comprising an amount of water over a period of days and filtering crystalline monohydrate that precipitates from the mixture.

The invention also provides a method of preparing (E)-N-{4-[3-chloro-4-(2-pyridinylmethoxy)anilino]-3-cyano-7-ethoxy-6-quinolinyl}-4-(dimethylamino)-2-butenamide maleate in anhydrous form (Form I) comprising the step of: drying under vacuum (E)-N-{4-[3-chloro-4-(2-pyridinylmethoxy)anilino]-3-cyano-7-ethoxy-6-quinolinyl}-4-(dimethylamino)-2-butenamide maleate as a monohydrate (Form II) at a temperature greater than 30° C. for about 12 to about 48 hours.

The invention also provides a pharmaceutical formulation comprising: (E)-N-{4-[3-chloro-4-(2-pyridinylmethoxy)anilino]-3-cyano-7-ethoxy-6-quinolinyl}-4-(dimethylamino)-2-butenamide maleate and one or more associated compounds having the following structures:

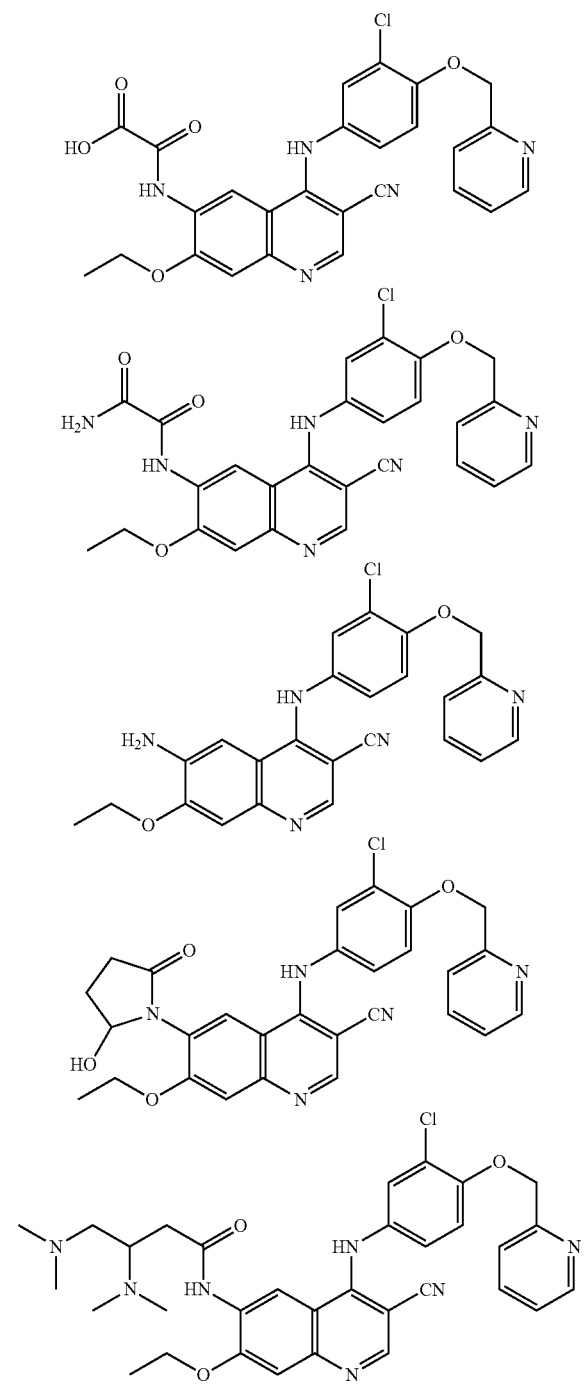

-continued

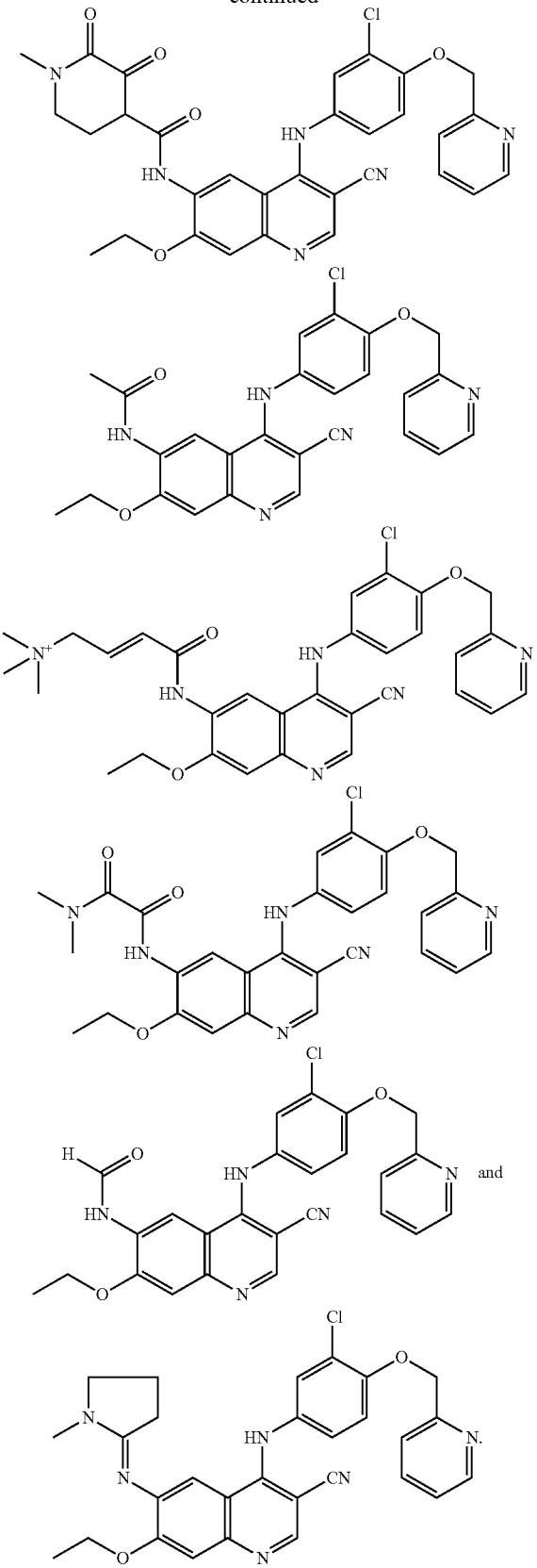

and

The present invention also provides a pharmaceutical composition for the inhibition of HER-2 kinase activity comprising a therapeutically-effective amount of (E)-N-{4-[3-chloro-4-(2-pyridinylmethoxy)anilino]-3-cyano-7-ethoxy-6-quinolinyl}-4-(dimethylamino)-2-butenamide maleate and a pharmaceutically acceptable carrier. The pharmaceutical composition may also contain one or more of the associated compounds discussed above. The maleate salt may be in an anhydrous form, a monohydrate form, and combinations of these forms.

The present invention also provides a method for preventing, treating, or inhibiting cancer by administering a therapeutically-effective amount of (E)-N-{4-[3-chloro-4-(2-pyridinylmethoxy)anilino]-3-cyano-7-ethoxy-6-quinolinyl}-4-(dimethylamino)-2-butenamide maleate to a subject. The subject may be a mammal, and more specifically, a human. The maleate salt may be administered in its anhydrous form, monohydrate form, or partially hydrated form. One or more of the associated compounds discussed above may also be administered during this method.

Figure 1:
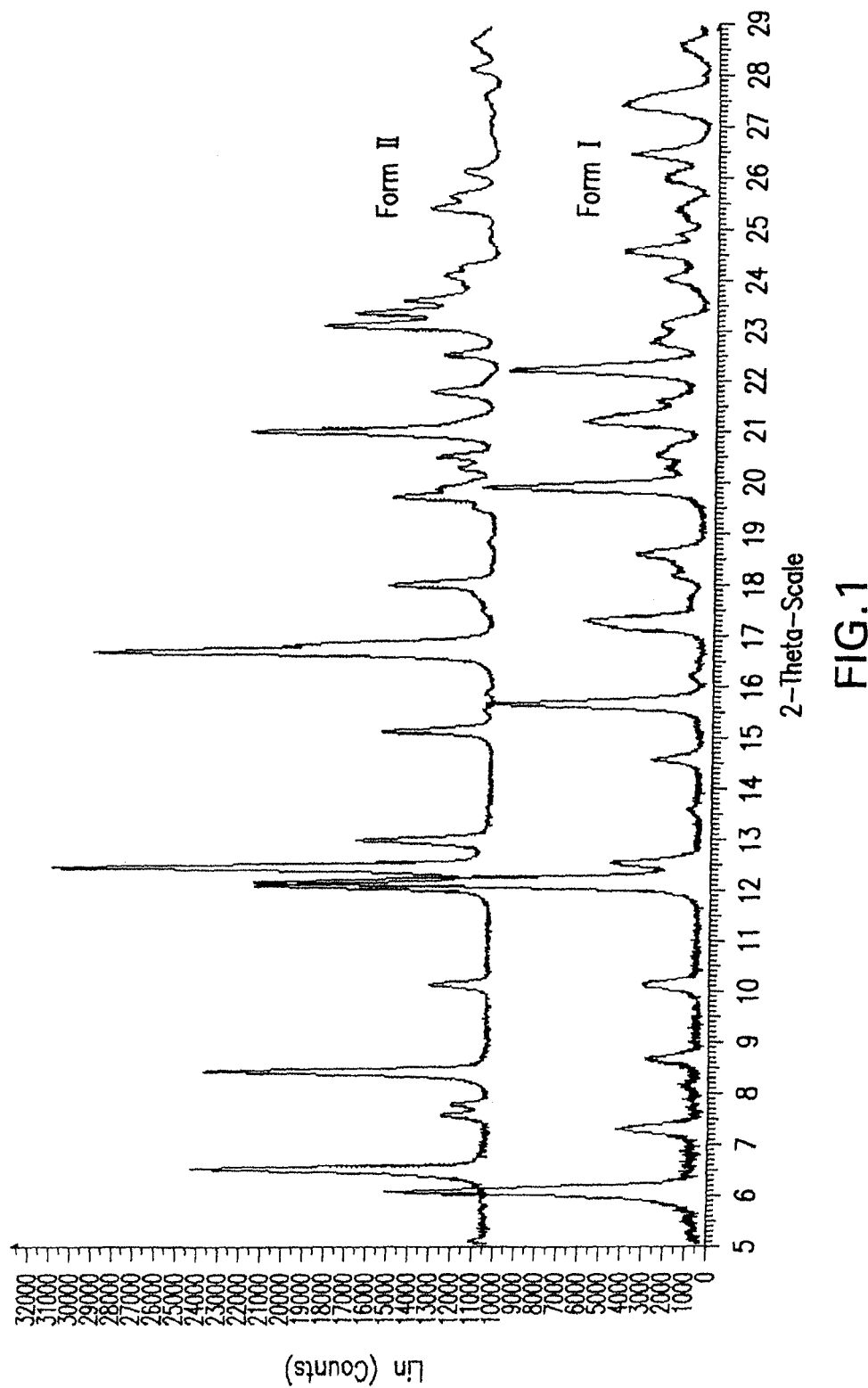
FIG. 1. The XRD scans of two crystalline forms of (E)-N-{4-[3-chloro-4-(2-pyridinylmethoxy)anilino]-3-cyano-7-ethoxy-6-quinolinyl}-4-(dimethylamino)-2-butenamide maleate, anhydrous Form I and monohydrate Form II.

DETAILED DESCRIPTION OF THE INVENTION (E)-N-{4-[3-chloro-4-(2-pyridinylmethoxy)anilino]-3-cyano-7-ethoxy-6-quinolinyl}-4-(dimethylamino)-2-butenamide is an irreversible inhibitor to Her-2 (also known as ErbB-2 or neu) kinase, a member of the epidermal growth factor receptor (EGFR) family. EGFR family members have been implicated in tumorigenesis and associated with poor prognosis in tumor types in humans. The structure of the (E)-N-{4-[3-chloro-4-(2-pyridinylmethoxy)anilino]-3-cyano-7-ethoxy-6-quinolinyl}-4-(dimethylamino)-2-butenamide in the form of a free base is shown below:

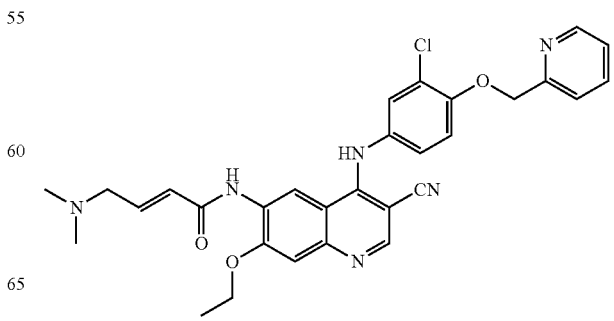

The compound (E)-N-{4-[3-chloro-4-(2-pyridinyl-methoxy)anilino]-3-cyano-7-ethoxy-6-quinolinyl}-4-(dimethylamino)-2-butenamide in the form of a free base is described in U.S. Pat. No. 6,288,082. The compound is classified, based on the Biopharmaceutical Classification System, as a BCS Class IV compound (low water solubility and low permeability). The free base has low solubility in water, with a water solubility of about 1 µg/mL at about pH 7. The water solubility increases with decreasing pH as the compound becomes ionized. This compound is water soluble at gastrointestinal pH, and dissolution is not rate limiting. There is a need for a form of this compound with improved physicochemical properties.

The present invention provides a water-soluble acid addition salt form of (E)-N-{4-[3-chloro-4-(2-pyridinyl-methoxy)anilino]-3-cyano-7-ethoxy-6-quinolinyl}-4-(dimethylamino)-2-butenamide. The free base compound is capable of forming salts with a variety of pharmaceutically suitable acids. Pharmaceutically suitable acids include, but are not limited to for example, acetic, fumuric, maleic, methanesulfonic, succinic, sulfuric, tartaric, and p-toluenesulfonic acid. The physicochemical properties of each acid addition salt form were evaluated to screen for an optimal pharmaceutical salt form, as shown in Table 1.

The (E)-N-{4-[3-chloro-4-(2-pyridinyl methoxy)anilino]-3-cyano-7-ethoxy-6-quinolinyl}-4-(dimethylamino)-2-butenamide maleate salt is crystalline and has higher solubility in water as compared to the free base as shown in Table 2.

TABLE 2

SOLUBILITY COMPARISON OF FREE BASE AND MALEATE SALT

| Solvent | free base | Maleate salt |
| --- | --- | --- |
| Water | < LOD* (pH 8.2) | 0.43 mg/mL (pH 5.00) |
| 2% Tween™ 80** in water | 0.05 mg/mL (pH 6.4) | 1.12 mg/mL (pH 5.06) |

*LOD = limit of detection
**Also known as Polysorbate™ 80, a non-ionic solvent prepared from polyoxylated sorbitol and oleic acid.

A comparison of the systemic exposure (SE) data for (E)-N-{4-[3-chloro-4-(2-pyridinylmethoxy)anilino]-3-cyano-7-ethoxy-6-quinolinyl}-4-(dimethylamino)-2-butenamide has been conducted on data extracted from multiple preclinical studies in the rat. The analysis of these data

TABLE 1

PHYSICOCHEMICAL PROPERTIES OF SALT FORMS OF (E)-N-{4-[3-CHLORO-4-(2-PYRIDINYLMETHOXY)ANILINO]-3-CYANO-7-ETHOXY-6-QUINOLINYL}-4-(DIMETHYLAMINO)-2-BUTENAMIDE

| Salt | Acid/Base Ratio (by NMR) | Crystallinity (by XRD) | Crystallinity (by Microscopy) | DSC * ($T_{apex}$) | TGA (30-150° C.) | Residual Solvents (%) | pH | Solubility (mg/g) |
| --- | --- | --- | --- | --- | --- | --- | --- | --- |
| 1 | Acetate (not a salt) | Crystalline | Crystalline Fine needles | 116° C., 186° C. | 6.46% | 6.9 | 8.34 | <LOD |
| 2 | Mesylate (1:1) | Crystalline (moderate) | Crystalline Fine needles | 88° C., 141° C. | 5.03% | 0.56 | 4.29 | 10.62 |
| 3 | Tosylate (1:1) | Crystalline (low) | Crystalline Irregular particles | 159° C. | 2.1% | 1.17 | 4.72 | 6.89 |
| 4 | Maleate (1:1) | Crystalline | Crystalline Irregular particles | 195° C. | 0.5% | 1.19 | 5.11 | 0.37 |
| 5 | Fumarate (1:1) | Amorphous | Amorphous | Unclear | 2.71% | 0.13 | 3.53 | 0.78 |
| 6 | Tartrate (1:1) | Amorphous | Amorphous | Unclear | 2.98% | 0.14 | 3.49 | 0.66 |
| 7 | Succinate (1:1) | Amorphous w/crystalline features | Amorphous w/ crystalline features | 109° C. | 1.73% | 0.86 | 3.97 | 3.08 |
| 8 | Citrate (1:1) | Amorphous | Amorphous | Unclear | 2.86% | 0.56 | 3.45 | 0.30 |
| 9 | Sulfate (2:1 assumed) | Amorphous | Amorphous | 149° C. | 4.42% | 0.0 | 3.01 | 1.07 |

* Minor endotherms and some broad endotherms are not listed.

Of the nine salts, the maleate salt exhibited advantageous physicochemical properties. The maleate salt was crystalline and less hygroscopic. The mesylate salt was hygroscopic and less crystalline. The tosylate salt was even less attractive, primarily due to its higher molecular weight and safety concerns. Although the acetate "salt" appeared to be crystalline, NMR revealed that the product prepared from acetic acid was in fact not a salt. The fact that the product prepared from acetic acid was insoluble in water with a resulting alkaline pH confirmed that it largely retained the free base properties.

indicated that, in the rat, administration of the compound as the maleate salt provided a two-fold increase in AUC (area under concentration), as compared to the free base, when administered at a dose range of 5 to 45 mg/kg. The systemic availability of the compound as the free base was relatively low (20%), and the presence of significant amounts of drug in the feces could be attributed to poor absorption. The increased solubility of the maleate salt appears to enhance the absorption of the compound in the rat. Table 3 presents the plasma compound mean AUC and $C_{max}$ data observed in rats.

TABLE 3

MEAN (SE) COMPOUND PHARMACOKINETICS IN RATS

| Form | Dose (mg/kg) | Day | N | $C_{max}$ (ng/mL) Male | $C_{max}$ (ng/mL) Female | $AUC_{0-24}$ (ng·hr/mL) Male | $AUC_{0-24}$ (ng·hr/mL) Female | AUC/Dose Male | AUC/Dose Female |
|---|---|---|---|---|---|---|---|---|---|
| Maleate Salt | 5 | 28 | 3 | 1199 (138) | 1381 (220) | 8224 (630) | 9534 (844) | 1645 (126) | 1907 (169) |
| Free Base | 10 | 10 | 3 | 814 (116) | ND | 6785 (642) | ND | 678 (64) | ND |
| Maleate Salt | 15 | 28 | 3 | 3418 (802) | 3555 (628) | 30217 (2666) | 34177 (2654) | 2014 (178) | 2278 (177) |
| Free Base | 20 | 1 | 4 | 1009 (194) | ND | 8513[a] (1616) | ND | 426 (81) | ND |
| Free Base | 30 | 10 | 3 | 1654 (65) | 2437 (708) | 20389 (2331) | 24956 (4318) | 680 (78) | 832 (145) |
| Maleate Salt | 45 | 28 | 3 | 4615 (560) | 4562 (406) | 65062 (4791) | 75640 (6352) | 1446 (106) | 1681 (141) |
| Free Base | 100 | 10 | 3 | 3818 (656) | ND | 58270 (12513) | ND | 583 (125) | ND |

[a]$AUC_{0-\infty}$
ND = Not Dosed
Maleate salt administered at 10 mL/kg with suspensions of 0.5 to 4.5 mg/mL
Free base administered at 10 mL/kg with suspensions of 1 to 10 mg/mL The maleate salt consistently and reproducibly exhibited beneficial physicochemical properties, as shown in Table 4.

TABLE 4

PHYSICOCHEMICAL PROPERTIES OF MALEATE SALT PILOT BATCHES

| Run | Batch Size | Crystallinity (Microscopy) | Particle Size* | DSC (Tonset °C.) | % Moisture (KF) | Residual Solvent (%) | Solution pH | Aqueous Solubility*** (mg/g) | HPLC Purity (%) |
|---|---|---|---|---|---|---|---|---|---|
| 1 | 0.5 g | Crystalline Fine rods | 5-10 μm | 195 | 0.59 | 1.19 | 5.11 | 0.37 | 99.38 |
| 2 | 6.6 g | Crystalline Fine needles | 5-50 μm | 197.6 | 0.36 | 0.1 EtOAc | 5.10 | 0.50 | 99.70 |
| 3 | 4 g | Crystalline Fine needles | 25-100 μm | 196.3 | 0.35 | ND** | 5.15 | 0.44 | 99.52 |

*Particle size is estimated from the captured image from light microscope.
**ND: not determined
***s the free base In addition to exhibiting poor water solubility, the compound (E)-N-{4-[3-chloro-4-(2-pyridinylmethoxy)anilino]-3-cyano-7-ethoxy-6-quinolinyl}-4-(dimethylamino)-2-butenamide in the form of a free base interacts with emectic receptors in the stomach, giving rise to diarrhea in mammals. The maleate salt of (E)-N-{4-[3-chloro-4-(2-pyridinylmethoxy)anilino]-3-cyano-7-ethoxy-6-quinolinyl}-4-(dimethylamino)-2-butenamide, however, unexpectedly mitigates such problems and minimizes emectic receptor interactions in mammals.

The maleate salt is prepared by mixing (E)-N-{4-[3-chloro-4-(2-pyridinylmethoxy)anilino]-3-cyano-7-ethoxy-6-quinolinyl}-4-(dimethylamino)-2-butenamide (the free base) with maleic acid and dissolving the mixture in a water-alcohol solution at an elevated temperature. The resulting solution is cooled and the cooled solution contains (E)-N-{4-[3-chloro-4-(2-pyridinylmethoxy)anilino]-3-cyano-7-ethoxy-6-quinolinyl}-4-(dimethylamino)-2-butenamide maleate. According to one embodiment, (E)-N-{4-[3-chloro-4-(2-pyridinylmethoxy)anilino]-3-cyano-7-ethoxy-6-quinolinyl}-4-(dimethylamino)-2-butenamide maleate is prepared by combining maleic acid and the free base in a solution of water and n-propanol, as described in Scheme 1.

SCHEME 1

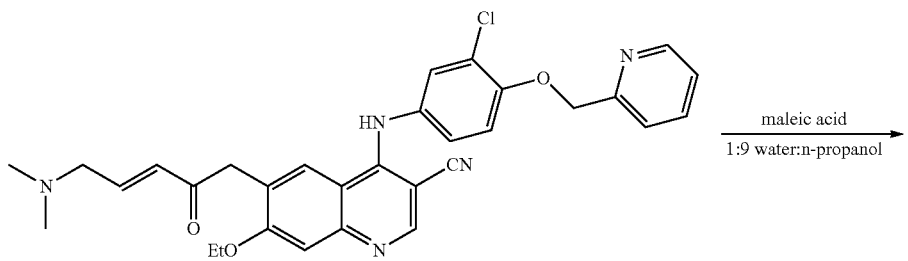

-continued

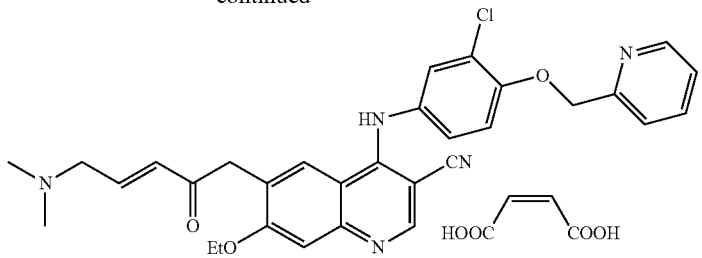

The reaction of the free base and maleic acid occurs at an elevated temperature of from about 40° C. to about 60° C., preferably between about 40° C. to about 50° C. The ratio of water:n-propanol may vary, for example between about 1:10 to about 1:5, and the optimal ratio of water:n-propanol is about 1:9. The water-alcohol solution may comprise from about 5% to about 20% by volume water and from about 80% to about 95% by volume alcohol. The alcohol may be n-propanol. In one embodiment, the water-alcohol solution comprises about 10% by volume water and about 90% by volume n-propanol. The volume of the solvent solution may be between about 8 to about 25 volumes, including about 10 to about 12 volumes. About 1.0-1.2 equivalents of maleic acid is used per equivalent of the free base, preferably about 1.03 equivalents of maleic acid per equivalent of the free base.

The resulting solution of the maleate salt may be clarified by filtration prior to cooling. The cooling step may be continued until the solution reaches a temperature of about 45° C. or less, including a temperature of about 39° C. or less, and more preferably to about 30° C. or less. In one embodiment, the solution is filtered after cooling to about room temperature, preferably from about 23° C. to about 25° C. Typically, the maleate salt begins to crystallize out of solution once the temperature reaches 37° C. or below. The solution may be allowed to sit for at least 12 hours, preferably about 12 to about 15 hours at room temperature, and is then filtered and washed to recover the crystalline maleate salt product. The resulting filter cake may be washed with the same or a different water-alcohol solution to obtain the product. The product may be dried to obtain crystalline (E)-N-{4-[3-chloro-4-(2-pyridinylmethoxy)anilino]-3-cyano-7-ethoxy-6-quinolinyl}-4-(dimethylamino)-2-butenamide maleate. At this point, the maleate salt product recovered and isolated is typically in the form of the monohydrate form of the maleate salt.

The product may be dried under vacuum with heating to make the anhydrous form of the maleate salt (Form I) at about 70 to about 95% yield, preferably about 80 to about 95% yield. This product is usually better than about 98% pure, and often about 99% pure. Typically, the drying process is performed over about 12 to about 48 hours to get complete conversion of the anhydrous form of the maleate salt to the monohydrate form of the maleate salt (Form II).

Shorter drying times generally result in mixtures of the two crystalline forms. The drying process is often performed at temperatures greater than room temperature. In one embodiment, drying of the maleate salt is performed at a temperature greater than about 30° C., preferably from about 40° C. to about 60° C., and in another embodiment at about 50° C.

The maleate salt is soluble in many polar solvents, which will be known to one skilled in the art, but dimethyl sulfoxide (DMSO) is often used if a small solvent volume is desired. The DMSO solution can be heated to about 45° C. to about 60° C. to further enhance solubility. Once the anhydrous maleate salt is in solution, water may be added, typically quickly, causing the crystallization that provides the crystalline monohydrate form upon filtration. The anhydrous salt may be dissolved in a solvent, for example DMSO, and to this solution may be added an aqueous solution of water and an organic solvent, for example such as tetrahydrofuran (THF), isopropanol (IPA), n-propanol, acetone, ethanol, methanol, and acetonitrile. In one embodiment, the organic solvent used is IPA, in another embodiment it is n-propanol, and in a third embodiment a mixture of these two organic solvents is used. The water content of the aqueous solution can be as little as 5%, but may be about 7.5% or greater, and in one embodiment is between about 10% and about 15%. The resulting solution then may be allowed to sit for up to about 24 hours, and in one embodiment is allowed to sit for between about 12 hours and about 24 hours, to allow for crystallization to occur. Filtration of the mixture yields a crystalline monohydrate form of the maleate salt. For purposes of this invention, the term "organic solvent and water" refers to a solution of an organic solvent, such as for example tetrahydrofuran (THF), DMSO, methanol, ethanol, isopropyl alcohol or acetonitrile, and water wherein the organic solvent comprises greater then 50% of the solution by volume.

The invented maleate salt of (E)-N-{4-[3-chloro-4-(2-pyridinylmethoxy)anilino]-3-cyano-7-ethoxy-6-quinolinyl}-4-(dimethylamino)-2-butenamide was isolated in three different crystalline forms: an anhydrous form (Form I), a monohydrate form (Form II) and a partially hydrated form (Form III), which comprises a mixture of Form I and Form II.

According to one embodiment, the anhydrous form of (E)-N-{4-[3-chloro-4-(2-pyridinylmethoxy)anilino]-3-cyano-7-ethoxy-6-quinolinyl}-4-(dimethylamino)-2-butenamide maleate (Form I) is obtained as a crystalline solid by drying the reaction product of (E)-N-{4-[3-chloro-4-(2-pyridinylmethoxy)anilino]-3-cyano-7-ethoxy-6-quinolinyl}-4-(dimethylamino)-2-butenamide and maleic acid. Drying includes air drying, heating and drying under reduced pressure. In an alternative embodiment, the anhydrous form of (E)-N-{4-[3-chloro-4-(2-pyridinylmethoxy)anilino]-3-cyano-7-ethoxy-6-quinolinyl}-4-(dimethylamino)-2-butenamide maleate (Form I) is obtained as a crystalline solid by drying the monohydrate form of (E)-N-{4-[3-chloro-4-(2-pyridinylmethoxy)anilino]-3-cyano-7-ethoxy-6-quinolinyl}-4-(dimethylamino)-2-butenamide maleate (Form II).

The isolated crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I), is characterized by differential scanning calorimetry (DSC), as exhibiting an onset temperature in the range of about 196-204° C., at which melting and decomposition occur.

The anhydrous maleate salt (Form I) is characterized by X-ray diffraction (XRD) peaks at the following angles) (±0.20°) of 2θ in its X-ray diffraction pattern: 6.16, 7.38, 8.75, 10.20, 12.24, 12.61, 14.65, 15.75, 17.33, 18.64, 19.99, 20.66, 21.32, 22.30, 23.18, 24.10, 24.69, 25.49, 26.09, 26.54, 27.52, 28.62, and 29.43. In a separate embodiment, the isolated crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) exhibits an X-ray diffraction pattern wherein all of the X-ray diffraction peaks are at about the 2θ angles disclosed above.

According to one embodiment, (E)-N-{4-[3-chloro-4-(2-pyridinylmethoxy)anilino]-3-cyano-7-ethoxy-6-quinolinyl}-4-(dimethylamino)-2-butenamide maleate is prepared in the form of a crystalline monohydrate (Form II) by mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent and an amount of water and filtering crystalline monohydrate that precipitates from the mixture.

In a separate embodiment, (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate (Form II) is prepared by mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent; adding a solution comprising an amount of water in an organic solvent; and filtering crystalline monohydrate that precipitates from the mixture.

In another embodiment, (E)-N-{4-[3-chloro-4-(2-pyridinylmethoxy)anilino]-3-cyano-7-ethoxy-6-quinolinyl}-4-(dimethylamino)-2-butenamide maleate in the form of a crystalline monohydrate (Form II) is prepared by mixing anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) with an organic solvent comprising an amount of water over a period of days and filtering crystalline monohydrate that precipitates from the mixture. The period of days is suitably about 1-20 days.

The isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate (Form II), exhibits water loss at about 50° C., as measured by DSC, and is characterized by a water content of about 2.5 to 2.7% by weight, as measured by thermal gravimetric analysis (TGA), based on the weight of the compound as a monohydrate. The water content of the monohydrate form of the maleate salt was also measured by Karl Fischer titration.

(E)-N-{4-[3-chloro-4-(2-pyridinylmethoxy)anilino]-3-cyano-7-ethoxy-6-quinolinyl}-4-(dimethylamino)-2-butenamide maleate as a monohydrate (Form II) is characterized by X-ray diffraction peaks (XRD) at the following angles) (±0.20°) of 2θ in its X-ray diffraction pattern: 6.53, 8.43, 10.16, 12.19, 12.47, 13.01, 15.17, 16.76, 17.95, 19.86, 21.11, 21.88, 23.22, 23.78, 25.69, 26.17, 27.06, 27.58, 28.26, 28.73, and 29.77. In a separate embodiment, the isolated crystalline form of (E)-N-{4-[3-chloro-4-(2-pyridinylmethoxy)anilino]-3-cyano-7-ethoxy-6-quinolinyl}-4-(dimethylamino)-2-butenamide maleate monohydrate exhibits an X-ray diffraction pattern wherein all of the X-ray diffraction peaks are at about the 2θ angles disclosed above.

As used herein, the term Isolated means that more than 50% of the crystalline (E)-N-{4-[3-chloro-4-(2-pyridinylmethoxy)anilino]-3-cyano-7-ethoxy-6-quinolinyl}-4-(dimethylamino)-2-butenamide maleate salt present is one of Forms I and II. In one embodiment, at least 70% of the crystalline (E)-N-{4-[3-chloro-4-(2-pyridinylmethoxy)anilino]-3-cyano-7-ethoxy-6-quinolinyl}-4-(dimethylamino)-2-butenamide maleate salt present is one of Forms I and II. In a second embodiment, at least 80% of the maleate salt present is one of Forms I and II. In a third embodiment, at least 90% of the maleate salt present is one of Forms I and II.

The two crystalline forms of (E)-N-{4-[3-chloro-4-(2-pyridinylmethoxy)anilino]-3-cyano-7-ethoxy-6-quinolinyl}-4-(dimethylamino)-2-butenamide maleate, exhibit distinct XRD patterns and peaks. The XRD pattern for each maleate salt form is unique to that salt form. The XRD patterns of Forms I and II were determined by using techniques and equipment known to those skilled in the art of analytical chemistry and X-ray crystallography. XRD patterns were produced using powder samples and are comprised of a set of diffraction peaks, which can be expressed in 2 theta angles, d-spacing and/or relative peak intensities. The XRD patterns are shown in FIGS. 1, 5, 6, 7, and 8. Collection parameters for the X-ray data provided in FIGS. 1, 7 and 8 were as follows: voltage 40 kV; current 40.0 mA; 5.00-30.00 degree scan range; Bruker D8 Advance instrument; scan step size 0.01°; total scan time 30 minutes; using a Vantec-1 detector and NI filter. The X-ray data in FIGS. 5 and 6 were collected as follows: voltage 30 kV; current 15 mA; 3-40 degree scan range; 2.00°/min; Rigaku Miniflex bench top X-ray diffractometer.

The two-theta diffraction angles and the corresponding d-spacing values account for the positions of the peaks found in a XRD pattern. D-spacing values are calculated with observed two theta angles and copper KO wavelength using the Bragg equation. Variations in these numbers can result from using different diffractometers and also from the method of sample preparation. However, more variation can be expected for the relative peak intensities. Therefore, identification of the various forms should be based upon the observed two-theta angles and the d-spacings, and less importance should be given to the intensities. One skilled in the art would understand that the XRD patterns of Forms I and II obtained as described herein could contain additional peaks. Additionally, a skilled artisan would recognize that whether all the peaks are observed for a given form may be highly dependent on the concentration level of the form. FIG. 1 illustrates XRD scans of the two crystalline forms of the maleate salt, Form I and II. The crystalline anhydrous maleate salt form, Form I, is shown on the bottom, while the crystalline monohydrate form of the maleate salt, Form II, is shown on top.

Figure 2:
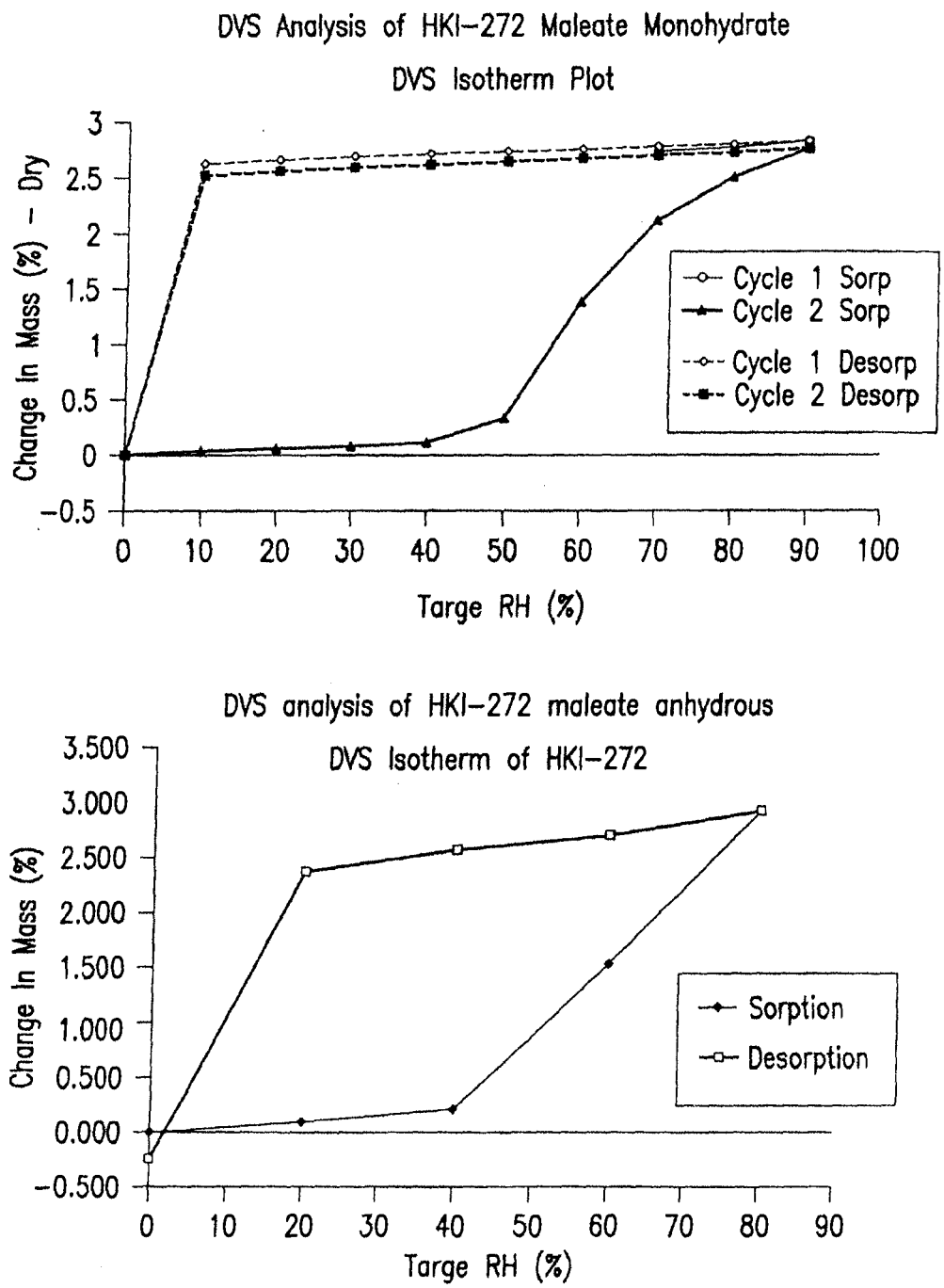
FIG. 2. A dynamic vapor sorption (DSV) isotherm plot of (E)-N-{4-[3-chloro-4-(2-pyridinylmethoxy)anilino]-3-cyano-7-ethoxy-6-quinolinyl}-4-(dimethylamino)-2-butenamide maleate, Forms I and II.

The relative stability and hygroscopicity of the two crystalline forms of the maleate salt was studied in detail by dynamic vapor sorption (DVS). The anhydrous form of the maleate salt absorbs water easily and converts to the crystalline monohydrate form of the maleate salt. Upon drying or a drop in the relative humidity, the crystalline monohydrate form of the maleate salt converts to the anhydrous form of the maleate salt, as summarized in FIG. 2. FIG. 2 is a dynamic vapor sorption isotherm plot which shows that (E)-N-{4-[3-chloro-4-(2-pyridinylmethoxy)anilino]-3-cyano-7-ethoxy-6-quinolinyl}-4-(dimethylamino)-2-butenamide maleate, Form I, gains moisture above 40% relative humidity (RH), especially at 60% RH and above. FIG. 2 also shows that Form II loses water at 20% RH and below, especially at 10% RH and below. DVS was performed under the following conditions: RH was set at 0%, 30%, 52.5%, 75% and 90%, with the sample exposed for 3 hours at each RH for two full cycles.

Figure 3:
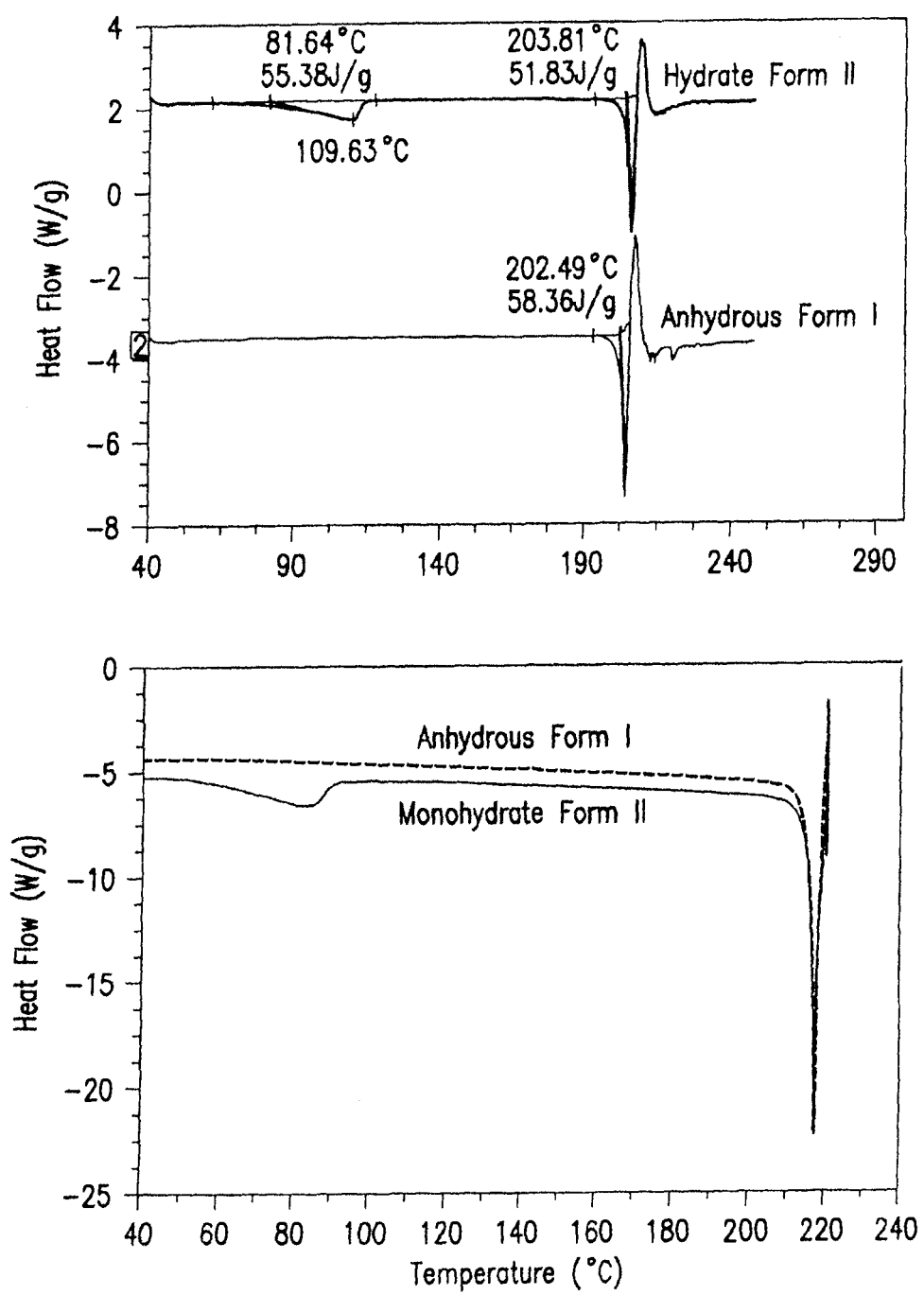
FIG. 3. A differential scanning calorimeter (DSC) plot of Forms I and II.

The two crystalline forms of (E)-N-{4-[3-chloro-4-(2-pyridinylmethoxy)anilino]-3-cyano-7-ethoxy-6-quinolinyl}-4-(dimethylamino)-2-butenamide maleate exhibit distinct DSC traces. A DSC plot of both Form I and Form II of the maleate salt is summarized in FIG. 3. Form I of the maleate salt exhibits one endothermic peak, indicating a transition temperature of 202.49° C. Form II of the maleate salt exhibits two endothermic peaks, a broad endotherm having an onset temperature of 55° C. corresponding to loss of water and a second endotherm indicating a transition temperature of 202.81° C. The transition temperatures are observed in the range of about 196-204° C. at which melting and decomposition occurs. DSC data, transition temperatures and heat flow, were collected using a TA instrument model Q1000 with the following parameters: 50 mL/min purge gas (N$_2$); scan range 40 to 240° C., scan rate 10° C./min. Pure, crystalline solids have a characteristic transition temperature, the temperature at which point the substance changes state, in the present case the solid transitions to a liquid. The transition between the solid and the liquid is so sharp for small samples of a pure substance that transition temperatures can be measured to 0.1° C. Because it is difficult to heat solids to temperatures above their transition temperatures, and because pure solids tend to transition over a very small temperature range, transition temperatures are often used to help identify compounds. Measurements of the transition temperature of a solid can also provide information about the purity of the substance. Pure, crystalline solids transition over a very narrow range of temperatures, whereas mixtures transition over a broad temperature range. Mixtures also tend to transition at temperatures below the transition temperatures of the pure solids.

Figure 4:
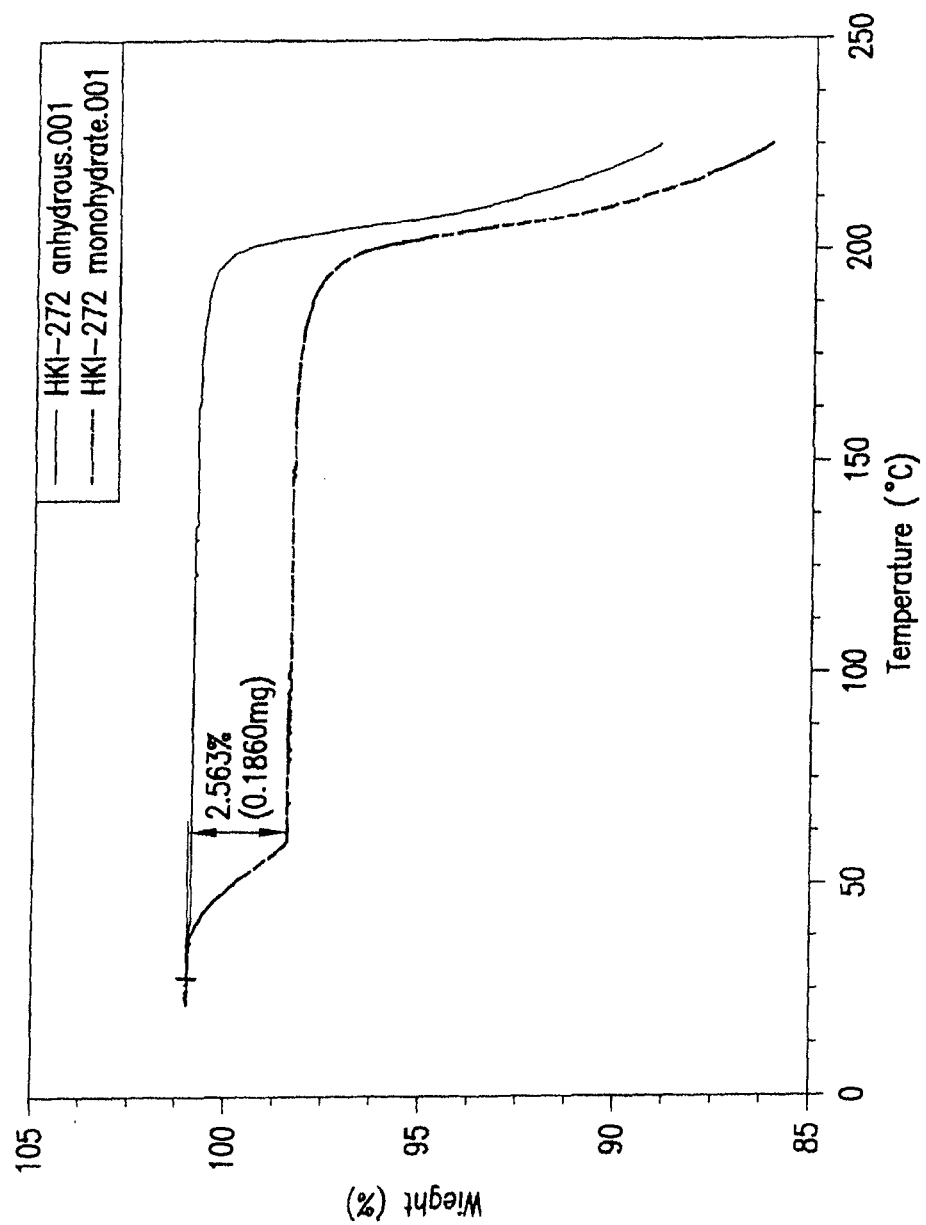
FIG. 4. A theromogravimetric analysis (TGA) plot of Forms I and II.

TGA data of the monohydrate and anhydrous forms of the maleate salt are summarized in FIG. 4. Form II of the maleate salt is characterized by a water content of about 2.5 to 2.7% by weight, as measured by TGA, based on the weight of the compound as a monohydrate. TGA data were collected using a TA Instrument Model Q. A heating rate of 10° C./min between 30-220° C. was used and the TGA chamber was under 40 mL/min flow of nitrogen.

A third crystalline form of the maleate Is salt is observed and referred to as the partial hydrate (Form III), as observed from XRD. The partial hydrate is a mixture of Form I and Form II of the maleate salt. The partially hydrated (E)-N-{4-[3-chloro-4-(2-pyridinylmethoxy)anilino]-3-cyano-7-ethoxy-6-quinolinyl}-4-(dimethylamino)-2-butenamide maleate (Form III), is characterized by a water content of about 0.8 to about 2.4% by weight, including about 1.5% to about 2.3% by weight, based on the weight of the compound.

Figure 5:
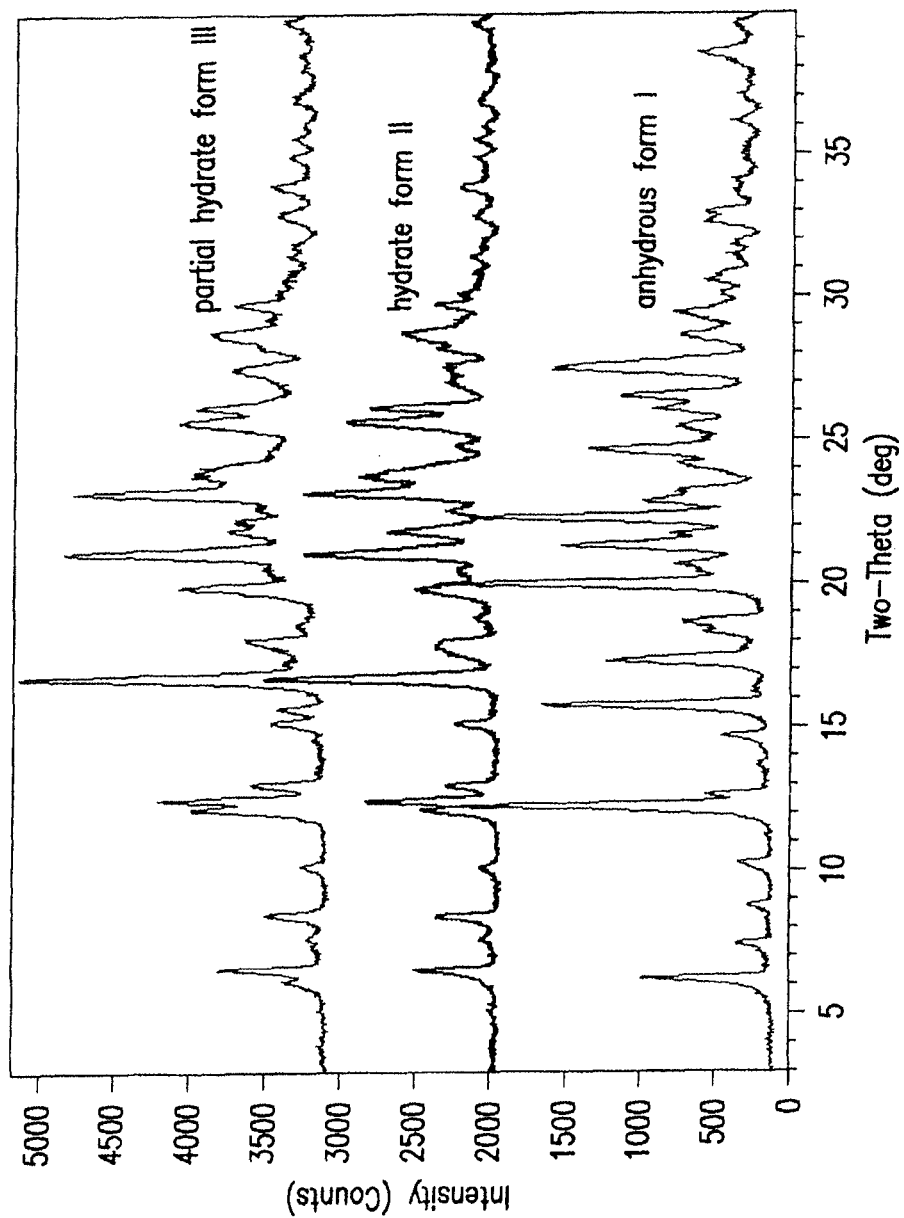
FIG. 5. XRD scans of Forms I, II and III (partial hydrate form) after exposure of Form I to 75% relative humidity at an ambient temperature for 22 days.

FIG. 5 includes an XRD scan of each of anhydrous Form I, monohydrate Form II and partial hydrate Form III of (E)-N-{4-[3-chloro-4-(2-pyridinylmethoxy)anilino]-3-cyano-7-ethoxy-6-quinolinyl}-4-(dimethylamino)-2-butenamide maleate after exposure of the anhydrous form of the maleate salt to a relative humidity of 75% at an ambient temperature of 20-25° C. for 22 days.

Figure 6:
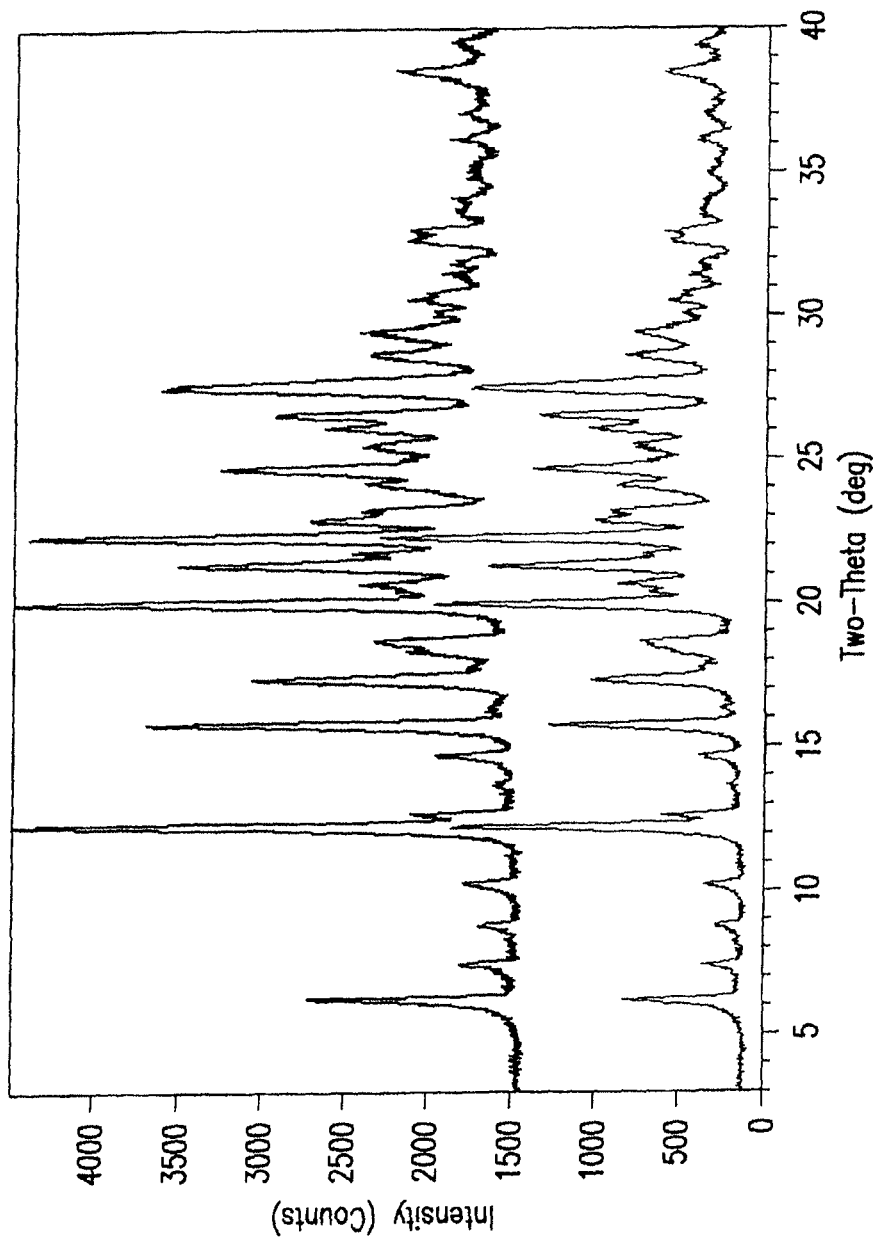
FIG. 6. XRD scans of two batches of Form I.
Figure 7:
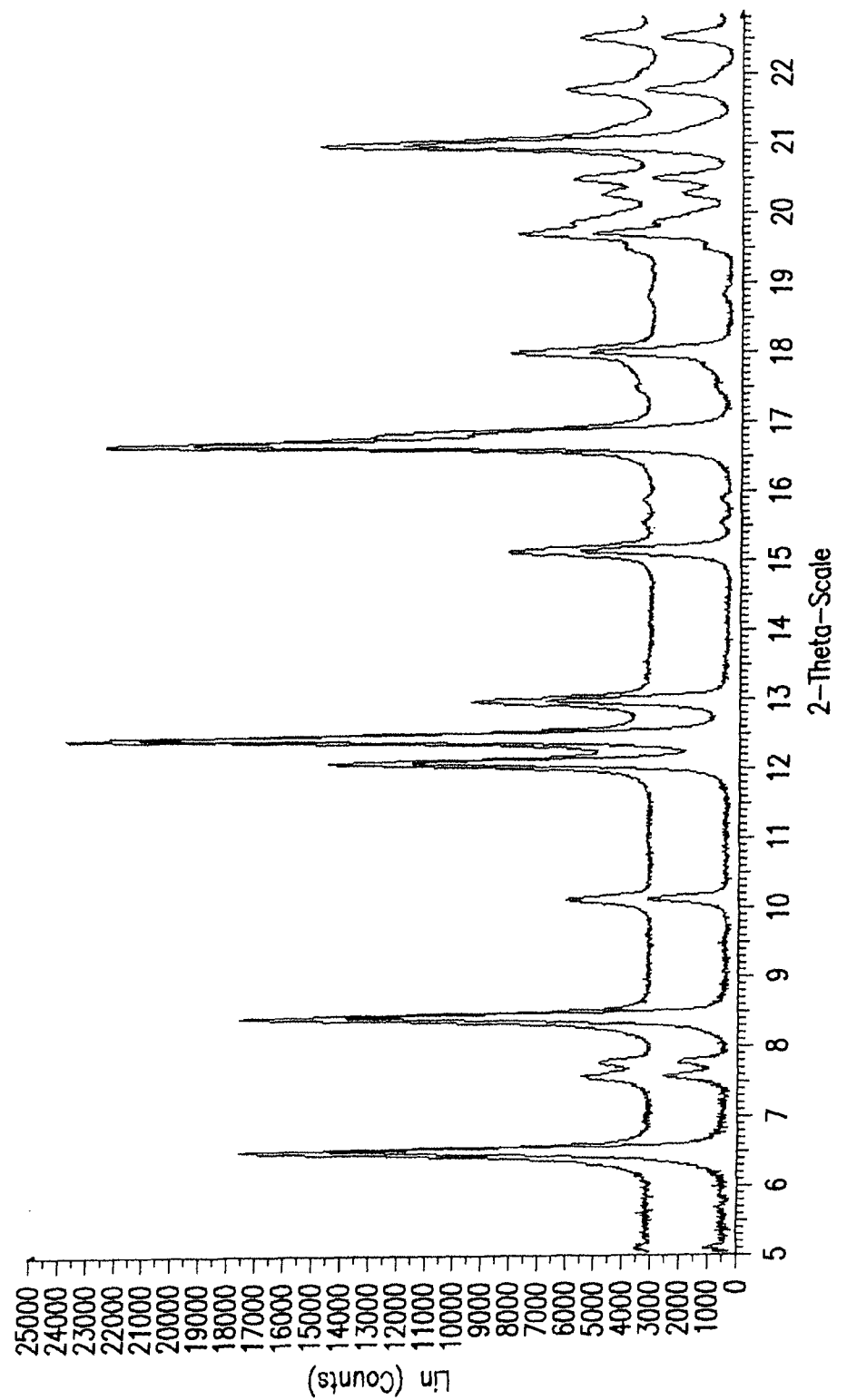
FIG. 7. XRD scans of Form II before and after exposure to a relative humidity of 50-60% at an ambient temperature of 20-25° C. for 24 hours.

FIG. 6 is an XRD scan of two batches of crystalline (E)-N-{4-[3-chloro-4-(2-pyridinylmethoxy)anilino]-3-cyano-7-ethoxy-6-quinolinyl}-4-(dimethylamino)-2-butenamide maleate in Form I. The anhydrous form of the maleate salt absorbs water and partially converts to the monohydrate form of the maleate salt at an ambient temperature of 20-25° C. over 24 hours. The monohydrate form of the maleate salt is relatively stable at an ambient temperature of 20-25° C. for 24 hours. FIG. 7 illustrates an XRD scan of crystalline (E)-N-{4-[3-chloro-4-(2-pyridinylmethoxy)anilino]-3-cyano-7-ethoxy-6-quinolinyl}-4-(dimethylamino)-2-butenamide maleate in Form II, before and after exposure to relative humidity of 50-60% at an ambient temperature of 20-25° C. for 24 hours. Exposing the monohydrate form of the maleate salt to higher temperatures (>50° C.) or heating under reduced pressure promotes water loss and full conversion back to the anhydrous form of the maleate salt.

Figure 8:
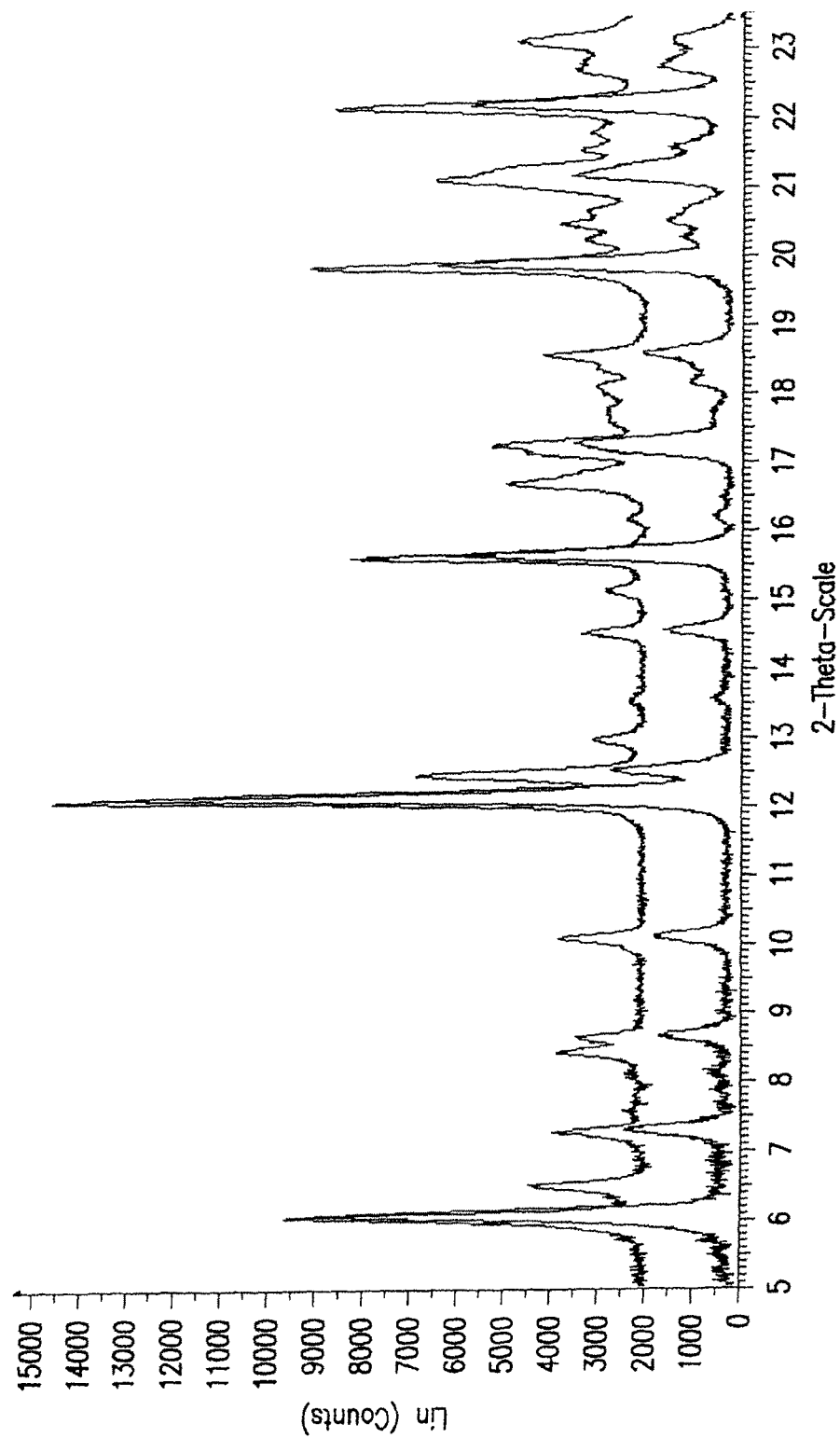
FIG. 8 XRD scans of Form I before and after exposure to relative humidity of 50-60% at an ambient temperature of 20-25° C. for 24 hours.

Form I, the anhydrous form, is readily converted to the monohydrate form, Form II. Form I can absorb water and convert partially to the monohydrate at a temperature of 20-25° C. and a relative humidity (RH) of 50-60% over time, as shown in FIG. 8. FIG. 8 is an XRD scan of crystalline (E)-N-{4-[3-chloro-4-(2-pyridinylmethoxy)anilino]-3-cyano-7-ethoxy-6-quinolinyl}-4-(dimethylamino)-2-butenamide maleate in Form I before (lower scan), and after (upper scan) exposure to relative humidity of 50-60% at room temperature of 20-25° C. for 24 hours. Hydrate peaks appear in the upper scan, indicating that the crystals absorb water under these conditions.

The stability of both forms of the maleate salt of (E)-N-{4-[3-chloro-4-(2-pyridinylmethoxy)anilino]-3-cyano-7-ethoxy-6-quinolinyl}-4-(dimethylamino)-2-butenamide was evaluated in closed and open containers at 40° C. and 75% RH. Both Form I and Form II remained stable for 6 months under these conditions. In the open containers, the anhydrous form of the maleate salt rapidly absorbed one mole of water to form the monohydrate form of the maleate salt. Samples in the closed containers remained dry. HPLC purity analysis indicated no significant increase in degradation products in both open and closed conditions for up to 6 months. The data is summarized in Table 5.

TABLE 5

SOLID STATE STABILITY OF THE ANHYDROUS MALEATE SALT (FORM I)

| | Closed Vial at 40° C./75% RH | | | | | Open Vial at 40° C./75% RH | | | | |
|---|---|---|---|---|---|---|---|---|---|---|
| Weeks in Storage | Potency as is (%) | Moisture (%) | Potency (dry basis) (%) | Major degradant (%) | Total impurities (%) | Potency as is (%) | Moisture (%) | Potency (dry basis) (%) | Major degradant (%) | Total impurities (%) |
| Initial | 100.50 | 0.35 | 100.85 | 0.23 | 0.57 | 100.50 | 0.35 | 100.85 | 0.23 | 0.57 |
| 1 | 100.07 | 0.39 | 100.46 | 0.23 | 0.57 | 99.13 | 2.82 | 102.02 | 0.22 | 0.55 |
| 2 | 100.03 | 0.34 | 100.38 | 0.24 | 0.64 | 97.50 | 2.86 | 100.37 | 0.23 | 0.65 |
| 4 | 96.87 | 0.22 | 97.09 | 0.24 | 0.61 | 95.27 | 2.74 | 97.96 | 0.23 | 0.58 |
| 12 | 100.21 | 0.46 | 100.67 | 0.25 | 0.66 | 98.12 | 2.98 | 101.13 | 0.26 | 0.65 |
| 24 | 98.96 | 0.16 | 99.12 | 0.32 | 0.68 | 97.22 | 2.79 | 100.01 | 0.31 | 0.69 |

Reactive crystallization of the free base with maleic acid in different solvents was performed to determine which crystalline form(s) of the maleate salt resulted. Table 6 illustrates the results of the crystallization process in a mixture of n-propanol and water at various operating conditions. The wet cake in all experiments contains the monohydrate form of the maleate salt, which converts to the anhydrous form of the maleate salt after drying.

TABLE 6

REACTIVE CRYSTALLIZATION OF MALEATE SALT IN WATER/N-PROPANOL

| Exp # | T, ° C. | Conditions | Form, wet cake | Form, dry solid (50° C. and vacuum) |
|---|---|---|---|---|
| 1 | 25 | 10% water | Hydrate Form II | I + II (1 hr drying) |
| 2 | 45 | 10% water | Hydrate Form II | ----- |
| 3 | 60 | 10% water | Hydrate Form II | ----- |
| 4 | Variable | 5% excess acid + 10% water | Hydrate Form II | I + II (1 hr drying) |
| 5 | Variable | 10% excess acid + 10% water | Hydrate Form II | ----- |
| 6 | Variable | 20% excess acid + 10% water | Hydrate Form II | ----- |
| 7 | Variable | 15% water | Hydrate Form II | I + II (1 hr drying) |
| 8 | 25 | 13% water | Hydrate Form II | Anhydrous Form I (overnight drying) |
| 9 | 25 | 13% water | Hydrate Form II | ----- |
| 10 | 45 | 13% water | Hydrate Form II | ----- |
| 11 | 45 | 13% water | Hydrate Form II | ----- |
| 12 | 25 | 15% water | Hydrate Form II | ----- |
| 13 | 25 | 15% water | Hydrate Form II | Anhydrous Form I (overnight drying) |
| 14 | 45 | 15% water | Hydrate Form II | ----- |
| 15 | 45 | 15% water | Hydrate Form II | ----- |

Table 7 presents the results of reactive crystallization of the free base and maleic acid in various solvents, which resulted in anhydrous form of the maleate salt in all experiments.

TABLE 7

REACTIVE CRYSTALLIZATION OF MALEATE SALT IN VARIOUS SOLVENTS

| Exp # | T, ° C. | Solvent | Form, dry solid 50° C. and vacuum for 1 hr |
|---|---|---|---|
| 1 | Variable | Ethanol | Anhydrous Form I |
| 2 | Variable | Isopropanol | Anhydrous Form I |
| 3 | Variable | Ethyl acetate | Anhydrous Form I |
| 4 | Variable | Acetone | Anhydrous Form I |
| 5 | Variable | THF | Anhydrous Form I |
| 6 | Variable | Acetonitrile | Anhydrous Form I |
| 7 | Variable | Isopropyl acetate | Anhydrous Form I |

One solvent that appreciably dissolves the (E)-N-{4-[3-chloro-4-(2-pyridinylmethoxy)anilino]-3-cyano-7-ethoxy-6-quinolinyl}-4-(dimethylamino)-2-butenamide maleate salt is dimethylsulfoxide (DMSO). Cooling, anti-solvent and evaporative crystallization were performed in mixtures of DMSO and isopropanol or t-butyl methyl ether (tBME). The approach led to the decomposition of the solute in many cases. Anti-solvent and evaporative crystallization did not result in any new crystalline forms, as summarized in Tables 8 and 9.

TABLE 8

ANTI-SOLVENT CRYSTALLIZATION OF MALEATE SALT FORMS

| Exp # | T, ° C. | Solvent | Form, wet cake |
|---|---|---|---|
| 1 | Salt dissolved in 5 vol. DMSO at T = 60° C. | 25 vol. IPA added at once | Anhydrous Form I |
| 2 | Salt dissolved in 5 vol. DMSO at T = 60° C. | 20 vol. water added at once | Hydrate Form II |
| 3 | Salt dissolved in 5 vol. DMSO at T = 60° C. | 2 vol. water and 25 vol. IPA added. Nucleated overnight | Hydrate Form II |

TABLE 9

EVAPORATIVE CRYSTALLIZATION OF MALEATE SALT FORMS

| Exp # | Solvent | | Form, dry sample |
|---|---|---|---|
| 1 | DMSO:IPA | T = 50° C. vacuum | Anhydrous Form I |
| 2 | DMSO:IPA | T = 50° C. vacuum | Anhydrous Form I |
| 3 | DMSO:IPA | T = 50° C. vacuum | Anhydrous Form I |
| 4 | DMSO:IPA | T = 50° C. vacuum | Anhydrous Form I |

According to one embodiment, one way to convert anhydrous Form I into monohydrate Form II is by dissolving the salt into a solution of an organic solvent, for example such as THF, isopropanol (IPA), n-propanol, acetone, ethanol, methanol, and acetonitrile, and water, where in the water present Is about 5% to about 20% by volume, though typically the water present is about 10% to about 15% by volume. This solution may be heated to increase solubility of the maleate salt; in one embodiment it is heated to about 45° C. or greater, in another embodiment it is heated to about 60° C. The solution is then allowed to sit for a period of hours to allow for crystallization, and the crystals are then filtered to give monohydrate Form II (see Table 6). In one embodiment the solution is allowed to sit for between about 12 and about 24 hours before filtration.

According to a separate embodiment, Form I is converted to Form II by re-slurrying it in organic solvent containing water and allowing the solution to stand exposed to the room temperature for several days, as shown in stability studies summarized in Table 10. This conversion will take place even in anhydrous solvents that have absorbed up to 1% water because anhydrous Form I readily absorbs moisture, as evidenced by FIG. 8. In one embodiment the re-slurry is allowed to stand for about 14 days.

TABLE 10

STABILITY OF CRYSTALLINE FORMS OF THE RESLURRY AT ROOM TEMPERATURE FOR 14 DAYS.

| Exp#* | Solvent | Initial Form | Final Form, wet cake |
|---|---|---|---|
| 1 | Ethanol | I | I |
| 2 | IPA | I | I |
| 3 | Ethyl acetate | I | I + some II |
| 4 | Acetone | I | I |
| 5 | THF | I | II |
| 6 | Acetonitrile | I | I |
| 7 | Methanol | I | I |
| 8 | Water | I | II |

TABLE 10-continued

STABILITY OF CRYSTALLINE FORMS OF THE RESLURRY AT ROOM TEMPERATURE FOR 14 DAYS.

| Exp#* | Solvent | Initial Form | Final Form, wet cake |
|---|---|---|---|
| 9 | DMSO:IPA(1:1) | I | I |
| 10 | Ethanol | II | II |
| 11 | IPA | II | II |
| 12 | Ethyl acetate | II | II |
| 13 | Acetone | II | II |
| 14 | THF | II | II |
| 15 | Acetonitrile | II | II |
| 16 | Methanol | II | I |
| 17 | DMSO:IPA(1:1) | II | I |

The present invention is also directed to compounds associated with the free base or the maleate salt of (E)-N-{4-[3-chloro-4-(2-pyridinylmethoxy)anilino]-3-cyano-7-ethoxy-6-quinolinyl}-4-(dimethylamino)-2-butenamide, or the methods of this invention. One or more of these associated compounds may be found in the cooled solution in a process of this invention. Since these compounds may not be separated from the maleate salt, a pharmaceutical formulation prepared with the maleate salt may contain one or more of these compounds.

Formulations of the maleate salt were prepared and stored in 40° C./75% RH stability chambers for six months and in a 56° C. oven for one month. Samples were periodically pulled for testing. Samples were dissolved in 50/50 volume/volume acetonitrile/water with a concentration at about 0.5 mg/mL. The solutions were assayed directly using LC/MS methodology to identify any degradation products and impurities (referred to herein as associated compounds) at six-months. Structures of the associated compounds, detected by LC/MS are listed in Table 11. Notably, the amount of the degradation product associated with (E)-N-{4-[3-chloro-4-(2-pyridinylmethoxy)anilino]-3-cyano-7-ethoxy-6-quinolinyl}-4-(dimethylamino)-2-butenamide maleate is reduced by the production method of the present invention.

TABLE 11

STRUCTURES OF DEGRADATION PRODUCT AND PROCESS IMPURITIES

Process Impurity A

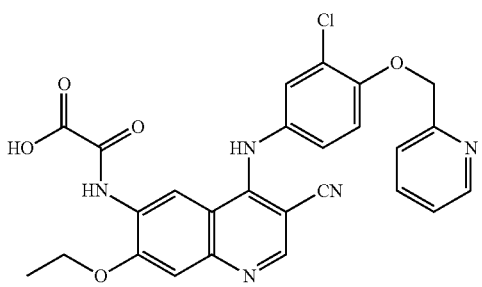

2-({4-[3-chloro-4-(2-pyridinylmethoxy)anilino]-3-cyano-7-ethoxy-6-quinolinyl}amino)-2-oxoacetic acid
Exact Mass: 517.12

TABLE 11-continued

STRUCTURES OF DEGRADATION PRODUCT AND PROCESS IMPURITIES

Process Impurity B

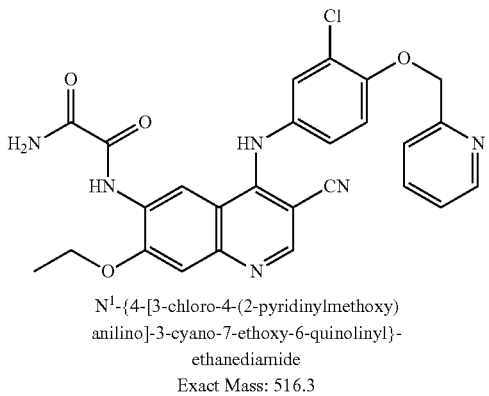

$N^1$-{4-[3-chloro-4-(2-pyridinylmethoxy)anilino]-3-cyano-7-ethoxy-6-quinolinyl}-ethanediamide
Exact Mass: 516.3

Process Impurity C

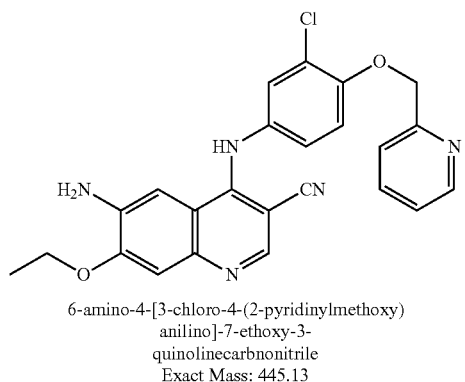

6-amino-4-[3-chloro-4-(2-pyridinylmethoxy)anilino]-7-ethoxy-3-quinolinecarbnonitrile
Exact Mass: 445.13

Degradation Product A

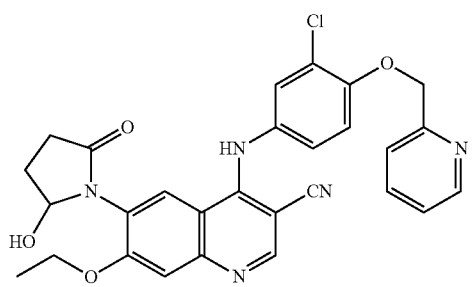

4-[3-chloro-4-(2-pyridinylmethoxy)anilino]-7-ethoxy-6-(2-hydroxy-5-oxopyrrolidinyl)-3-quinolinecarbonitrile
Exact Mass: 529.15

TABLE 11-continued

STRUCTURES OF DEGRADATION PRODUCT AND PROCESS IMPURITIES

Process Impurity D

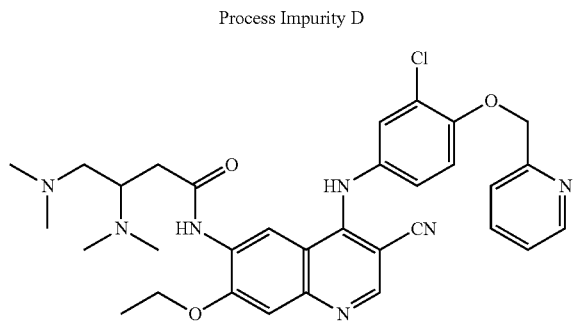

N-{4-[3-chloro-4-(2-pyridinylmethoxy)
anilino]-3-cyano-7-ethoxy-6-quinolinyl}-3,4-
bis(dimethylamino)butanamide
Exact Mass: 601.26

Process Impurity E

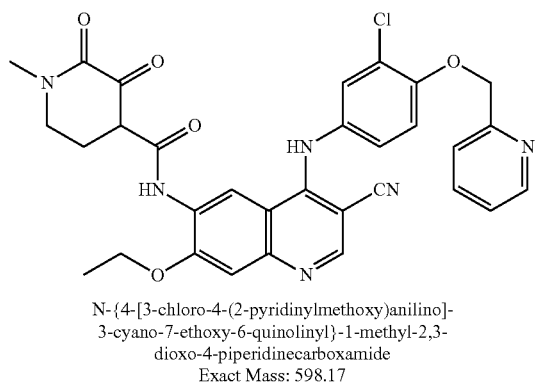

N-{4-[3-chloro-4-(2-pyridinylmethoxy)anilino]-
3-cyano-7-ethoxy-6-quinolinyl}-1-methyl-2,3-
dioxo-4-piperidinecarboxamide
Exact Mass: 598.17

Process Impurity F

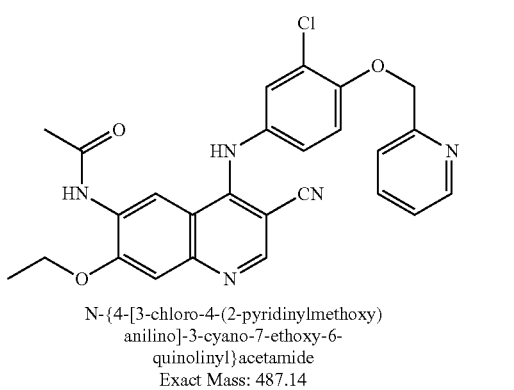

N-{4-[3-chloro-4-(2-pyridinylmethoxy)
anilino]-3-cyano-7-ethoxy-6-
quinolinyl}acetamide
Exact Mass: 487.14

Process Impurity G

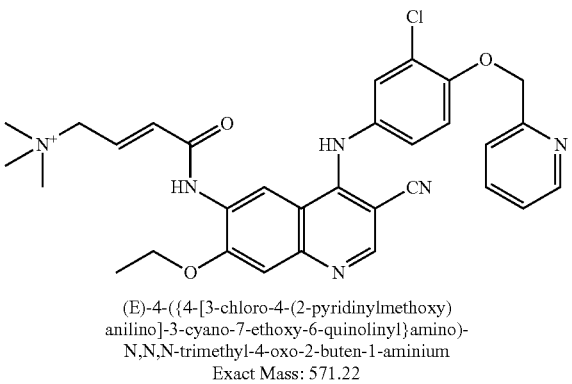

(E)-4-({4-[3-chloro-4-(2-pyridinylmethoxy)
anilino]-3-cyano-7-ethoxy-6-quinolinyl}amino)-
N,N,N-trimethyl-4-oxo-2-buten-1-aminium
Exact Mass: 571.22

Process Impurity H

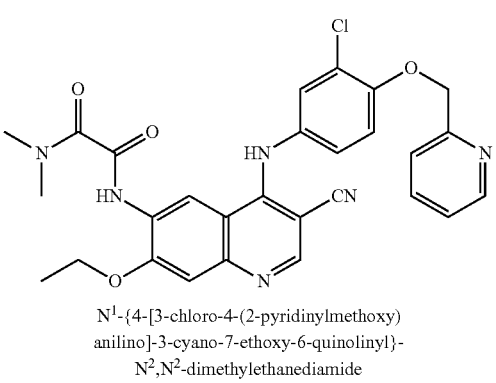

$N^1$-{4-[3-chloro-4-(2-pyridinylmethoxy)
anilino]-3-cyano-7-ethoxy-6-quinolinyl}-
$N^2,N^2$-dimethylethanediamide
Exact Mass: 544.16

Process Impurity I

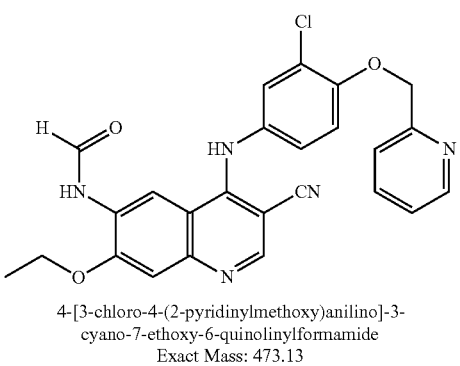

4-[3-chloro-4-(2-pyridinylmethoxy)anilino]-3-
cyano-7-ethoxy-6-quinolinylformamide
Exact Mass: 473.13

TABLE 11-continued

STRUCTURES OF DEGRADATION PRODUCT AND PROCESS IMPURITIES

Process Impurity J

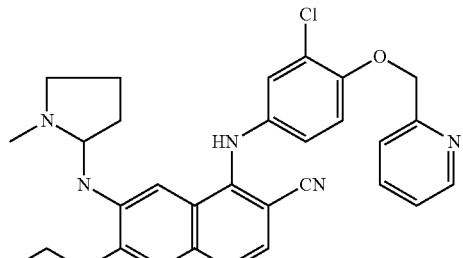

4-[3-chloro-4-(2-pyridinylmethoxy)anilino]-
7-ethoxy-6-[(1-methyl-2-pyrrolidinylidene)amino]-3-
quinolinecarbonitrile
Exact Mass: 526.19

The names of these associated compounds are:
2-({4-[3-chloro-4-(2-pyridinylmethoxy)anilino]-3-cyano-7-ethoxy-6-quinolinyl}amino)-2-oxoacetic acid;
$N^1$-{4-[3-chloro-4-(2-pyridinylmethoxy)anilino]-3-cyano-7-ethoxy-6-quinolinyl}-ethanediamide;
6-amino-4-[3-chloro-4-(2-pyridinylmethoxy)anilino]-7-ethoxy-3-quinolinecarbonitrile;
4-[3-chloro-4-(2-pyridinylmethoxy)anilino]-7-ethoxy-6-(2-hydroxy-5-oxopyrrolidinyl)-3-quinolinecarbonitrile;
N-{4-[3-chloro-4-(2-pyridinylmethoxy)anilino]-3-cyano-7-ethoxy-6-quinolinyl}-3,4-bis(dimethylamino)butanamide;
N-{4-[3-chloro-4-(2-pyridinylmethoxy)anilino]-3-cyano-7-ethoxy-6-quinolinyl}-1-methyl-2,3-dioxo-4-piperidinecarboxamide;
N-{4-[3-chloro-4-(2-pyridinylmethoxy)anilino]-3-cyano-7-ethoxy-6-quinolinyl}acetamide;
(E)-4-({4-[3-chloro-4-(2-pyridinylmethoxy)anilino]-3-cyano-7-ethoxy-6-quinolinyl}amino)-N,N,N-trimethyl-4-oxo-2-buten-1-aminium
$N^1$-{4-[3-chloro-4-(2-pyridinylmethoxy)anilino]-3-cyano-7-ethoxy-6-quinolinyl}-$N^2$,$N^2$-dimethylethanediamide;
4-[3-chloro-4-(2-pyridinylmethoxy)anilino]-3-cyano-7-ethoxy-6-quinolinylformamide; and,
4-[3-chloro-4-(2-pyridinylmethoxy)anilino]-7-ethoxy-6-[(1-methyl-2-pyrrolidinylidene)amino]-3-quinolinecarbonitrile.

Crystalline forms of the maleate salts of the present invention are useful for preventing, treating, or inhibiting inflammation or cancer by administering a therapeutically-effective amount of (E)-N-{4-[3-chloro-4-(2-pyridinylmethoxy)anilino]-3-cyano-7-ethoxy-6-quinolinyl}-4-(dimethylamino)-2-butenamide maleate to a subject. The subject may be a mammal, and more specifically, a human. The maleate salt may be administered in its anhydrous form, monohydrate form or partially hydrated form. One or more of the associated compounds discussed above may also be administered during this method.

Crystalline forms of the maleate salts of the present invention are useful for preparing pharmaceutical compositions for the Inhibition of HER-2 kinase activity, which is linked to the treatment of cancer. The formulations contain a therapeutically effective amount of (E)-N-{4-[3-chloro-4-(2-pyridinylmethoxy)anilino]-3-cyano-7-ethoxy-6-quinolinyl}-4-(dimethylamino)-2-butenamide maleate and a pharmaceutically acceptable carrier. The pharmaceutical composition may be administered in its anhydrous form, monohydrate form or partially hydrated form. One or more of the associated compounds discussed above may also be administered during this method.

Pharmaceutical compositions and formulations of the present invention may be useful in the treatment of one or more of breast cancer, ovarian cancer, epidermoid tumors, colon cancer, prostate cancer, kidney cancer, bladder cancer, larynx cancer, esophagus cancer, stomach cancer, and lung cancer. According to one embodiment, the maleate salt is particularly useful in the treatment of breast cancer and/or ovarian cancer.

The pharmaceutical compositions and formulations including maleate salt forms of the invention may be administered orally, by intralesional, intraperitoneal, intramuscular or intravenous injection; infusion; liposome-mediated delivery; topical, nasal, anal, vaginal, sublingual, urethral, transdermal, intrathecal, ocular or otic delivery. One mode of administration for the compound of the invention is the unit dose form. Suitable unit dose forms include tablets, capsules and powders in sachets or vials. The crystalline compounds of the present invention can be administered orally. Such compounds may be administered from 1 to 6 times a day, more usually from 1 to 4 times a day. The effective amount will be known to one of skill in the art; it may also be dependent upon the form of the compound, the mode of administration and the serverity of the condition being treated. One of skill in the art could routinely perform empirical activity tests to determine the bioactivity of the compound in bioassays and thus determine what dosage to administer. However, in general, satisfactory results can be obtained with compounds of the present invention when dosed daily in the range of about 0.5 mg/kg to about 1000 mg/kg of body weight, but usually the effective dosage amount is between about 1 mg/kg to about 300 mg/kg per day.

The crystalline forms of maleate salts of the invention may be formulated with conventional excipients, such as fillers, disintegrating agents, binders, lubricants, flavoring agents, color additives, and carriers. The carrier may be a diluent, an aerosol, a topical carrier, an aqueous solution, a nonaqueous solution or a solid. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

If administered orally or topically, the crystalline forms of maleate salts of the invention may be provided to a subject in different carriers. Typically, such carriers contain excipients such as starch, milk, sugar, certain types of clay, gelatin, stearic acid, talc, vegetable fats or oils, gums, or glycols. Specific carriers are typically selected based upon the desired method of delivery, for example, phosphate buffered saline (PBS) could be used for intravenous or systemic delivery and vegetable fats, creams, salves, ointments or gels may be used for topical delivery.

The crystalline forms of maleate salts of the present invention may be delivered together with suitable diluents, preservatives, solubilizers, emulsifiers, adjuvants and/or carriers useful in treatment, inhibition or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN™ 20, TWEEN™ 80, PLURONIC™ F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroblasts. Such compositions will influence the physical state, solubility, stability, rate of in vivo release, and rate of in-vivo clearance of the compound or composition. The choice of compositions will depend on the physical and chemical properties of the compound.

The crystalline forms of maleate salts of the invention also may be delivered locally via a capsule that allows a sustained release of the compound over a period of time. Controlled or sustained release compositions include formulations in lipophilic depots (for example, fatty acids, waxes, oils).

The crystalline forms of maleate salts of the invention can also be dosed with other active compounds that would be of benefit to a patient suffering from cancer, for example, other chemo agents or anti-biotics, or in conjunction with radiation therapy. These active compounds can be dosed with the compounds of the present invention simultaneously or in sequence. The compounds of the present invention can also be formulated to include the other active compound in the same dosage unit, for example both could be contained within one pill, table or capsule. Some of the possible types of active compounds that the compounds of the present invention could be used in combination with are mitotic inhibitors, such as taxol and vinblastine, alylating agents, such as cisplatin and cyclophosamide, antimetabolites, such as 5-fluorouracil and hydroxyurea, DNA intercalators, such as adriamycin and bleomycin, topoisomerase inhibitors, such as etoposide and camptothecin, antiangiogenic agents, such as angiostatin, and antiestrogens, such as tamoxifen.

This invention will be more fully described in conjunction with the following specific examples, which should not to be construed as limiting the scope of this invention. A skilled artisan will be able to re-arrange, combine, modify, or eliminate steps in the exemplified process, depending on process parameters and equipment.

EXAMPLE 1

Preparation of (E)-N-{4-[3-chloro-4-(2-pyridinylmethoxy)anilo]-3-cyano-7-ethoxy-6-quinolinyl}-4-(dimethylamino)-2-butenamide Maleate, Form II Crude (E)-N-{4-[3-chloro-4-(2-pyridinylmethoxy)anilino]-3-cyano-7-ethoxy-6-quinolinyl}-4-(dimethylamino)-2-butenamide free base (0.100 kg, 0.159 mole) is rinsed with a 10% solution of USP purified water in n-propanol (0.082 kg, 0.10 L) followed by the addition of water:n-propanol solution (0.74 kg, 0.90 L). Maleic acid is added (0.0191 kg, 0.164 mole) and the mixture is rinsed with 10% water:n-propanol (0.082 kg, 0.10 L). The mixture is quickly heated to 50-60° C. and held for a minimum of 15 min. until a solution is obtained. The hot solution is clarified through a pre-heated 50-60° C., 0.2 Mm filter cartridge and the filtrates are collected in a preheated 45-55° C., 2 L multi-neck flask. The filter cartridge is rinsed through with 10% water:n-propanol pre-heated to 45-55° C. (0.082 kg, 0.10 L). The solution is cooled over at least one hour to 40° C. and held at that temperature for 12 hours then cooled to room temperature (25° C.) over a minimum of four hours and held at that temperature for at least two hours. The mixture id filtered on a 12.5 cm diameter Buchner funnel for 5 min., then rinsed and washed with pre-filtered 10% water:n-propanol solution (2×0.12 kg, 2×0.15 L). The cake is dammed and suction maintained until dripping essentially stops, about 1 h.

EXAMPLE 2

Preparation of (E)-N-{4-[3-chloro-4-(2-pyridinylmethoxy)anilino]-3-cyano-7-ethoxy-6-quinolinyl}-4-(dimethylamino)-2-butenamide Maleate, Form I The product from Example 1 (Form II) is dried (50° C., 10 mm Hg, 24 h) to give 94.4 g (88% yield) of crystalline, anhydrous (E)-N-{4-[3-chloro-4-(2-pyridinylmethoxy)anilino]-3-cyano-7-ethoxy-6-quinolinyl}-4-(dimethylamino)-2-butenamide maleate (Form I) (88% yield) with strength 80.8% (free base), 17.4% (maleic acid), total impurities 1.06%, largest single impurity 0.38%.

The invention claimed is:

1. A method of treating cancer, comprising:
   administering to a patient in need thereof neratinib formulated as a crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate;
   wherein:
   i) the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate is characterized by X-ray diffraction peaks at the following angles)(±0.20° of 2Theta in its X-ray diffraction pattern comprising 6.16, 7.38, 8.75, 12.61, 14.65, and 15.75; and
   ii) when administered to a patient, the formulation of the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate produces at least a two-fold greater area under the curve, relative to neratinib in a free base formulation.

2. The method of claim 1, wherein the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate is characterized by X-ray diffraction peaks at the following angles)(±0.20° of 2Theta in its X-ray diffraction pattern comprising 6.16, 7.38, 8.75, 12.24, 12.61, 14.65, 15.75, 17.33, 18.64, 19.99, 21.32, and 22.30.

3. The method of claim 1, wherein the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate is characterized by X-ray diffraction peaks at the following angles)(±0.20° of 2Theta in its X-ray diffraction pattern comprising 6.16, 7.38, 8.75, 10.20, 12.24, 12.61, 14.65, 15.75, 17.33, 18.64, 19.99, 20.66, 21.32, 22.30, 23.18, 24.10, 24.69, 25.49, 26.09, 26.54, 27.52, 28.62, and 29.43.

4. The method of claim 1, wherein the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate has substantially the X-ray diffraction pattern as shown in FIG. 6.

5. The method of claim 1, wherein the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate has substantially the X-ray diffraction pattern as shown in FIG. 1 (lower scan).

6. The method of claim 1, wherein the cancer is selected from the group consisting of: breast cancer, ovarian cancer, epidermoid tumors, colon cancer, prostate cancer, kidney cancer, bladder cancer, larynx cancer, esophagus cancer, stomach cancer, and lung cancer.

7. The method of claim 1, wherein the cancer is breast cancer.

8. The method of claim 1, wherein the cancer is lung cancer.

9. The method of claim 1, wherein when administered to a patient, the formulation of the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate mitigates interactions with emetic receptors relative to neratinib in a free base formulation.

10. The method of claim 1, wherein when administered to a patient, the formulation of the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate reduces diarrhea, relative to neratinib in a free base formulation.

11. The method of claim 1, wherein the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate is prepared according to a method comprising:
  i) mixing (E)-N-{4-[3-chloro-4-(2-pyridinylmethoxy)anilino]-3-cyano-7-ethoxy-6-quinolinyl}-4-(dimethylamino)-2-butenamide and maleic acid in a water-alcohol solution at a temperature in the range of between about 50° C. to about 60° C.;
  ii) cooling said solution to a temperature of about 40° C. and maintaining the cooled solution at about 40° C. for about 12 hours to precipitate the maleate salt;
  iii) further cooling the cooled solution to room temperature (about 25° C.) over a minimum of 4 hours and maintaining the further cooled solution at room temperature (about 25° C.) for at least 2 hours;
  iv) filtering the maintained, further cooled solution to obtain crystalline (E)-N-{4-[3-chloro-4-(2-pyridinylmethoxy)anilino]-3-cyano-7-ethoxy-6-quinolinyl}-4-(dimethylamino)-2-butenamide maleate, wherein the crystalline (E)-N-{4-[3-chloro-4-(2-pyridinylmethoxy)anilino]-3-cyano-7-ethoxy-6-quinolinyl}-4-(dimethylamino)-2-butenamide maleate is (E)-N-{4-[3-chloro-4-(2-pyridinylmethoxy)anilino]-3-cyano-7-ethoxy-6-quinolinyl}-4-(dimethylamino)-2-butenamide maleate, monohydrate; and
  v) drying the crystalline (E)-N-{4-[3-chloro-4-(2-pyridinylmethoxy)anilino]-3-cyano-7-ethoxy-6-quinolinyl}-4-(dimethylamino)-2-butenamide maleate, monohydrate, under vacuum at a temperature greater than 30° C. for 12 to 48 hours to obtain said crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate.

12. The method of claim 11, wherein the drying step comprises drying the (E)-N-{4-[3-chloro-4-(2-pyridinylmethoxy)anilino]-3-cyano-7-ethoxy-6-quinolinyl}-4-(dimethylamino)-2-butenamide maleate, monohydrate, at 50° C., 10 mm Hg for 24 hours to obtain said crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate.

13. A method of treating cancer, comprising:
  administering to a patient in need thereof neratinib formulated as a crystalline form of (E)-N-{4-[3-chloro-4-(2-pyridinylmethoxy)anilino]-3-cyano-7-ethoxy-6-quinolinyl}-4-(dimethylamino)-2-butenamide maleate, monohydrate;
wherein:
  i) the crystalline form of (E)-N-{4-[3-chloro-4-(2-pyridinylmethoxy)anilino]-3-cyano-7-ethoxy-6-quinolinyl}-4-(dimethylamino)-2-butenamide maleate, monohydrate, is characterized by X-ray diffraction peaks at the following angles)(±0.20° of 2Theta in its X-ray diffraction pattern comprising 6.53, 8.43, 12.19, 12.47, 13.01, 16.76, and 21.11; and
  ii) when administered to a patient, the formulation of the crystalline form of anhydrous (E)-N-{4-[3-chloro-4-(2-pyridinylmethoxy)anilino]-3-cyano-7-ethoxy-6-quinolinyl}-4-(dimethylamino)-2-butenamide maleate, monohydrate, produces at least a two-fold greater area under the curve, relative to neratinib in a free base formulation.

14. The method of claim 13, wherein the crystalline form of (E)-N-{4-[3-chloro-4-(2-pyridinyl methoxy)anilino]-3-cyano-7-ethoxy-6-quinolinyl}-4-(dimethylamino)-2-butenamide maleate, monohydrate, is characterized by X-ray diffraction peaks at the following angles)(±0.20° of 2Theta in its X-ray diffraction pattern comprising 6.53, 8.43, 12.19, 12.47, 13.01, 15.17, 16.76, 17.95, 19.86, and 21.11.

15. The method of claim 13, wherein the crystalline form of (E)-N-{4-[3-chloro-4-(2-pyridinyl methoxy)anilino]-3-cyano-7-ethoxy-6-quinolinyl}-4-(dimethylamino)-2-butenamide maleate, monohydrate, is characterized by X-ray diffraction peaks at the following angles)(±0.20° of 2Theta in its X-ray diffraction pattern comprising 6.53, 8.43, 10.16, 12.19, 12.47, 13.01, 15.17, 16.76, 17.95, 19.86, 21.11, 21.88, 23.22, 23.78, 25.69, 26.17, 27.06, 27.58, 28.26, 28.73, and 29.77.

16. The method of claim 13, wherein the crystalline form of (E)-N-{4-[3-chloro-4-(2-pyridinyl methoxy)anilino]-3-cyano-7-ethoxy-6-quinolinyl}-4-(dimethylamino)-2-butenamide maleate, monohydrate, has substantially the X-ray diffraction pattern as shown in FIG. 7.

17. The method of claim 13, wherein the crystalline form of (E)-N-{4-[3-chloro-4-(2-pyridinyl methoxy)anilino]-3-cyano-7-ethoxy-6-quinolinyl}-4-(dimethylamino)-2-butenamide maleate, monohydrate, has substantially the X-ray diffraction pattern as shown in FIG. 1 (upper scan).

18. The method of claim 13, wherein the cancer is selected from the group consisting of: breast cancer, ovarian cancer, epidermoid tumors, colon cancer, prostate cancer, kidney cancer, bladder cancer, larynx cancer, esophagus cancer, stomach cancer, and lung cancer.

19. The method of claim 13, wherein the cancer is breast cancer.

20. The method of claim 13, wherein the cancer is lung cancer.

21. The method of claim 13, wherein when administered to a patient, the formulation of the crystalline form of (E)-N-{4-[3-chloro-4-(2-pyridinylmethoxy)anilino]-3-cyano-7-ethoxy-6-quinolinyl}-4-(dimethylamino)-2-butenamide maleate, monohydrate, mitigates interactions with emetic receptors relative to neratinib in a free base formulation.

22. The method of claim 13, wherein when administered to a patient, the formulation of the crystalline form of (E)-N-{4-[3-chloro-4-(2-pyridinylmethoxy)anilino]-3- cyano-7-ethoxy-6-quinolinyl}-4-(dimethylamino)-2-butenamide maleate, monohydrate, reduces diarrhea, relative to neratinib in a free base formulation.

23. The method of claim 13, wherein the crystalline form of (E)-N-{4-[3-chloro-4-(2-pyridinylmethoxy)anilino]-3-cyano-7-ethoxy-6-quinolinyl}-4-(dimethylamino)-2-butenamide maleate, monohydrate, is prepared according to a method comprising:
  i) mixing (E)-N-{4-[3-chloro-4-(2-pyridinylmethoxy)anilino]-3-cyano-7-ethoxy-6-quinolinyl}-4-(dimethylamino)-2-butenamide and maleic acid in a water-alcohol solution at a temperature in the range of between about 50° C. to about 60° C.;
  ii) cooling said solution to a temperature of about 40° C. and maintaining the cooled solution at about 40° C. for about 12 hours to precipitate the maleate salt;
  iii) further cooling the cooled solution to room temperature (about 25° C.) over a minimum of 4 hours and maintaining the further cooled solution at room temperature (about 25° C.) for at least 2 hours; and
  iv) filtering the maintained, further cooled solution to obtain said crystalline form of (E)-N-{4-[3-chloro-4-(2-pyridinylmethoxy)anilino]-3-cyano-7-ethoxy-6-quinolinyl}-4-(dimethylamino)-2-butenamide maleate, monohydrate.

24. The method of claim 23, wherein the obtained crystalline form of (E)-N-{4-[3-chloro-4-(2-pyridinylmethoxy)anilino]-3-cyano-7-ethoxy-6-quinolinyl}-4-(dimethylamino)-2-butenamide maleate, monohydrate, has a water content of about 2.5 to 2.7%, by weight.

* * * * *

UNITED STATES PATENT AND TRADEMARK OFFICE
CERTIFICATE OF CORRECTION

PATENT NO. : 10,035,788 B2
APPLICATION NO. : 15/463998
DATED : July 31, 2018
INVENTOR(S) : Qinghong Lu et al.

Page 1 of 1

It is certified that error appears in the above-identified patent and that said Letters Patent is hereby corrected as shown below:

In the Claims

Column 26, Claim 1, Line 38, replace "angles)(±0.20°" with --angles (±0.20°)--;
Column 26, Claim 2, Line 51, replace "angles)(±0.20°" with --angles (±0.20°)--;
Column 26, Claim 3, Line 58, replace "angles)(±0.20°" with --angles (±0.20°)--.

Column 28, Claim 13, Line 15, replace "angles)(±0.20°" with --angles (±0.20°)--;
Column 28, Claim 13, Line 19, delete "anhydrous";
Column 28, Claim 14, Line 29, replace "angles)(±0.20°" with --angles (±0.20°)--;
Column 28, Claim 15, Line 36, replace "angles)(±0.20°" with --angles (±0.20°)--.

Signed and Sealed this
Fourth Day of February, 2020

Andrei Iancu
*Director of the United States Patent and Trademark Office*